US009663569B2

(12) United States Patent
Karni et al.

(10) Patent No.: US 9,663,569 B2
(45) Date of Patent: May 30, 2017

(54) USE OF BLOCKING AGENTS OF BONE MORPHOGENIC PROTEIN (BMP) SIGNALLING FOR THE TREATMENT OF NEUROINFLAMMATORY AND NEURODEGENERATIVE DISEASES

(71) Applicant: THE MEDICAL RESEARCH, INFRASTRUCTURE, AND HEALTH SERVICES FUND OF THE TEL AVIV MEDICAL CENTER, Tel Aviv (IL)

(72) Inventors: Arnon Karni, Mevaseret Zion (IL); Yifat Amir Levi, Herzeliya (IL); Nataly Urshanski, Rehovot (IL); Karin Bernadet Fainberg, Ramat-Gan (IL)

(73) Assignee: THE MEDICAL RESEARCH, INFRASTRUCTURE, AND HEALTH SERVICES FUND OF THE TEL AVIV MEDICAL CENTER, Tel Aviv (IL)

( * ) Notice: Subject to any disclaimer, the term of this patent is extended or adjusted under 35 U.S.C. 154(b) by 0 days.

(21) Appl. No.: 14/408,263

(22) PCT Filed: Jun. 12, 2013

(86) PCT No.: PCT/IL2013/050503
§ 371 (c)(1),
(2) Date: Dec. 15, 2014

(87) PCT Pub. No.: WO2013/186777
PCT Pub. Date: Dec. 19, 2013

(65) Prior Publication Data
US 2015/0139983 A1    May 21, 2015

Related U.S. Application Data

(60) Provisional application No. 61/659,510, filed on Jun. 14, 2012.

(51) Int. Cl.
| | | |
|---|---|---|
| A61K 39/395 | (2006.01) |
| A61P 25/28 | (2006.01) |
| C07K 16/24 | (2006.01) |
| C07K 16/22 | (2006.01) |
| A61K 31/519 | (2006.01) |
| A61K 39/00 | (2006.01) |

(52) U.S. Cl.
CPC .......... C07K 16/24 (2013.01); A61K 31/519 (2013.01); A61K 39/3955 (2013.01); C07K 16/22 (2013.01); *A61K 2039/505* (2013.01); *A61K 2039/507* (2013.01); *C07K 2317/33* (2013.01); *C07K 2317/60* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,803,752 B2 | 9/2010 | Goldman et al. | |
| 2008/0249038 A1* | 10/2008 | Feinstein | C12N 15/1136 514/44 A |
| 2010/0003245 A1* | 1/2010 | Doi | C07K 16/22 424/133.1 |
| 2011/0182904 A1* | 7/2011 | Zimmerman | C07K 16/22 424/145.1 |

FOREIGN PATENT DOCUMENTS

| | | |
|---|---|---|
| WO | 2008030611 A2 | 3/2008 |
| WO | 2009106356 A1 | 9/2009 |

OTHER PUBLICATIONS

Simonini et al., ASN Neuro., 2010, vol. 2(1):e00025.*
Li et al., Hippocampus, 2008, vol. 18(7):692-698. (abstract).*
Li et al., Hippocampus, 2008, vol. 18(7):692-698.*
Trapp et al "Multiple Sclerosis: An Immune or Neurodegenerative Disorder?" Annu. Rev. Neurosci. 31:247-269 (2008).
Ferguson et al., "Axonal damage in acute multiple sclerosis lesions" Brain 120:393-399 (1997).
Snethen et al., "Disease-responsive neural precursor cells are present in multiple sclerosis lesions" Regen. Med. 3 (6) :835-847 (2008).
Kuhlmann et al., "Differentiation block of oligodendroglial progenitor cell as a cause for remyelination failure in chronic multiple sclerosis" Brain 131:1749-1758 (2008).
Lim et al., "Noffin Antagonizes BMP Signaling to Crete a Niche for Adult Neurogenesis" Neuron. 28:713-726 (2000).
Mabie et al., "Bone Morphogenetic Proteins Induce Astroglial Differentiation of Oligodendroglial-Astroglial Progenitor Cells" J Neurosci. 17:4112-4120 (1997).
Ara et al., "Bone Morphogenetic Proteins 4,6 and 7 Are Up-Regulated in Mouse Spinal Cord during Experimental Autoimmune Encephalomyelitis" J Neurosci. Res. 86:125-135 (2008).
Deininger et al., "Detection of two transforming growth factor-j-related morphogens, bone morphogenetic proteins-4 and -5, in RNA of multiple sclerosis and Creutzfeldt-Jakob disease lesions" Acta Neuropathol. 90:76-79 (1995).
Picard-Riera et al., "Experimental autoimmune encephalomyelitis mobilizes neural progenitors from the subventricular zone to undergo oligodendrogenesis in adult mice" Proc. Natl. Acad. U S A 99:13211-13216 (2002).
Yu et al., "Dorsomorphin inhibits BMP signals required for embryogenesis and iron metabolism" Nat. Chem. Biol. 4:33-41 (2008).
Rosen, "BMP and BMP Inhibitors in Bone" Ann. N. Y. Acad. Sci. 1068:19-25 (2006).

(Continued)

*Primary Examiner* — Xiaozhen Xie
(74) *Attorney, Agent, or Firm* — Browdy and Neimark, PLLC

(57) ABSTRACT

The invention provides pharmaceutical compositions for the treatment of neuroinflammatory or neurodegenerative diseases comprising a single or a combination of several blocking agent(s) of Bone Morphogenic Protein (BMP) signaling. The invention further provides methods of treatment of neuroinflammatory or neurodegenerative diseases comprising administering to a patient in need thereof the pharmaceutical compositions of the invention.

4 Claims, 33 Drawing Sheets

(56) References Cited

OTHER PUBLICATIONS

Balemans et al "Extracellular Regulation of BMP Signaling in Vertebrates: A Cocktail of Modulators" Dev. Biol. 250:231-250 (2002).
Yanagita "BMP antagonists: Their roles in development and involvement in pathophysiology" Cytokine Growth Factor Rev. 16:309-317 (2005).
Abreu et al., "Connectie-tissue growth factor (CTGF) modulates cell signalling by BMP and TGF-β" Nat. Cell. Biol. 4:599-604 (2002).
Sharrack et al. "The psychometric properties of clinical rating scales used in multiple sclerosis" Brain .122:141-159 (1999).
Kurtzke "Rating neurologic impairment in multiple sclerosis: An expanded disability status scale (EDSS)" Neurology. 33(11):1444-1452 (1983).
Kuhn et al.,"Neurogenesis in the dentate Gyrus of the Adult RAt: Age-Related Decrease of Neuronal Progenitor Proliferation" J Neurosci. 16:2027-2033 (1996).
Eto et al., "Alterations of Interneurons in the Striatum and Frontal Cortex of Mice During Postnatal Development" Int. J Dev. Neurosci. 28:359-370 (2010).
Sasaki. et al., "Target cells of apoptosis in the adult murine dentate gyrus and O4 immunoreacitivity after ionizing radiation" Neurosci. Lett. 279:57-60 (2000).
Simonin et al. "Regulation of oligodendrocyte progenitor cell maturation by PPARS: effects on bone morphogenetic proteins" ASN Neuro 8 (1) 241-13. XP055080462 (Jan. 2010).
Yousef et al "Age-Associated Increase in BMP Signaling Inhibits Hippocampal Neurogenesis" Stem Cells 33:1577-1588 (2015).
Setoglichi T et al. "Treatment of spinal cord injury by transplantation of fetal neural precursor cells engineered to express BMP inhibitor" Exp. Neurol. 189 (1): 33-44. XP004620695 (Sep. 2004).
Voumvourakis et al "TGF-B/bMP: Crucial crossroad in neural autoimmune disorders" Neurochem. Int. (59) 5 :542-550 . XP028292437 (Jun. 2011).
Corradini E et al. "The RGM/DRAGON family of BMP co-receptors" Cytokine Growth Factor Rev. 20 (5-6) : 389-398 XP026790608 (Oct. 2009).
*Homo sapiens* bone morphogenetic protein 2 (BMP2), mRNA Genbank Accession No. NM_001200.2 (accessed Sep. 6, 2013).
Bone morphogenetic protein 4 precursor—*Homo sapiens* (human) "(BMP4_Human) Reviewed. UniProtKb/Swiss-Prot". Accession No. P12644 (May 29, 2013).
Bone morphogenetic protein-5 precursor—*Homo sapiens* (human) "BMP5_Human) Reviewed. UniProtKB/Swiss-Prot". accesion No. P22003 (May 1, 2013).
Bone morphogenetic protein-7 precursor—*Homo sapiens* (human) "(BMP7_Human) Reviewed. UniProtKB/Swiss-Prot" accession No. P18075 (May 29, 2013).
Douet et al."Bone morphogenetic protein-4 inhibits adult neurogenesis and is regulated by fractoneassociated heparan sulfates in the subventricular zone" Journal of Chemical Neuroanatomy 57-58:54-61 (May 2014).
Fuller et al—"Bone Morphogenetic Proteins Promote Gliosis in Demylinating Spinal Cord Lesions" Annals of Neurology 62:288-300 (2007).
Song et al. "Agmatine enhances neurogenesis by increasing ERK1/2 expression, and suppresses astrogenesis by decreasing BMP 2,4 and SMAD 1,5,8 expression in subventricular zone neural stem cells" Life Sci. 89: 439-449 (Jan. 2011).
Sabo et al "Remyelination Is Altered by Bone Morphogenic Protein Signaling in Demyelinated Lesions" The Journal of Neuroscience. 31(21)4504-4510 (Mar. 2011).
Wang et al "Astrocytes from the Contused Spinal Cord Inhibit Oligodendrocyte Differentiation of Adult Oligodendrocyte Precursor Cells by Increasing the Expression of Bone Morphogenetic Protein" J. Neurosci 31(16): 6053-6058 (Apr. 2011).

\* cited by examiner

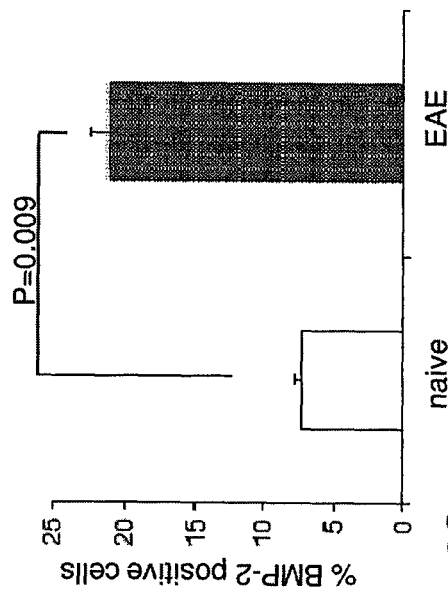
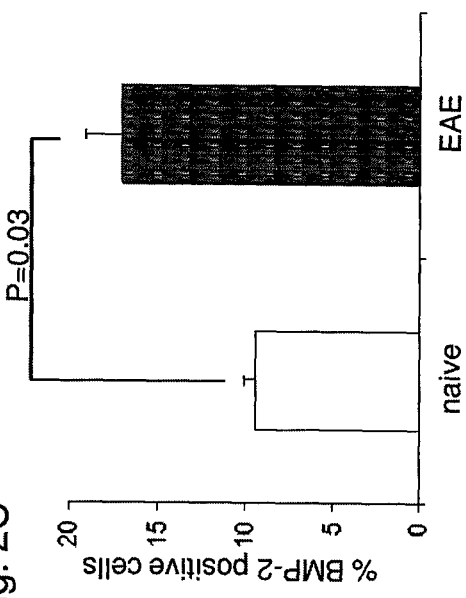
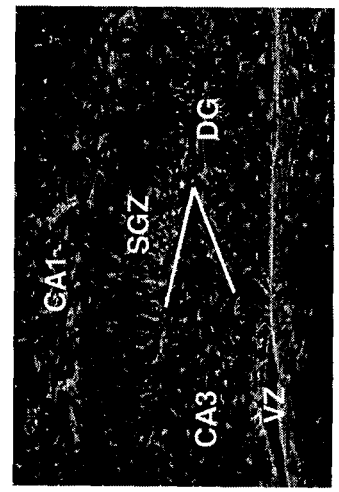
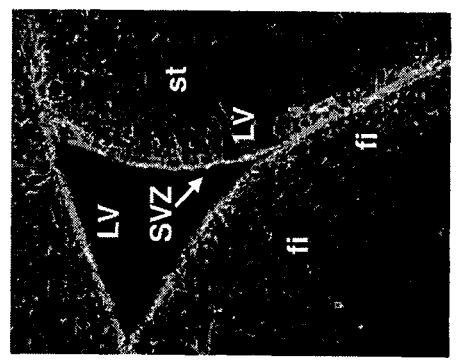
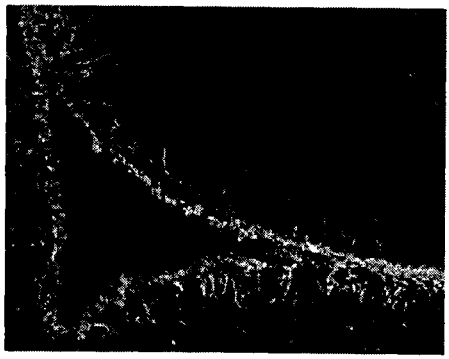
Fig. 2A  Fig. 2B  Fig. 2C
Fig. 2D  Fig. 2E  Fig. 2F

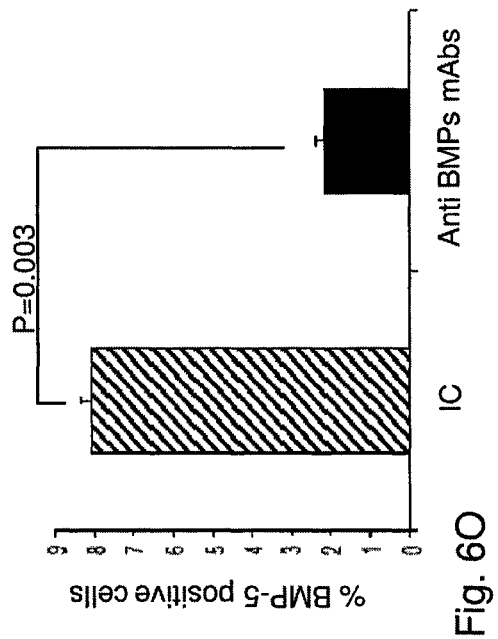
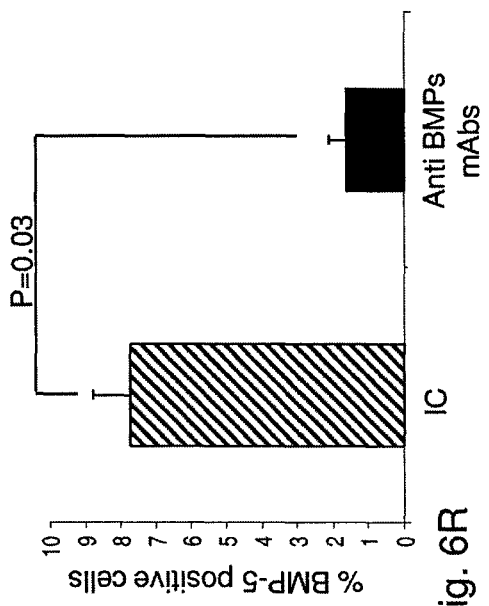
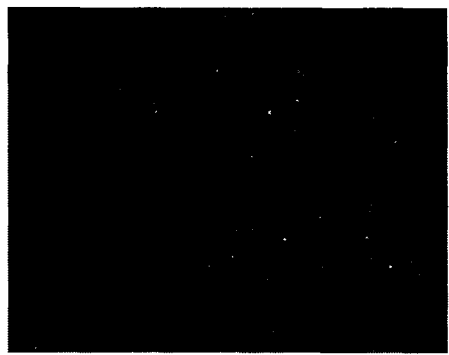
Fig. 6M  Fig. 6N  Fig. 6O
Fig. 6P  Fig. 6Q  Fig. 6R

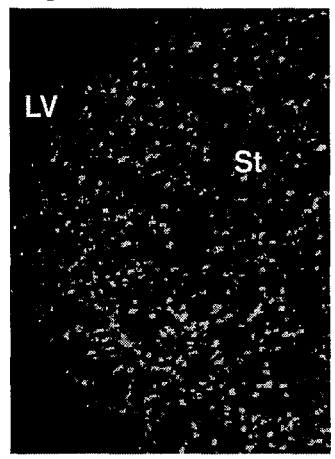
Fig. 7A1
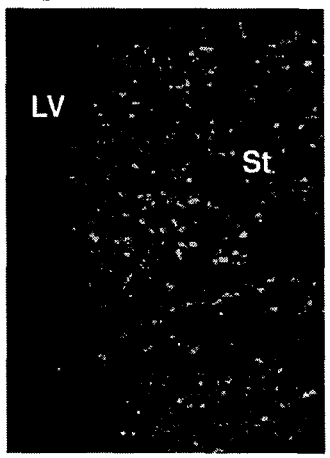
Fig. 7B1
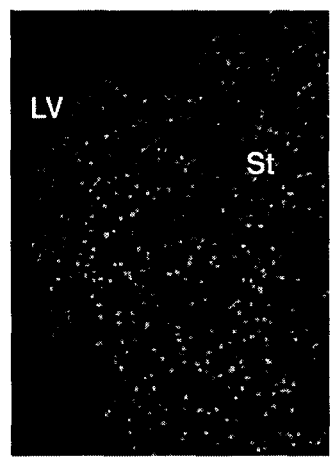
Fig. 7C1
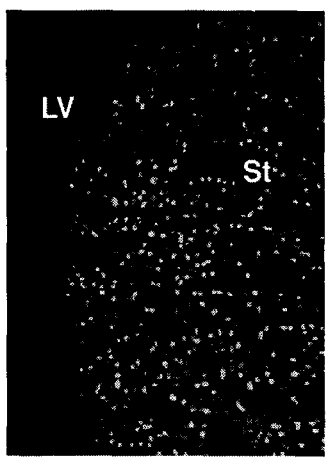
Fig. 7D1
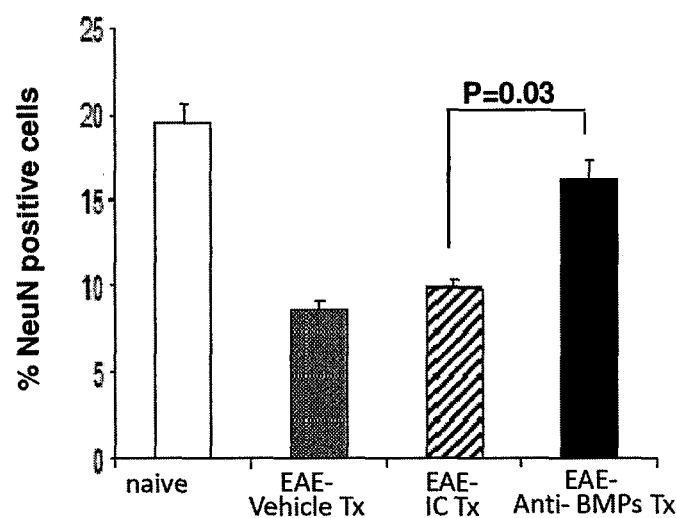
Fig. 7E1

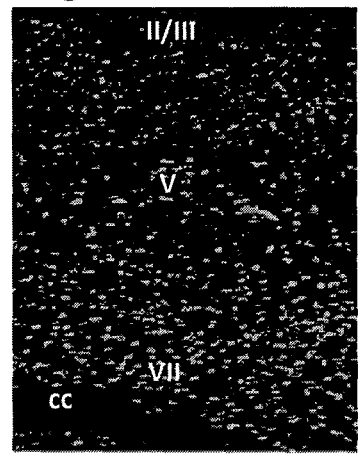
Fig. 7A2
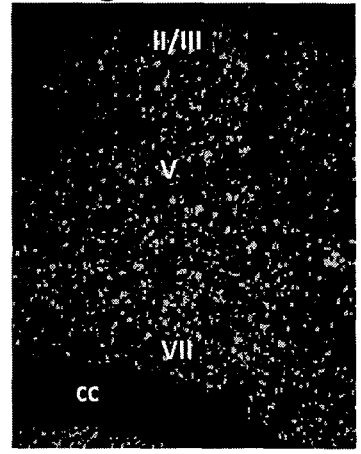
Fig. 7B2
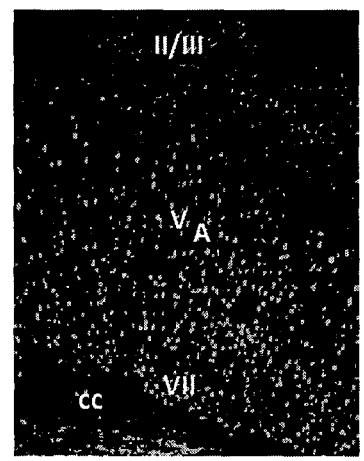
Fig. 7C2
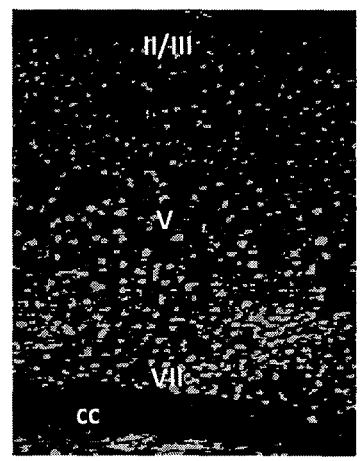
Fig. 7D2
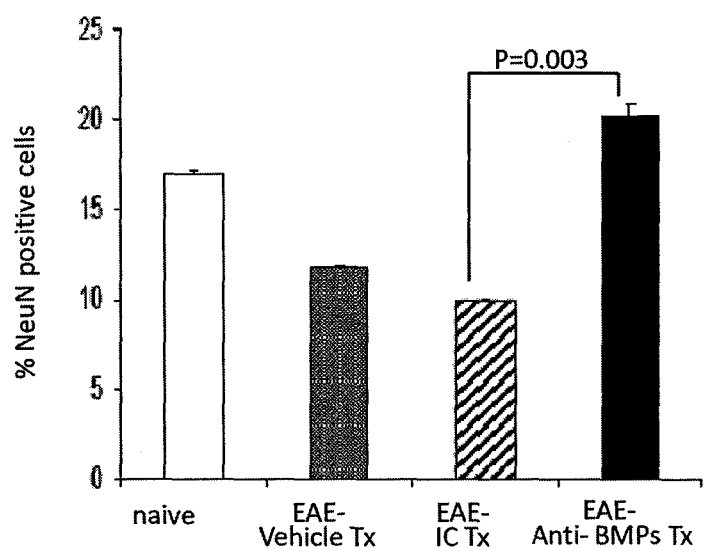
Fig. 7E2

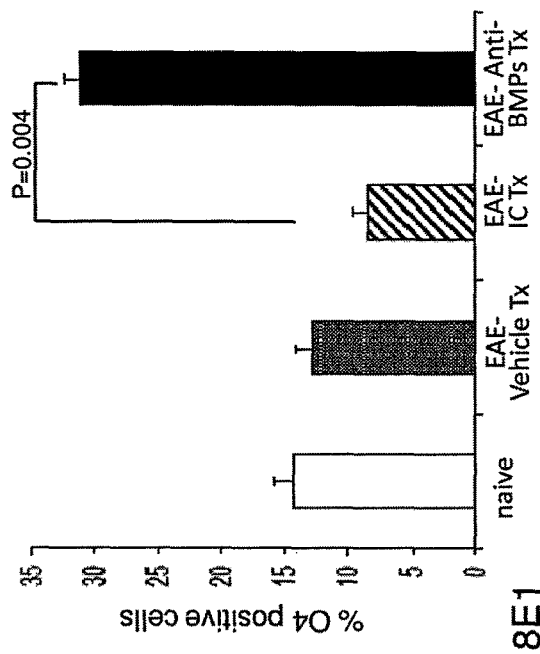
Fig. 8A1
Fig. 8B1
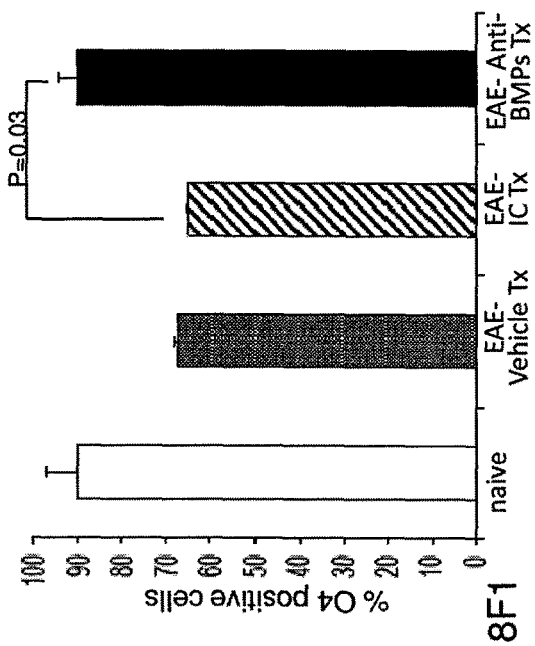
Fig. 8E1
Fig. 8F1
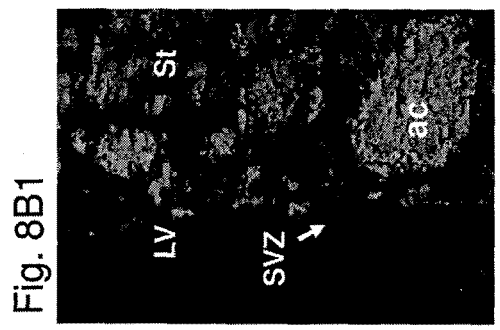
Fig. 8C1
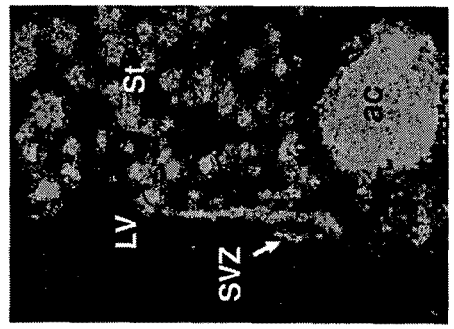
Fig. 8D1

Fig. 8A2
Fig. 8B2
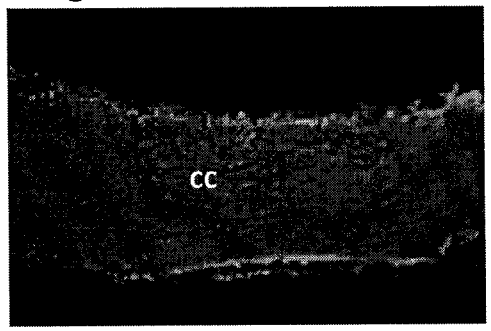
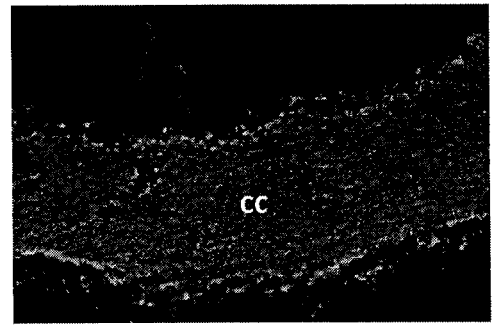
Fig. 8C2
Fig. 8D2
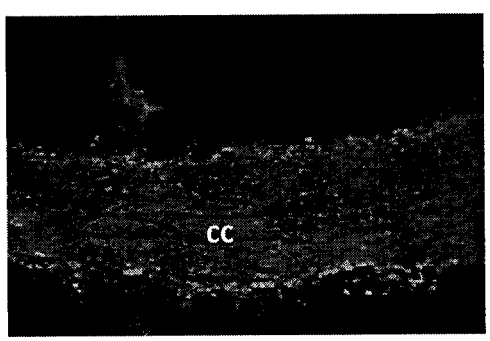
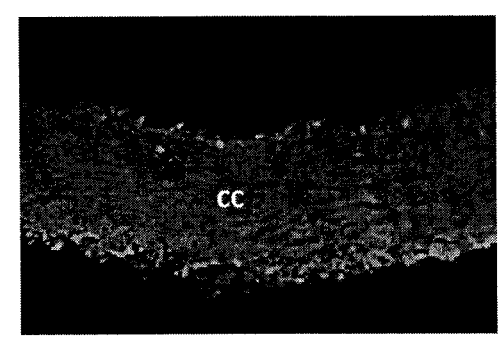
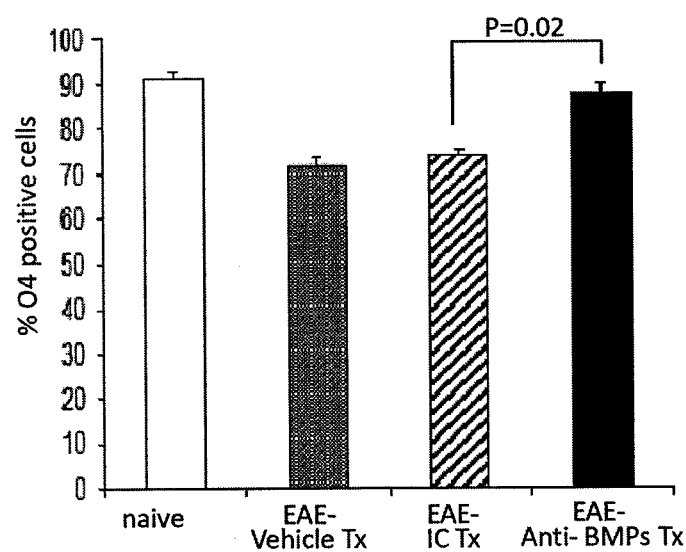
Fig. 8E2

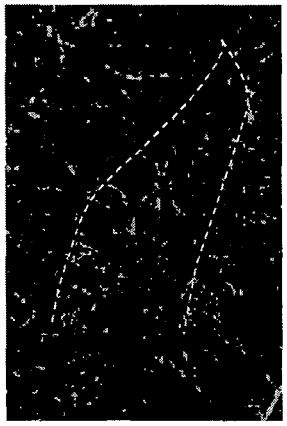 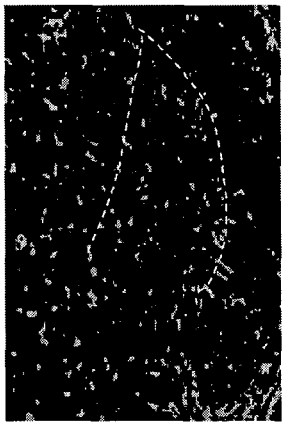 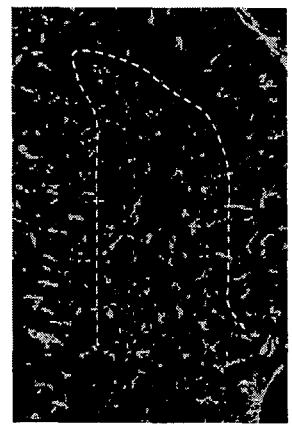
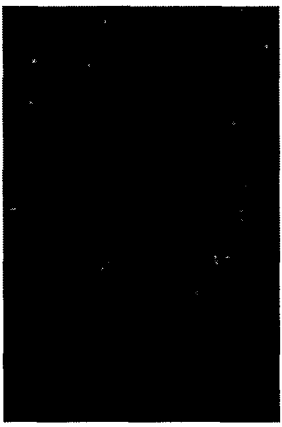  
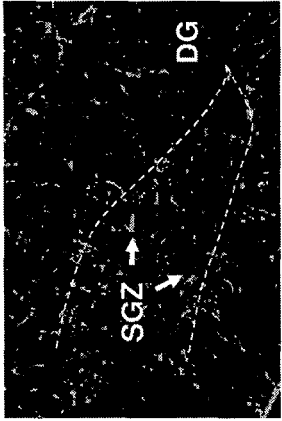 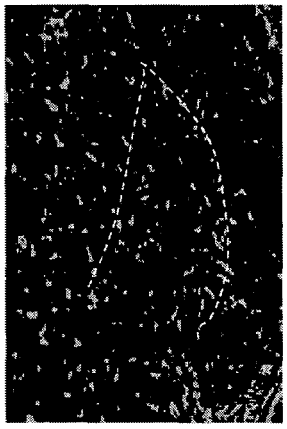 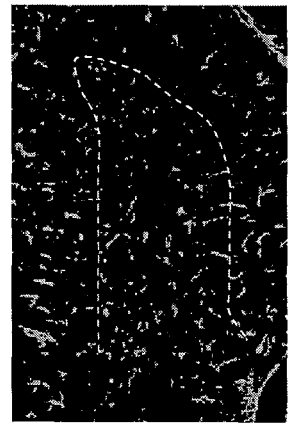
Fig. 9A  Fig. 9B  Fig. 9C

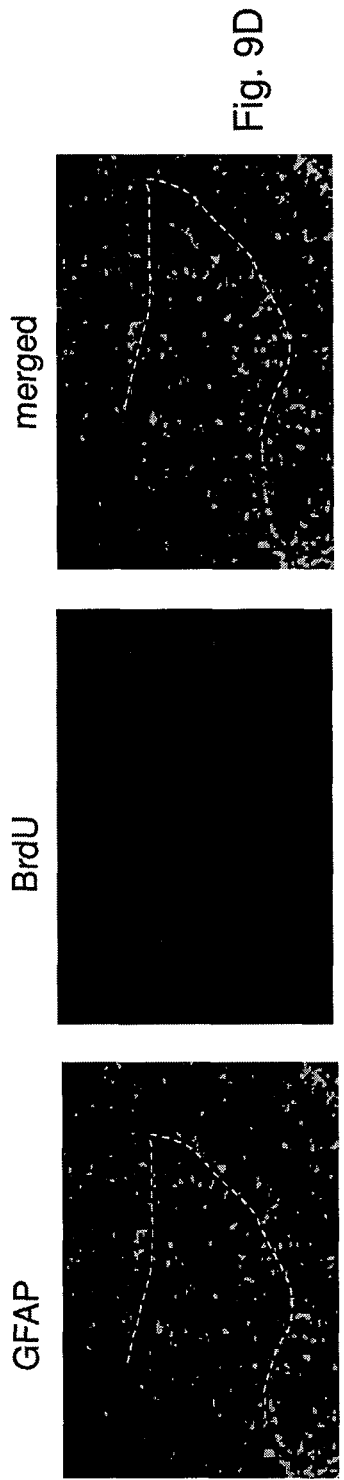
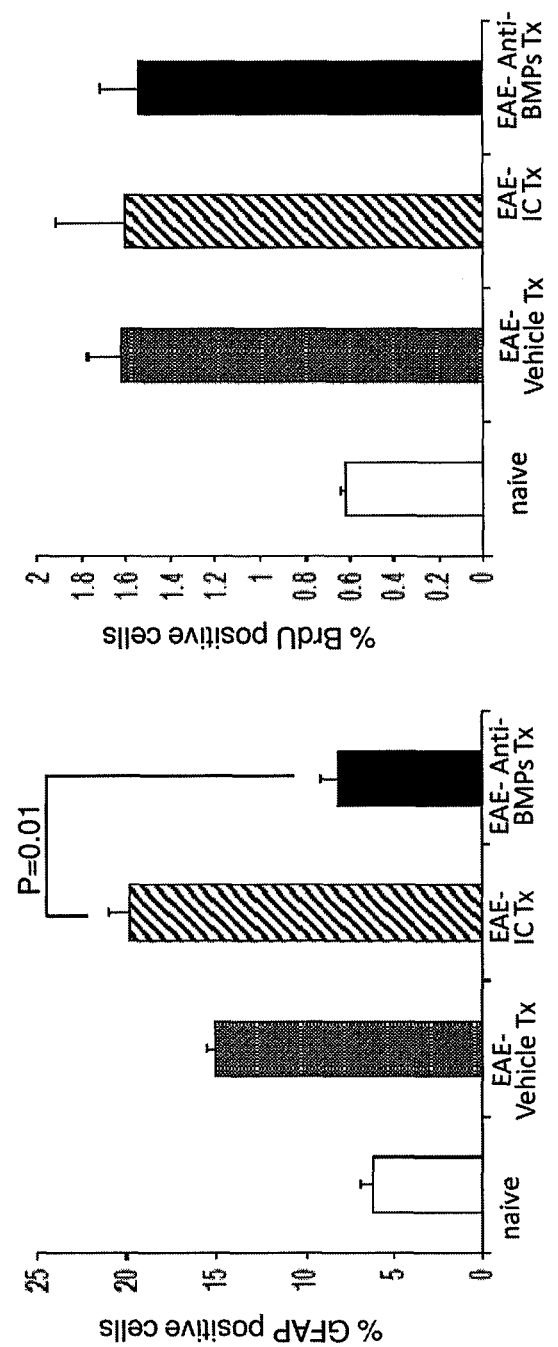
Fig. 9D
Fig. 9E
Fig. 9F

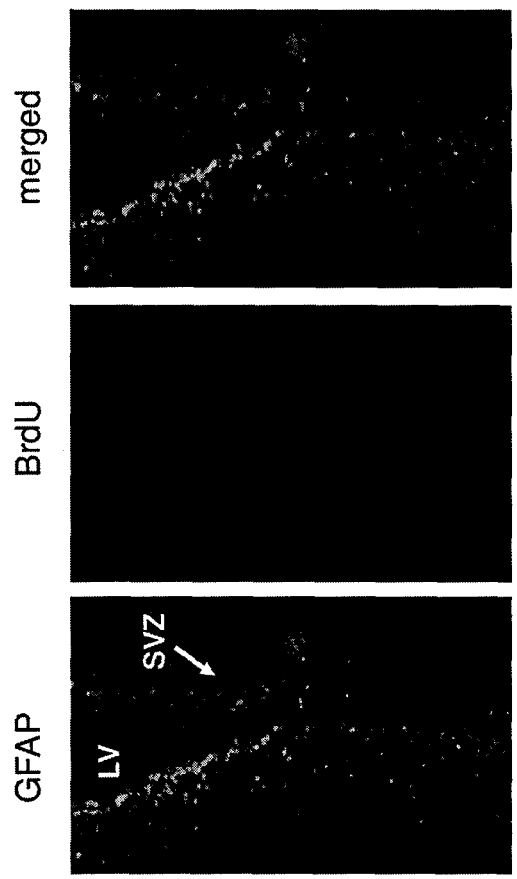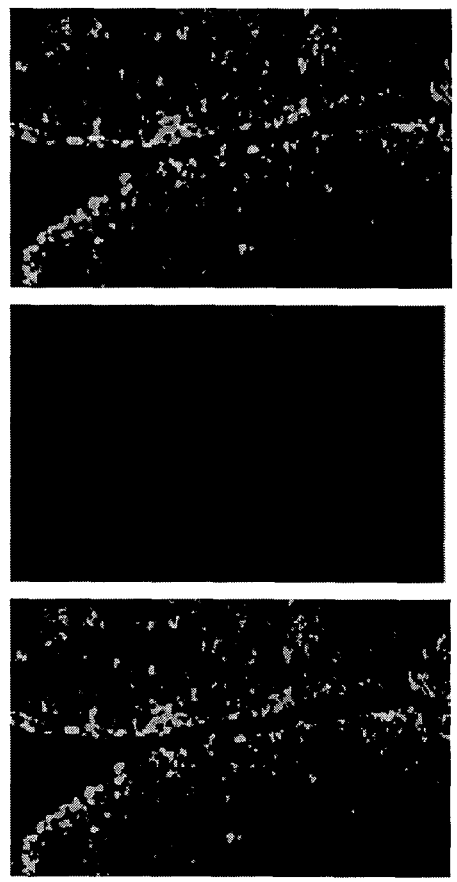

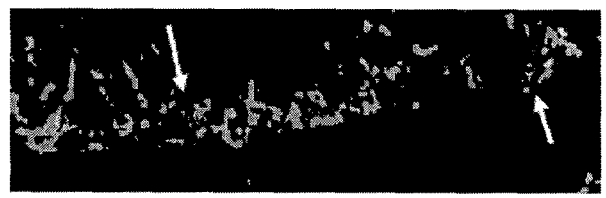
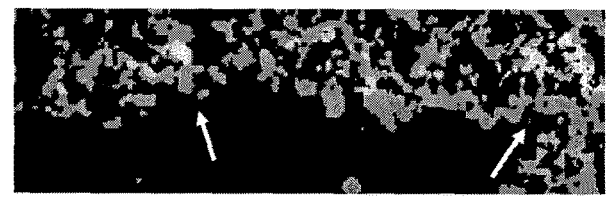
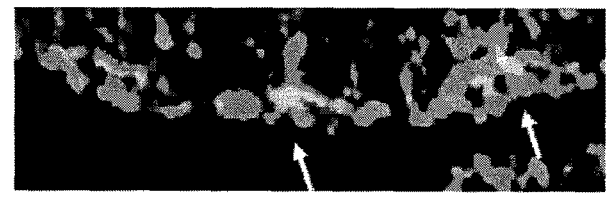
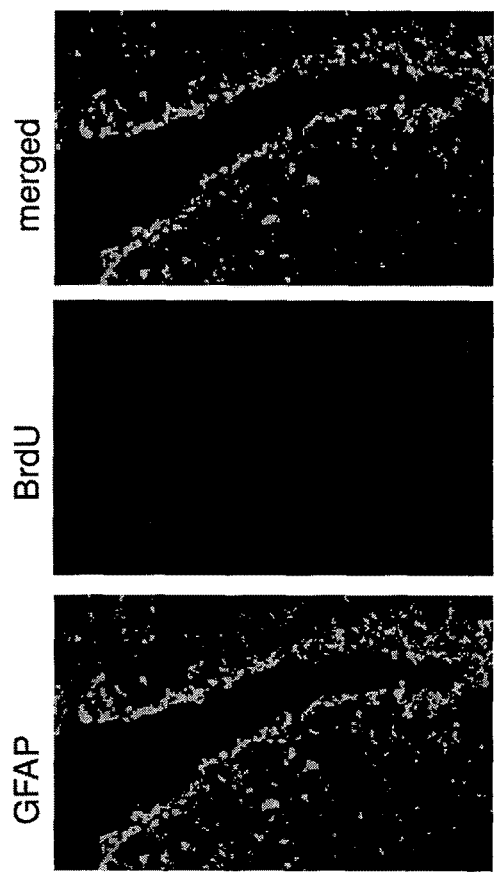
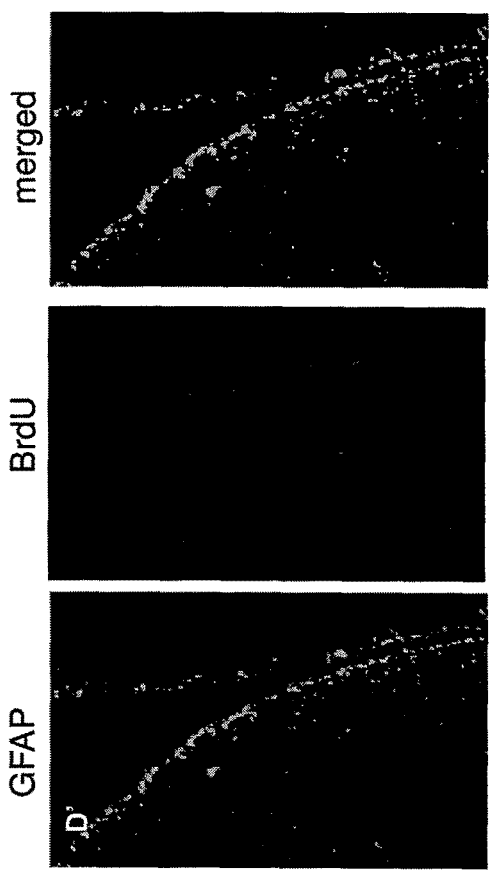

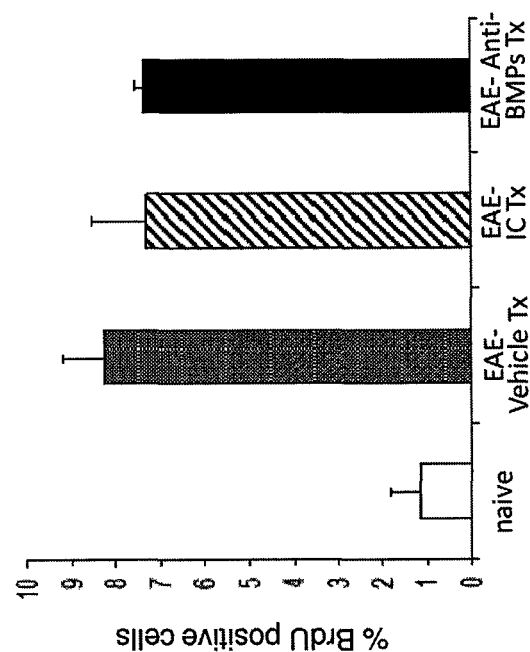
Fig. 9H1
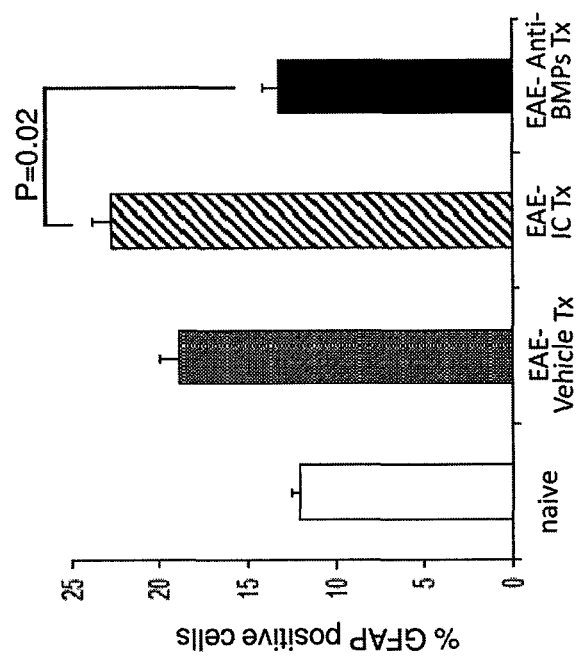
Fig. 9I1

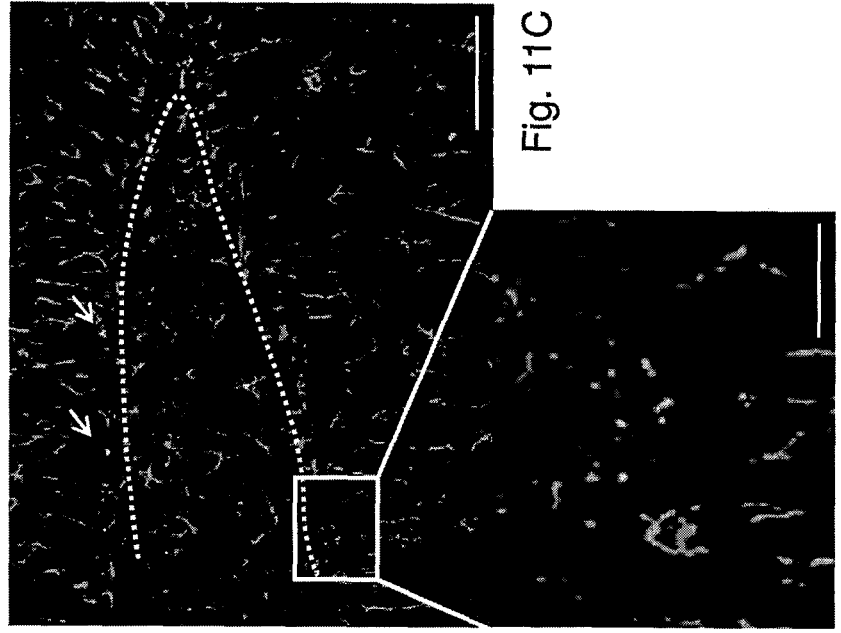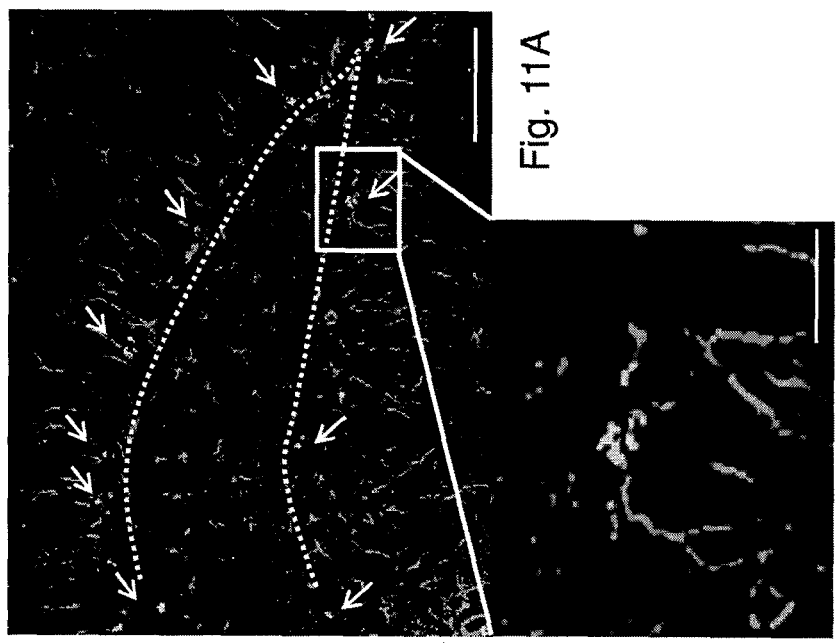

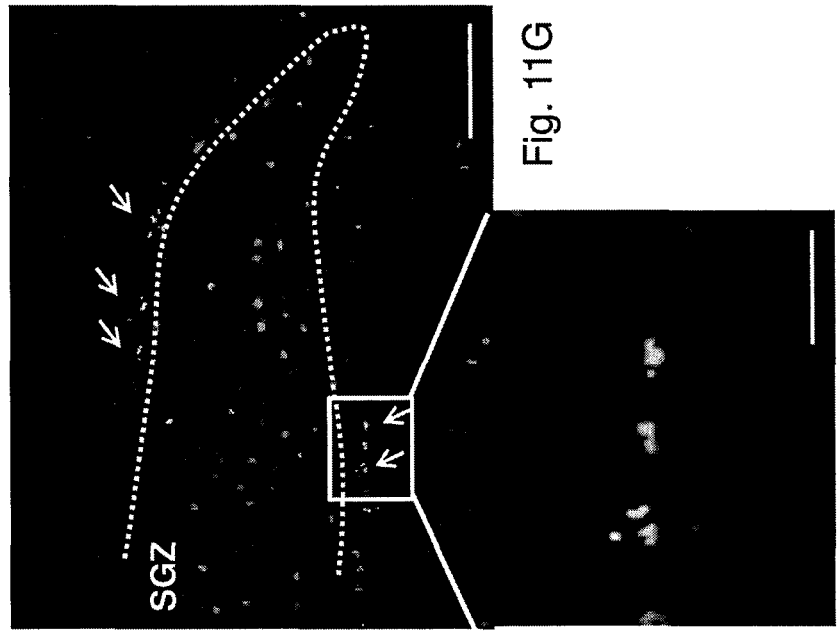
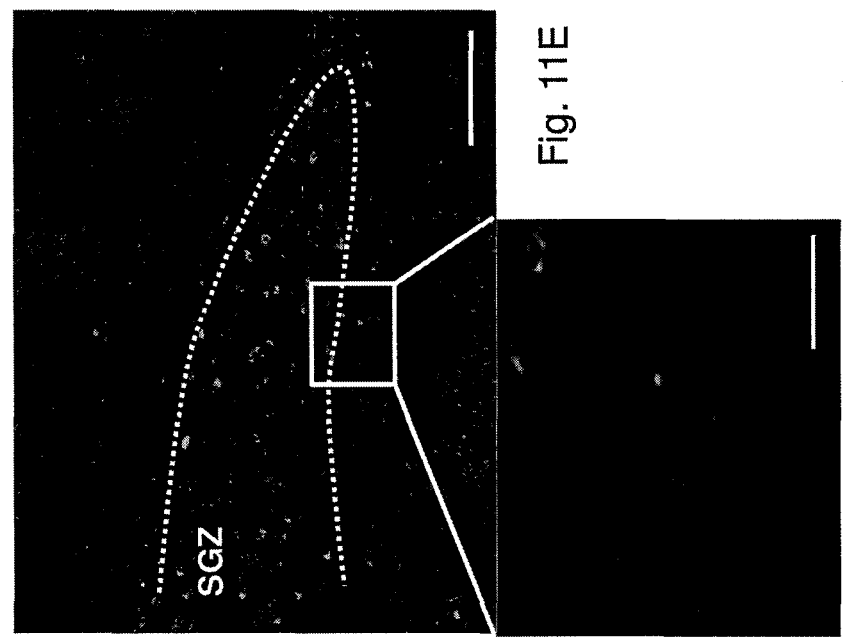

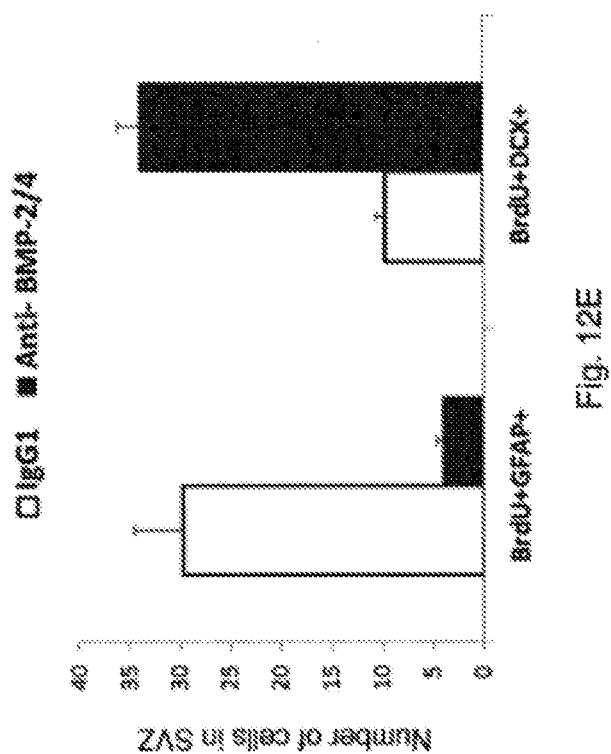
Fig. 12E
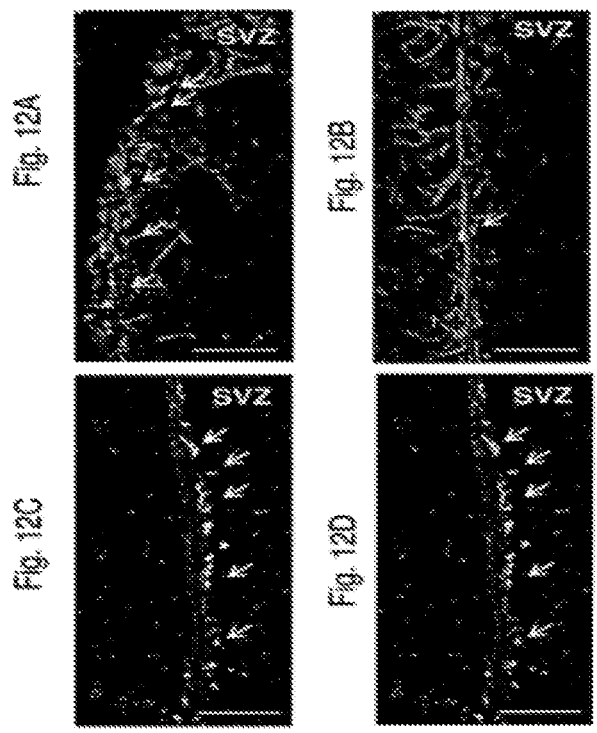

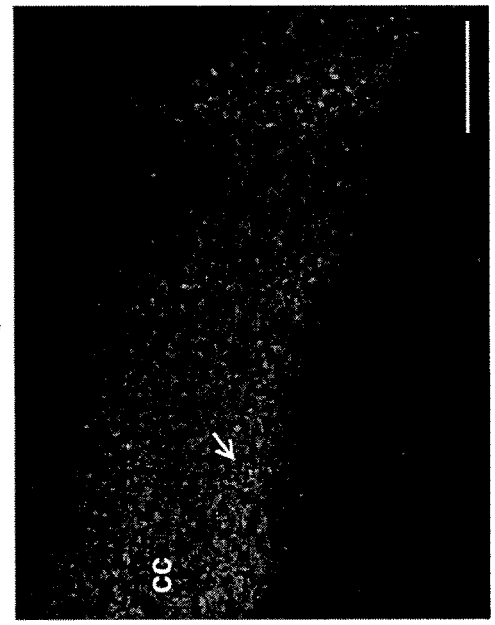
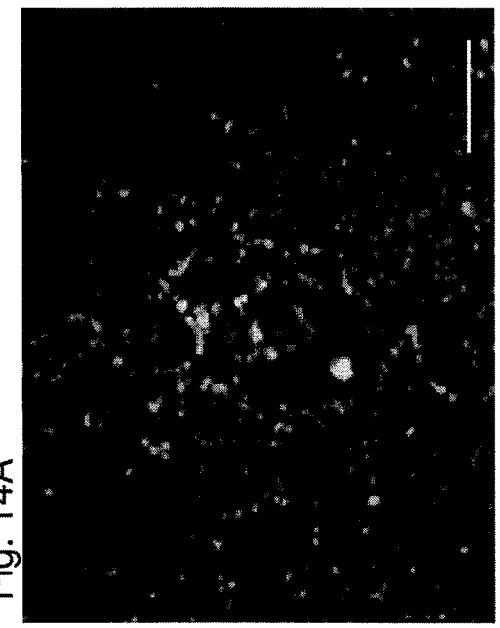
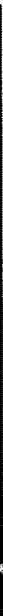
Fig. 14A
Fig. 14B
Fig. 14C
Fig. 14D

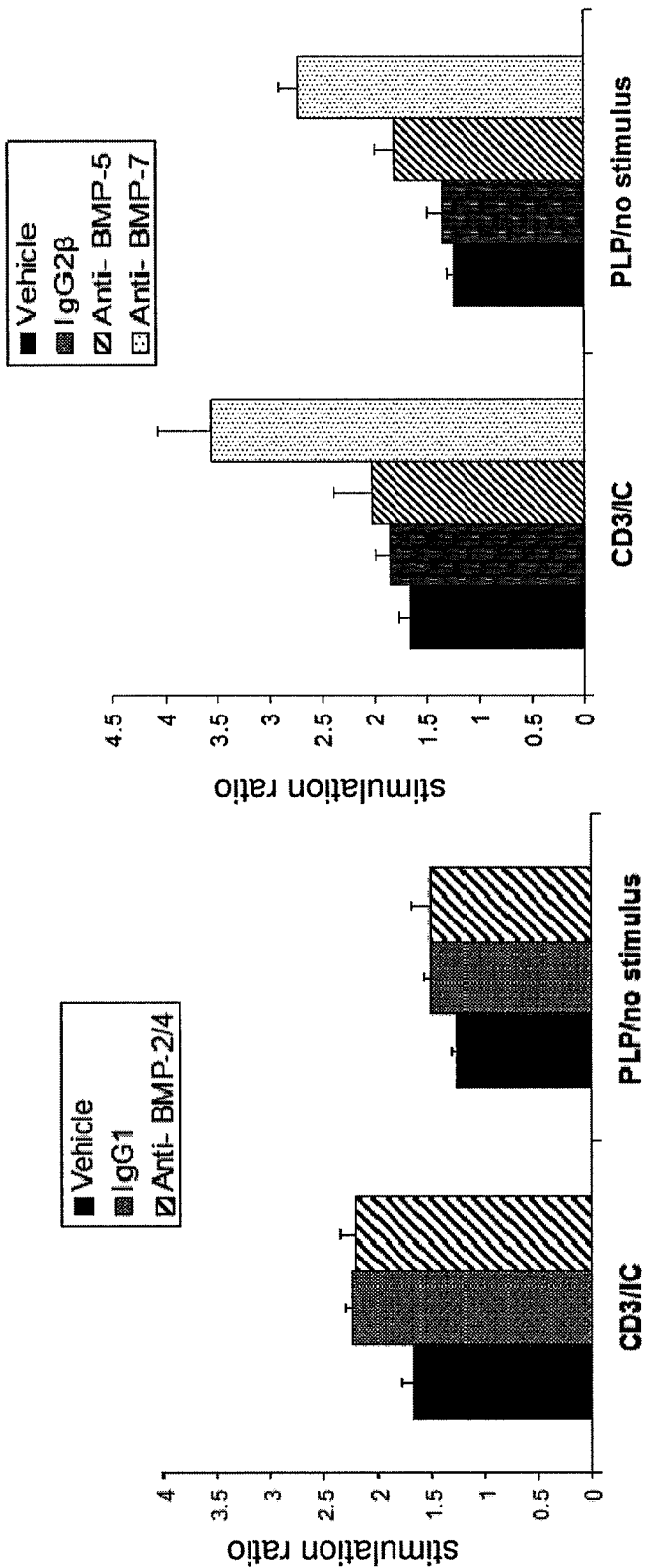

USE OF BLOCKING AGENTS OF BONE MORPHOGENIC PROTEIN (BMP) SIGNALLING FOR THE TREATMENT OF NEUROINFLAMMATORY AND NEURODEGENERATIVE DISEASES

TECHNOLOGICAL FIELD

This invention relates to pharmaceutical compositions for treating and/or ameliorating the symptoms of neuroinflammatory or neurodegenerative diseases, in particular multiple sclerosis.

PRIOR ART

References considered to be relevant as background to the presently disclosed subject matter are listed below:
[1] Trapp, B. D. and Nave, K. A. Annu. Rev. Neurosci. 2008; 31:247-269.
[2] Ferguson, B. et al., Brain 1997; 120:393-399.
[3] Snethen, H. et al., Regen. Med. 2008; 3:835-847.
[4] Kuhlmann, T. et al., Brain 2008; 131:1749-1758.
[5] Lim, D. A. et al., Neuron 2000; 28:713-726.
[6] Mabie, P. C. et al., J Neurosci. 1997; 17:4112-4120.
[7] Ara, J. et al., J Neurosci. Res. 2008; 86:125-135.
[8] Deininger, M. et al., Acta Neuropathol. 1995; 90:76-79.
[9] U.S. Pat. No. 7,803,752.
[10] Picard-Riera, N. et al., Proc. Natl. Acad. Sci. USA 2002; 99:13211-13216.
[11] Yu, P. B. et al., Nat. Chem. Biol. 2008; 4:33-41.
[12] Rosen, V. Ann, N. Y. Acad. Sci. 2006; 1068:19-25.
[13] Balemans, W. and Van Hul, W. Dev. Biol. 2002; 250:231-250.
[14] Yanagita, M. Cytokine Growth Factor Rev. 2005; 16:309-317.
[15] Abreu, J. G. et al., Nat. Cell. Biol. 2002; 4:599-604.
[16] Sharrack, B. et al. Brain 1999; 122:141-159.
[17] Kurtzke, J. F. Neurology 1983; 33(11):1444-1452.
[18] Kuhn, H. G. et al., J Neurosci. 1996; 16:2027-2033.
[19] Eto, R. et al., Int. J Dev. Neurosci. 2010; 28:359-370.
[20] Sasaki, R. et al., Neurosci. Lett. 2000; 279:57-60.

Acknowledgement of the above references herein is not to be inferred as meaning that these are in any way relevant to the patentability of the presently disclosed subject matter.

BACKGROUND

Multiple sclerosis (MS) is widely-recognized as a neuroinflammatory and neurodegenerative disease [1]. MS lesions are characterized by demyelination, oligodendrocyte death, axonal injury and neuronal loss [2]. Studies have shown that although neural stem cells (NSCs) are abundantly present in MS lesions [3] their differentiation into functional neurons and oligodendrocytes is mostly inconsistent, and many lesions fail to remyelinate successfully [4]. One of the factors known to affect NSCs differentiation is a group of proteins belonging to the transforming growth factor-β (TGFβ) family, named bone morphogenic proteins (BMPs).

Studies have shown that reduced BMP signaling is associated with both neurons [5] and oligodendrocytes [6] development. It has further been demonstrated that during experimental autoimmune encephalomyelitis (EAE), a mouse model for MS, BMPs-4, 6, and 7 are up-regulated in the mouse spinal cord [7]. In addition, PCR analysis of human MS plaques showed that MS lesions express both BMP-4 and BMP-5 mRNA [8].

It has also been demonstrated that BMP family members are expressed in the healthy adult brain, with differing distributions for various family members. Nevertheless, the specific expression profiles of BMP-2, 4, 5 and 7 in the neuroproliferative areas, namely, the subventricular zone (SVZ) and the subgranular zone (SGZ), have been poorly investigated.

U.S. Pat. No. 7,803,752 [9] discloses a method of inducing addition of medium spiny neurons comprising providing a neurotrophic factor and Noggin, an inhibitor of BMP. Specifically, U.S. Pat. No. 7,803,752 concern the treatment of Huntington's disease.

GENERAL DESCRIPTION

In one of its aspects the invention provides a pharmaceutical composition for the treatment of a neuroinflammatory disease, a neurodegenerative disease or nervous system damage comprising at least one blocking agent of Bone Morphogenic Protein (BMP) signaling and a pharmaceutically acceptable carrier.

In another aspect the invention provides a method of treatment of a subject suffering from a neuroinflammatory disease, a neurodegenerative disease or nervous system damage comprising administering to said subject a therapeutically effective amount of at least one blocking agent of Bone Morphogenic Protein (BMP) signaling and a pharmaceutically acceptable carrier.

The invention further provides use of at least one blocking agent of Bone Morphogenic Protein (BMP) signaling in the preparation of a pharmaceutical composition for the treatment of a subject suffering from a neuroinflammatory disease, a neurodegenerative disease or nervous system damage.

In some embodiments the blocking agent of Bone Morphogenic Protein (BMP) signaling according to the invention is an anti BMP antibody or functional fragments thereof.

In other embodiments the pharmaceutical composition according to the invention comprises at least two anti-Bone Morphogenic Protein antibodies or functional fragments thereof.

In further embodiments the method according to the invention comprises administering to said subject at least two anti-Bone Morphogenic Protein antibodies or functional fragments thereof.

In still further embodiments the at least two anti-Bone Morphogenic Protein antibodies are directed against different Bone Morphogenic Proteins and in other embodiments the use according to the invention is of at least two anti-Bone Morphogenic Protein antibodies, or functional fragments thereof, which are directed against different Bone Morphogenic Proteins.

In other embodiments the anti-Bone Morphogenic Protein antibodies are selected from the group consisting of anti-BMP-2, anti-BMP-4, anti-BMP-2/4, anti-BMP-5 and anti-BMP-7 antibodies or functional fragments thereof.

In further embodiments the pharmaceutical composition or use according to the invention comprises the anti-Bone Morphogenic Protein antibodies anti-BMP-2, anti-BMP-4, anti-BMP-2/4, anti-BMP-5 and anti-BMP-7 antibodies or functional fragments thereof.

In still further embodiments the method according to the invention comprises administering to said subject the anti-Bone Morphogenic Protein antibodies anti-BMP-2, anti-BMP-4, anti-BMP-2/4, anti-BMP-5, anti-BMP-7 antibodies or functional fragments thereof.

In some embodiments the pharmaceutical composition or use according to the invention comprises the anti-Bone Morphogenic Protein antibodies anti-BMP-2 and anti-BMP-4 or functional fragments thereof.

In other embodiments the method according to the invention comprises administering the anti-Bone Morphogenic Protein antibodies anti-BMP-2 and anti-BMP-4 or functional fragments thereof.

In some embodiments the pharmaceutical composition or use according to the invention comprise a single anti-Bone Morphogenic Proteins antibody selected from the group consisting of anti-BMP-2, anti-BMP-4, anti-BMP-2/4, anti-BMP-5, anti-BMP-7 antibodies and functional fragments thereof.

In other embodiments the method according to the invention comprises administering to said subject a single anti-Bone Morphogenic Protein antibody selected from the group consisting of anti-BMP-2, anti-BMP-4, anti-BMP-2/4, anti-BMP-5, anti-BMP-7 antibodies and functional fragments thereof.

In further embodiments the single anti-Bone Morphogenic Protein antibody is directed against BMP-2 and BMP-4.

In still further embodiments the anti-human Bone Morphogenic Protein antibodies according to the invention are monoclonal antibodies and in other embodiments the monoclonal antibodies are chimeric, humanized, or human antibodies.

In further embodiments the anti-Bone Morphogenic Protein antibodies according to the invention are directed against human BMP.

In yet further embodiments the at least one blocking agent of Bone Morphogenic Protein (BMP) signaling according to the invention is selected from the group consisting of dorsomorphin, LDN-193189, a BMP receptor antagonist, the protein complex Inhibin, BMP-3, Noggin, Chordin and Chordin-like molecules, Follistatin and Follistatin-related gene (FLRG), Ventroptin, twisted gastrulation (Tsg), Dan, Cerberus, Gremlin, Dante, caronte, Protein related to Dan and Cerberus (PRDC), Sclerostin and sclerostin-like, Coco, Cer1, Uterine sensitization-associated gene 1 (USAG-1) or connective tissue growth factor (CTGF), or any combination thereof.

In further embodiments the blocking agent of BMP signaling according to the invention is dorsomorphin.

In some embodiments the neuroinflammatory disease, neurodegenerative disease or nervous system damage according to the invention is selected from a group consisting of multiple sclerosis, Alzheimer's disease, Parkinson's Disease, Amyotrophic Lateral Sclerosis (ALS), neurosarcoidosis, CNS trauma, anoxic brain damage, CNS vasculitis, glioma and stroke.

In other embodiments the neuroinflammatory or neurodegenerative disease is multiple sclerosis.

In further embodiments the pharmaceutical composition according to the invention further comprises at least one additional therapeutic agent and in still further embodiments the pharmaceutical composition according to the invention is for use in combination with at least one additional therapeutic agent.

In other embodiments the method according to the invention further comprises administering to said patient at least one additional therapeutic agent.

In further embodiments the additional therapeutic agent according to the invention is an anti-inflammatory agent.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3: A graphical representations of the clinical effects of systemic treatment with anti-BMPs antibodies.

FIG. 7: Graphical representations of an increase in the levels of NeuN positive cells in neuroproliferative areas of RR-EAE mice in response to anti-BMPs mAbs treatment. FIGS. 7A, 7A1 and 7A2 show fluorescent micrographs of sections of the hippocampus, striatum and cortical layers, respectively, of age-matched SJL female naïve mice stained with anti-NeuN antibodies. Fluorescent micrographs stained with anti-NeuN antibodies of brain sections (as above) of age-matched vehicle-treated EAE mice are shown in FIGS. 7B, 7B1 and 7B2, of IC-treated EAE mice are shown in FIGS. 7C, 7C1 and 7C2 and of anti-BMPs mAbs treated EAE mice (30 μg/mouse, day 18 post-induction) are shown in FIGS. 7D, 7D1 and 7D2. Scale bar is 500 μm, except for FIGS. A1, B1 C1 and D1 (100 μm). FIGS. 7E, 7E1 and 7E2 show quantification of the percentage of NeuN positive cells, performed on the three brain sections (i.e. the hippocampus, striatum and cortical layers) obtained from three mice of each group, using ImageJ software. Abbreviations: CA3, cornu ammonis region 3; DG, dentate gyrus: St, striatum.

FIG. 8: Graphical representations of an increase in the levels of O4 positive cells in neuroproliferative areas of RR-EAE mice in response to anti-BMPs mAbs treatment. FIGS. 8A, 8A1 and 8A2 show fluorescent micrographs of sections of the brain regions hippocampus, lateral ventricle and corpus callosum of age-matched SJL female naïve mice stained with anti-O4 antibodies. Fluorescent micrographs of sections of the above indicated brain regions (respectively) of age-matched vehicle-treated EAE mice stained with anti-O4 antibodies are shown in FIGS. 8B, 8B 1 and 8B2, of IC-treated EAE mice are shown in FIGS. 8C, 8C and 8C2 and of anti-BMPs mAbs treated EAE mice (30 μg/mouse, day 18 post-induction) are shown in FIGS. 8D, 8D and 8D2. Scale bar is 500 μm. FIGS. 8E, 8E1 and 8E2 show quantification of the percentage of O4 positive cells, performed on three sections of hippocampus, lateral ventricle (SVZ) and corpus callosum, respectively, obtained from three mice of each group, using ImageJ software. FIG. 8F1 shows quantification of the percentage of O4 positive cells obtained for brain sections of the anterior commissure. Abbreviations: SVZ, subventricular zone; SGZ, subgranular zone; DG, dentate gyrus; LV, lateral ventricles; St, striatum; cc, corpus collasum.

FIG. 9 Graphical representation of the reduction in the number of GFAP positive cells in the SGZ and SVZ of anti-BMPs mAbs treated EAE mice. FIGS. 9A and 9A1 show fluorescent micrographs of sections of the subgranular zone (SGZ) and the subventricular zone (SVZ), respectively, of age-matched SJL female naïve mice stained with anti-GFAP and with anti-BrdU antibodies. Fluorescent micrographs of sections of the SGZ and the SVZ of vehicle-treated EAE mice are shown in FIGS. 9B and 9B1, respectively, of IC-treated EAE mice are shown in FIGS. 9C and 9C1, respectively, and of anti-BMPs mAbs treated EAE mice (30 μg/mouse, day 18 post induction) are shown in FIGS. 9D and 9D1, respectively. FIGS. 9E1, 9F1 and 9G1 represent are higher magnification of 9B (vehicle-treated EAE), 9C1 (IC-treated EAE) and 9D1 (anti-BMPs mAbs treated EAE), respectively. In FIGS. 9A, 9B, 9C and 9D, scale bar is 500 μm; in FIGS. 9A1, 9B1, 9C1 and 9D1, scale bar is 100 μm and in FIGS. 9E1, 9F1 and 9G1, scale bar is 25 μm. FIGS. 9E and 9H1 are quantifications of the percentage of GFAP positive cells in the tested groups, in the SGZ and in the SVZ, respectively, and FIGS. 9F and 9I1 are quantifications of the percentage of BrdU positive cells in the SGZ and in the SVZ, respectively. Abbreviations: SVZ, subventricular zone.

FIG. 10 Graphical representations of the clinical effects of systemic treatment with a single anti-BMP antibody.

FIG. 11: Graphical representations of a reduction in the numbers of $BrdU^+GFAP^+$ cells and an elevation in the numbers of $BrdU^+DCX^+$ in the SGZ in response to BMP-2/4 blockage. Immunohistochemical labeling of BrdU and GFAP in the SGZ of the hippocampus of EAE mice treated with IgG1 (30 μg/mouse) is shown in FIG. 11A and of EAE mice treated with anti-BMP-2/4 mAb (30 μg/mouse) is shown in FIG. 11C, on day 18 post immunization (scale bar=100 μm). Higher magnification of FIGS. 11A and 11C are shown in FIGS. 11B and 11D, respectively (scale bar=10 μm). Immunohistochemical labeling of BrdU and DCX in the SGZ of the hippocampus of IgG1-treated EAE mice is shown in FIG. 11E and of anti-BMP-2/4 mAb treated EAE mice is shown in FIG. 11G. Higher magnification of FIGS. 11E and 11G are shown in FIGS. 11F and 11H, respectively (scale bar=10 μm). Arrows indicate only double positive cells.

FIG. 12: Graphical representations of a reduction in the numbers of $BrdU^+GFAP^+$ cells and elevated numbers of $BrdU^+DCX^+$ in the SVZ of the lateral ventricle in response to BMP-2/4 blockage. Immunohistochemical labeling of BrdU and GFAP in the SVZ of the lateral ventricle of EAE mice treated with IgG1 (30 μg/mouse) is shown in FIG. 12A and of EAE mice treated with anti-BMP-2/4 mAb (30 μg/mouse) is shown in FIG. 12B, on day 18 post immunization (scale bar=100 μm). Immunohistochemical labeling of BrdU and DCX in the SVZ of the lateral ventricle of IgG1-treated EAE mice is shown in FIG. 12C and of anti-BMP-2/4 mAb treated EAE mice is shown in FIG. 12D (scale bar=100 μm). Arrows indicate only double positive cells. A graphical representation of quantification of the results presented in FIGS. 12A-D is shown in FIG. 12E. Quantification was performed by analyzing 3 sections from each mouse, 3 mice from each group, total N=9 (FIG. 12E). Coronal sections, images were obtained by a confocal microscopy. Abbreviations: SVZ, subventricular zone.

FIG. 14: Graphical representations of an elevation in the numbers of BrdU$^+$O4$^+$ cells in corpus callosum and in hippocampal lesion of anti-BMP-2/4 mAb treated mice. Immunohistochemical labeling of BrdU and O4 in corpus callosum of EAE mice treated with IgG1 (30 μg/mouse) on day 18 post immunization is shown in FIG. 14A. De novo BrdU$^+$O4$^+$ cells were detected in the corpus callosum of EAE mice treated with anti-BMP-2/4 mAb (30 μg/mouse) by immunohistochemical labeling as indicated above and are shown in FIG. 14B (scale bar=100 μm, Arrows indicate only double positive cells). Analysis of a representative hippocampal lesion obtained from the anti-BMP-2/4 group revealing that most of the BrdU$^+$ cells in the lesion of anti-BMP-2/4 group were also positive to O4 is shown in FIG. 14D. A respective analysis of the IgG1 group revealing that most of the BrdU$^+$ cells in a hippocampal lesion of IgG1 group were negative to O4 is shown in FIG. 14C (scale bar=20 μm).

FIG. 15: Graphical representation of lack of suppression of T cells responses in anti-BMPs mAbs treated RR-EAE mice.

DETAILED DESCRIPTION OF EMBODIMENTS

Figure 1:
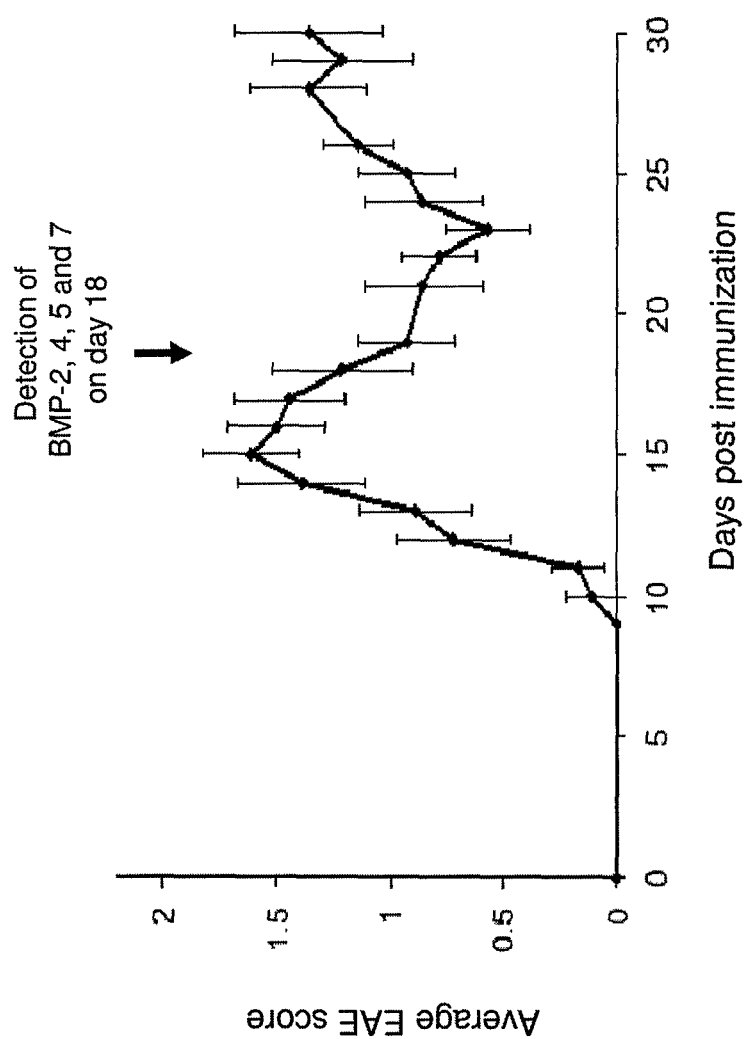
FIG. 1: A graphical representation of the change of the average EAE score of RR-EAE mice post induction of RR-EAE. Abbreviations: EAE, Experimental autoimmune encephalomyelitis.

The present invention is based on the finding that obstruction of bone morphogenic protein (BMP) signaling, using anti BMP-2/4, 5 and 7 monoclonal antibodies (mAbs), or other antagonists or blocking agents of BMP signaling (e.g. dorsomorphin) results in improving the clinical outcome in a relapsing/remitting experimental autoimmune encephalomyelitis (RR-EAE) animal model, a well-established model mimicking multiple sclerosis (MS). The effect of anti BMP-2/4, 5 and 7 monoclonal antibodies was also demonstrated in a mice model mimicking the chronic (or progressive) form of the disease.

Without wishing to be bound by theory and as shown by the Examples below, the effect of the anti BMP antibodies is mediated by induction of neurogenesis, rather than inhibition of the inflammatory process associated with the disease.

The invention therefore provides pharmaceutical compositions for the treatment of neuroinflammatory or neurodegenerative diseases or conditions associated with nervous system, in particular CNS, damage comprising a single blocking agent of Bone Morphogenic Protein (BMP) signaling, or a combination of several blocking agents of Bone Morphogenic Protein (BMP) signaling. The pharmaceutical compositions may further comprise additional therapeutic agents or may be administered in combination with additional therapeutic agents. The invention further provides methods of treatment of neuroinflammatory or neurodegenerative diseases or conditions associated with nervous system, in particular CNS, damage comprising administering to a patient in need thereof the pharmaceutical compositions of the invention.

Thus, in a first of its aspects the present invention provides a pharmaceutical composition for the treatment of a neuroinflammatory disease, a neurodegenerative disease or nervous system, in particular CNS, damage comprising at least one blocking agent of Bone Morphogenic Protein (BMP) signaling and a pharmaceutically acceptable carrier.

The term "Bone morphogenetic protein (or proteins)" (BMPs) as herein defined refers to a group of growth factors also known as cytokines or metabologens. BMPs induce the formation of bone and cartilage, and have multiple roles in embryonic brain development. Twenty BMPs have been discovered to date, of these, six BMPs (i.e. BMP-2 through BMP-7) belong to the Transforming growth factor 0 (beta) super family of proteins. In particular, the present invention concerns BMPs that are associated with neuronal proliferation and development. Non-limiting examples include BMPs 2, 4, 5, 6, and 7. In a specific embodiment the BMP is human BMP.

"Bone morphogenetic protein 2" (or BMP-2), as other bone morphogenetic proteins, plays an important role in the development of bone and cartilage. It is involved in the hedgehog pathway, TGF β signaling pathway, and in cytokine-cytokine receptor interaction. It is involved also in cardiac cell differentiation and epithelial to mesenchymal transition. BMP-2 acts as a disulfide-linked homodimer and was shown to stimulate the production of bone. Recombinant human protein (rhBMP-2) is currently available for orthopaedic usage in the United States. Implantation of BMP-2 in a collagen sponge induces new bone formation and can be used for the treatment of bony defects, delayed union, and non-union.

In some embodiments, the Bone morphogenetic protein 2 according to the invention is human BMP-2, having the accession number NM_001200.2.

"Bone morphogenetic protein 4" (or BMP-4), is also involved in bone and cartilage development, specifically tooth and limb development and fracture repair. This particular family member plays an important role in the onset of endochondral bone formation in humans. It has been shown to be involved in muscle development, bone mineralization, and ureteric bud development. In human embryonic development, BMP-4 is a critical signaling molecule required for the early differentiation of the embryo and establishing of a dorsal-ventral axis. BMP-4 is secreted from the dorsal portion of the notochord, and it acts in concert with sonic hedgehog (released from the ventral portion of the notochord) to establish a dorsal-ventral axis for the differentiation of later structures.

In other embodiments, the Bone morphogenetic protein 4 according to the invention is human BMP-4, having the accession number P12644.

"Bone morphogenetic protein 5" (or BMP-5) is another member of the transforming growth factor-beta (β) superfamily. This protein may act as an important signaling molecule within the trabecular meshwork and optic nerve head, and may play a potential role in glaucoma pathogenesis. The gene encoding this protein is differentially regulated during the formation of various tumors.

In further embodiments, the Bone morphogenetic protein 5 according to the invention is human BMP-5, having the accession number P22003.

"Bone morphogenetic protein 7" (or BMP-7, also known as osteogenic protein-1 or OP-1) is a protein that in humans is encoded by the BMP7 gene. BMP-7 is also a member of the TGF-β superfamily. Like other members of the bone morphogenetic protein family of proteins, it plays a key role in the transformation of mesenchymal cells into bone and cartilage. It is inhibited by noggin and a similar protein, chordin, which are expressed in the Spemann-Mangold Organizer. BMP-7 may be involved in bone homeostasis. It is expressed in the brain, kidneys and bladder.

In yet further embodiments, the Bone morphogenetic protein 7 according to the invention is human BMP-7, having the accession number P18075.

BMPs interact with specific receptors on the cell surface, referred to as bone morphogenic protein receptors (BMPRs). Signal transduction through BMPRs results in mobilization of members of the SMAD family of proteins. As used herein the term "BMP signaling" refers to the signaling pathway initiated by binding of a BMP to its receptor and the subsequent cellular processes induced by this binding e.g. mobilization of members of the DMAD family of proteins.

The term "blocking agent of Bone Morphogenic Protein (BMP) signaling" as herein defined is used in the broadest sense and refers to any molecule which may inhibit BMP signaling. The molecule may be directed against the BMP molecule. By way of example, the blocking agent according to the invention may be an antibody that directly interacts with a specific BMP. The blocking agent of BMP signaling may also be a molecule which blocks the BMP receptor, e.g. dorsomorphin. In a specific embodiment the blocking agent is capable of blocking human BMP.

The term "neurodegenerative disease" as herein defined is the progressive loss of structure or function of neurons, including death of neurons, in the brain or spinal cord. A neurodegenerative disease according to the invention may be, but is not limited to Alzheimer's disease (AD), Parkinson's disease (PD) and Amyotrophic Lateral Sclerosis (ALS, also termed Lou Gehrig's disease) and Multiple Sclerosis (MS).

The term "Neuroinflammatory disease" as herein defined relates to an inflammatory disease in the central nervous system (CNS, brain, and spinal cord) including but not limited to, multiple sclerosis (MS), in which immune cells attack a component in the CNS and is also defined herein as a neurodegenerative disease, Acute disseminating encephalomyelitis (ADEM), Neuromyelitis (Devic's disease), neuro-sarcoidosis and neurological manifestations of systemic inflammatory (rheumatological) diseases, lupus cerebritis, Sjogren disease, primary vaculitis (angiitis) of the CNS, or CNS vaculitis secondary to systemic vascultis such as polyartritis nodosa, Wegener's disease, Behcet's disease, Neuro-Lyme disease, Post-streptococcal, e.g. Sydenham chorea, Paediatric autoimmune neurological disease associated with streptococcal infection (PANDAS), and Paraneuplastic syndromes of the CNS.

The present invention also pertains to the treatment of nervous system damage, in particular to damage in the central nervous system. Adult mammalian central nervous system neurons do not re-grow functional axons after damage. As a result, injury to the adult central nervous system (CNS) is devastating because of the inability of central neurons to regenerate correct axonal and dendritic connections. The consequences of injury are not just a break in communication between healthy neurons, but a cascade of events that can lead to neuronal degeneration and cell death. As used herein the term "Central nervous system (CNS) damage" relates to conditions affecting the central nervous system, e.g. the spinal cord and the brain, including but not limited to stroke, trauma and anoxia. Damage to the CNS may also be a result of glioma. Thus, in some embodiments the neuroinflammatory disease, neurodegenerative disease or CNS damage according to the invention is selected from a group consisting of multiple sclerosis, Alzheimer's disease, Parkinson's Disease, Amyotrophic Lateral Sclerosis (ALS), neurosarcoidosis, CNS trauma, anoxic brain damage, CNS vasculitis glioma and stroke.

As shown in the Examples below (e.g. Examples 2 and 3), administration of monoclonal antibodies directed against BMP-2, 4, 5 and 7 ameliorated the clinical symptoms in a relapsing/remitting experimental autoimmune encephalomyelitis (RR-EAE) animal model, a well-established model mimicking multiple sclerosis (MS). The effect of the anti BMP-2/4, 5 and 7 monoclonal antibodies was also demonstrated in a mice model mimicking the chronic (or progressive) form of the disease.

Thus, in some embodiments the blocking agent of Bone Morphogenic Protein (BMP) signaling according to the invention is an anti human BMP antibody, i.e. the invention provides a pharmaceutical composition comprising an anti human BMP antibody or functional fragments thereof. In a specific embodiment, the invention provides a pharmaceutical composition comprising anti human BMP antibodies or functional fragments thereof for the treatment of Multiple sclerosis.

The term "antibody (or antibodies)", also known as an "immunoglobulin" (Ig), as herein defined is used in the broadest sense and includes monoclonal antibodies, polyclonal antibodies, multivalent antibodies, multispecific antibodies (e.g. bispecific antibodies) and affinity-purified polyclonal antibodies. The antibodies may be full length antibodies (e.g. intact) or functional fragments thereof which retain the antigen-binding activity of the antibodies (e.g. F(ab')2 and Fab proteolytic fragments). The antibody according to the invention may also be a genetically engineered intact antibody or a fragment thereof, such as a chimeric antibody, Fv fragments, single chain antibodies and the like, as well as synthetic antigen-binding peptides and polypeptides. The antibody according to the invention may be non human, humanized, or human.

The term "antibody" or "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" (CDR) and/or those residues from a "hypervariable loop". The CDR's are primarily responsible for binding to an epitope of an antigen. "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin.

The Examples below demonstrate a beneficial therapeutic effect obtained with a monoclonal antibody directed against BMP-2/4 (Example 8) or with a monoclonal antibody directed against BMP-2/4 in combination with other monoclonal antibodies, the latter directed against BMP-5 and BMP-7 (e.g. Example 2, Example 3).

Thus, by a non-limiting example, the antibodies according to the invention may be monoclonal antibodies. The term "monoclonal antibody (or antibodies)" as used herein refers to a population of substantially homogenous antibodies, i.e., the individual antibodies comprising the population are identical except for possibly naturally occurring mutations that may be present in minor amounts. Monoclonal antibodies are directed against a single antigenic site (epitope).

As known in the art, the term "antigen" refers to a predetermined antigen to which an antibody can selectively bind. For example, the target antigen may be a polypeptide. The term "epitope" refers to the portion of the antigen to which the antibody selectively binds.

Monoclonal antibodies may be obtained by any technique known to those skilled in the art. As a non-limiting example, monoclonal antibodies may be obtained using the hybridoma method first described by Kohler et al. (Nature 256:495-497 (1975)) or may be made by recombinant DNA methods. As a non-limiting example, monoclonal antibodies may be prepared from B cells taken from the spleen or lymph nodes of immunized animals, in particular rats or mice, by fusion with immortalized B cells under conditions which favor the growth of hybrid cells.

Therefore, in some embodiments there is provided a pharmaceutical composition for the treatment of a neuroinflammatory disease, a neurodegenerative disease or CNS damage comprising at least one monoclonal anti-Bone Morphogenic Protein (BMP) antibody, or fragments thereof and a pharmaceutically acceptable carrier.

By a further non-limiting example, the antibodies according to the invention may be polyclonal antibodies. As used herein the term "polyclonal antibody (or antibodies)" refers to a population of different antibodies directed against different determinants (epitopes) of the same antigen.

Polyclonal antibodies may be prepared by any technique known to those skilled in the art. For example, polyclonal antibodies may be raised in animals, by multiple subcutaneous or intraperitoneal injections of the relevant BMP antigen, or a fragment thereof, and an adjuvant. One month later, the animals are boosted with an additional injection of the relevant BMP antigen, or fragment thereof, in Freund's complete adjuvant, by subcutaneous injections at multiple sites. The animal's serum is assayed for antibody titer seven to 14 days later and the animals are boosted repeatedly, until the titer (how much antibody an organism has produced that recognizes a particular epitope) of antibodies plateaus.

Polyclonal antibodies may be purified by any method known to a person skilled in the art. For example, polyclonal antibodies may be affinity purified, i.e. the antibodies may be loaded onto a chromatographic column to which the antigen (or the epitope, e.g. the relevant BMP antigen) has been previously conjugated. Antibodies that specifically bind the antigen (or the epitope) will be retained on the column and may be thereafter dissociated from the column by any method known in the art.

By another non-limiting example, the antibodies according to the invention may be multivalent. The term "multivalent antibody (or antibodies)" as herein defined refers to antibodies having several sites of attachment for an antigen. By way of non-limiting example, a multivalent antibody may be a bispecific antibody, i.e. an antibody having two sites of attachment for two different antigens.

In specific embodiments the antibody according to the invention is thus a bispecific antibody.

The term "functional fragments" refers to antibody fragments having the same measurable biological activity as the anti BMP antibody. Measuring the biological activity may be performed by measuring of the binding specificity of the antibody fragments, for example, by immunoprecipitation or by an in vitro binding assay, such as radioimmunoassay (RIA) or enzyme-linked immunoabsorbent assay (ELISA). Measuring the biological activity may also be performed in vivo for example, by assessment of measurable clinical symptoms such as tail or limb weakness or paralysis in an EAE-RR animal model, or assessment of cell markers, such as NeuN or O4 induction, or GFAP reduction.

Antibody fragments comprise a portion of a full length antibody, preferably comprising the antigen-binding or variable region thereof. Examples of antibody fragments include Fab, Fab', F(ab')$_2$, and Fv fragments; diabodies, linear antibodies and single-chain antibody molecules.

The term a "Fab fragment" as herein defined is a region on an antibody that binds to antigens. It is composed of one constant and one variable domain of each of the heavy and the light chain. The term a "Fab' fragment" as herein defined contains one light chain and one heavy chain that contains more of the constant region (with respect to the Fab fragment), such that an interchain disulfide bond can be formed between two heavy chains to form a F(ab')$_2$ molecule. The term a "F(ab')$_2$ fragment" as herein defined contains two light chains and two heavy chains containing a portion of the constant region, such that an inter-chain disulfide bond is formed between two heavy chains.

In some embodiments the antibodies according to the invention are neutralizing antibodies. The term "neutralizing antibody" as herein defined refers to an antibody, which inhibits or reduces the biological activity of the antigen it binds, namely, a bone morphogenic protein (BMP), for example, by binding to an active site on a BMP, by inhibiting interaction between a BMP and another molecule (e.g. a BMP receptor or any other molecule that associates with a BMP) or by any other way, thereby the signaling activity of a BMP is reduced, interrupted, obstructed or blocked.

As shown in Example 2 below, systemic administration of a combination of antibodies directed against BMP 2, 4, 5 and 7 ameliorated the clinical symptoms of RR-EAE mice. Interestingly, the inventors have also demonstrated that a monoclonal antibody directed against both BMP-2 and BMP-4 (referred to herein as "anti-BMP-2/4 mAb") was effective in ameliorating the clinical symptoms of RR-EAE. The effect of this antibody was also demonstrated at a cellular level (Examples 9-11), showing, for example, that an increased number of neuroblasts was found in the neuroproliferative niches of RR-EAE in response to blockage of BMP-2/4 signaling.

Thus, in some embodiments, the pharmaceutical composition according to the invention comprises at least one, at least two, or at least three anti-Bone Morphogenic Protein antibodies or functional fragments thereof.

The terms "at least two or at least three anti-Bone Morphogenic Protein antibodies" means that the at least two or three antibodies may be directed to the same BMP (it is noted that the antibodies may differ by their target antigenic epitope) or that the antibodies may be directed to different MBPs.

In some embodiments the at least two or at least three anti-Bone Morphogenic Protein antibodies are directed against different Bone Morphogenic Proteins.

As indicated above, administration of a specific combination of antibodies, namely antibodies directed against BMP 2, 4, 5 and 7 ameliorated the clinical symptoms of RR-EAE mice. Thus, in some embodiments, the pharmaceutical composition according to the invention comprises anti-Bone Morphogenic Protein antibodies that are selected from the group consisting of anti-BMP-2, anti-BMP-4, anti-BMP-2/4, anti-BMP-5 and anti-BMP-7 antibodies or functional fragments thereof.

For example, the pharmaceutical composition according to the invention may comprise anti-Bone Morphogenic Protein antibodies directed against BMP-2 and BMP-4, BMP-5 and BMP-7, BMP-4 and BMP-5, BMP-7 and BMP-2 to name but few combinations of at least two BMP antibodies.

In some embodiments the pharmaceutical composition according to the invention comprises the anti-human Bone Morphogenic Protein antibodies anti-human BMP-2/4, anti-human BMP-5 and anti-human BMP-7 antibodies or functional fragments thereof.

In some specific embodiments the pharmaceutical composition according to the invention comprises the anti-human Bone Morphogenic Protein antibodies anti-human BMP-2, anti-human BMP-4, anti-human BMP-2/4, anti-human BMP-5 and anti-human BMP-7 antibodies or functional fragments thereof.

As indicated above, the inventors have demonstrated that a monoclonal antibody directed against both BMP-2 and BMP-4 (referred to herein as "anti-BMP-2/4 mAb") was also effective in ameliorating the clinical symptoms of RR-EAE as a single agent. As clear to a person skilled in the art of the invention, the beneficial therapeutic effect demonstrated for the above anti-BMP-2/4 mAb is not limited to the particular antibody disclosed herein per se.

Thus the present invention also provides a pharmaceutical composition comprising the anti-Bone Morphogenic Protein antibodies anti-BMP-2 and anti-BMP-4 or functional fragments thereof.

Still further, in some embodiments the pharmaceutical composition according to the invention comprises a single anti-Bone Morphogenic Proteins antibody selected from the group consisting of anti-BMP-2, anti-BMP-4, anti-BMP-2/4, anti-BMP-5, anti-BMP-7 antibodies and functional fragments thereof.

In yet further embodiments the pharmaceutical composition according to the invention comprises a single anti-Bone Morphogenic Protein antibody that is directed against BMP-2 and BMP-4 (i.e. a single antibody directed to both BMP-2 and BMP-4).

Thus, provided is a pharmaceutical composition for the treatment of a neuroinflammatory disease, a neurodegenerative disease or CNS damage comprising an antibody, or functional fragments thereof, directed against Bone Morphogenic Protein 2/4 (BMP-2/4) and a pharmaceutically acceptable carrier.

In accordance with certain embodiments the antibodies of the invention are directed against a human BMP.

As indicated above, the antibodies according to the invention may be monoclonal antibodies. In further embodiments the pharmaceutical composition according to the invention comprises monoclonal antibodies. The monoclonal antibodies of the invention may be non human, chimeric, humanized, or human antibodies.

The term "chimeric antibody (or antibodies)" as herein defined refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments. A typical therapeutic chimeric antibody is thus a hybrid protein composed of the variable or antigen-binding domain from a mouse antibody and the constant domain from a human antibody, although other mammalian species may be used.

In some embodiments, the antibody according to the invention is non human, e.g. a mouse monoclonal antibody directed to a human antigen (e.g. the monoclonal antibodies described in the Examples below are mouse monoclonal antibodies directed to a human antigen).

The term "humanized antibodies" as herein defined refers to antibodies from non-human species (e.g. mouse) whose protein sequences have been modified to increase their similarity to antibody variants produced naturally in humans.

In some embodiments, the antibodies of the invention may be humanized antibodies. "Humanized" forms of non-human antibodies are antibodies having a framework of human sequences and a minimal sequence that is derived from the epitope binding site of a non-human antibody. Therefore, the humanized antibodies in accordance with the invention are human immunoglobulins (the recipient antibody) in which residues from the hypervariable region are replaced by residues from a hypervariable region of a non-human species (the donor antibody). As non-binding examples, such species may be mouse, rat, rabbit or non-human primate having the desired antibody specificity, affinity, and capability. In some embodiments, additional framework region (FR) residues of the human immunoglobulin are replaced by corresponding non-human residues in order to enhance antibody specificity, affinity and/or stability. In further embodiments, the humanized antibodies of the invention may comprise modifications, for example, residues that are not found in the recipient antibody or in the donor antibody. These modifications are made to further refine antibody performance.

The preparation of humanized antibodies is known in the art. In general, a humanized antibody will comprise at least one, and typically two, variable domains, in which all or substantially all of the hypervariable loops correspond to those of a non-human immunoglobulin and all, or substantially all, of the FRs are those of a human immunoglobulin sequence. The humanized antibody optionally also will comprise at least a portion of an immunoglobulin constant region (Fc), typically that of a human immunoglobulin.

In other embodiments the antibody according to the invention is a human antibody. The term "human antibody (or antibodies)" as herein defined is an antibody which possesses an amino acid sequence which corresponds to that of an antibody produced by a human. Human antibodies can be produced using various techniques known in the art, including phage-display libraries, transgenic mice and in vitro human hybridoma technologies.

As indicated above, blocking agents of BMP signaling are generally known in the art and are used herein in the broadest sense, referring to any molecule which may inhibit BMP signaling. Thus, by way of example, the blocking agent of human BMP signaling according to the invention may be directed against any component involved in BMP signaling (e.g. a BMP receptor) or against any element of the downstream signal transduction cascade associated with human BMPs signaling, thereby indirectly affecting BMP activity.

For example, the human blocking agent of BMP signaling according to the invention may be directed against a BMP receptor e.g. the BMP type I receptors ALK2, ALK3 or ALK6, as in the case of dorsomorphin, which was found to selectively inhibit the BMP type I receptors ALK2, ALK3 and ALK6 and thus to block BMP-mediated SMAD1/5/8 phosphorylation.

Further non limiting examples for a blocking agent of human BMP signaling according to the invention are the protein complex Inhibin, BMP-3 and various small molecules, such as dorsomorphin and derivatives thereof (e.g. LDN-193189) [11 and 12], as well as Noggin, Chordin and Chordin-like molecules, Follistatin and Follistatin-related gene (FLRG), Ventroptin, twisted gastrulation (Tsg), Dan family antagonists (e.g. Dan, Cerberus, Gremlin, Dante, Caronte, Protein related to Dan and Cerberus (PRDC), Sclerostin and sclerostin-like, Coco, Cer1, and Uterine sensitization-associated gene 1 (USAG-1)) and connective tissue growth factor (CTGF)) [13, 14 and 15].

Thus in some embodiments, the blocking agent of human Bone Morphogenic Protein (BMP) signaling according to the invention is selected from the group consisting of dorsomorphin, LDN-193189, a BMP receptor antagonist, the protein complex Inhibin, BMP-3, Noggin, Chordin and Chordin-like molecules, Follistatin and Follistatin-related gene (FLRG), Ventroptin, twisted gastrulation (Tsg), Dan, Cerberus, Gremlin, Dante, caronte, Protein related to Dan and Cerberus (PRDC), Sclerostin and sclerostin-like, Coco, Cer1, Uterine sensitization-associated gene 1 (USAG-1) or connective tissue growth factor (CTGF), or any combination thereof.

As shown by Example 13 below (FIG. 16), EAE-induced mice treated with dorsomorphin, which is a potent inhibitor of BMP signaling, exhibited a very mild form of the disease. As shown below, only after dorsomorphin treatment was ceased the disease became active, i.e. the onset of the first relapse in dorsomorphin treated-mice was delayed. In addition, as demonstrated in FIG. 17, until day 16 post immunization, there were no mice exhibiting the severe forms of the disease (score 2-5) in the dorsomorphin-treated group, as compared to the vehicle-treated group.

Thus, in some embodiments the pharmaceutical composition for the treatment of a neuroinflammatory disease, a neurodegenerative disease of CNS damage in accordance with the invention comprises the blocking agent of human Bone Morphogenic Protein (BMP) signaling dorsomorphin and a pharmaceutically acceptable carrier.

Dorsomorphin, (6-[4-(2-Piperidin-1-yl-ethoxy)phenyl]-3-pyridin-4-yl-pyrazolo[1,5-a]pyrimidine), also known as compound C, as herein defined is a potent inhibitor of AMP-activated protein kinase (AMPK) and bone morphogenic protein (BMP) signaling. It was identified in a screen for compounds that perturb dorsoventral axis formation in zebrafish. Dorsomorphin functions through inhibition of BMP type I receptors ALK2, ALK3 and ALK6 and thus blocks BMP-mediated SMAD1/5/8 phosphorylation.

As demonstrated in the Examples section below, the inventors have shown that obstruction of bone morphogenic protein (BMP) signaling, using BMP blocking agents (or antagonists) results in improving the clinical outcome in animal models, which are well-established models mimicking the disease multiple sclerosis (MS), which is considered as a neuroinflammatory and neurodegenerative disease.

Two experimental autoimmune encephalomyelitis (EAE) mice models were used by the inventors for analyzing the effect of blocking agents of BMP signaling (also referred to herein as "BMP antagonists") on multiple sclerosis. The first model was based on SJL mice and chosen based on its relapsing and remitting (RR) pattern, which resembles the pattern of RR-multiple sclerosis in humans, whereas the second model was based on C57BL/6 mice and represented a progressive form of EAE.

The term "Experimental autoimmune encephalomyelitis" (EAE, or Experimental Allergic Encephalomyelitis) as herein defined generally refers to an animal model of brain inflammation, and is a widely accepted model of MS used in drug discovery. It is an inflammatory demyelinating disease of the central nervous system (CNS), mostly used with rodents and is widely accepted as an animal model of human CNS demyelinating diseases, including, but not limited to, multiple sclerosis (MS) and acute disseminated encephalomyelitis (ADEM).

EAE can be induced in a number of species, including mice, rats, guinea pigs, rabbits and primates. The most commonly used antigens used in rodents are spinal cord homogenate (SCH), purified myelin, myelin protein such as myelin basic protein (MBP), Myelin proteolipid protein (PLP or lipophilin), and Myelin Oligodendrocyte Glycoprotein (MOG), or peptides of these proteins, all resulting in distinct models with different disease characteristics regarding both immunology and pathology.

Depending on the antigen used and the genetic make-up of the animal, rodents can display a monophasic bout of EAE, a relapsing-remitting form, or chronic EAE. The typical susceptible rodent will debut with clinical symptoms around two weeks after immunization and will present symptoms of a relapsing-remitting disease.

As indicated above, modeling of multiple sclerosis may be performed with SJL/J Mice. This EAE model is induced in 8-week old SJL/J female mice by the proteolipid protein (PLP) fragment (along with Pertussis toxin). This model exhibits a relapsing-remitting (RR) disease course, resembling those observed in MS patients.

Modeling of multiple sclerosis may also be performed using C57BL/6 female mice, in which disease is induced with myelin-oligodendrocyte glycoprotein peptide (MOG). This model represents progressive (also referred to as chronic) form of the disease.

As known in the art, model animals are usually scored for disease activity (termed "Disease Activity Index", DAI) using the following scoring index: "0", Normal mouse, no overt signs of disease, "1", Limp tail or hind limb weakness but not both, "2", Limp tail and hind limb weakness, "3", Partial hind limb paralysis, "4" Complete hind limb paralysis, and "5", Death or sacrifice for humane reasons. The above scoring index may thus be used for monitoring the severity of the disease and the onset of relapses in order to determine the therapeutic effect of the BMP antagonist according to the invention.

In some embodiments, the neuroinflammatory or neurodegenerative disease according to the invention is Multiple sclerosis. In further specific embodiments the pharmaceutical composition according to the invention is for the treatment of multiple sclerosis.

The term "Multiple Sclerosis" (MS) as herein defined is a chronic inflammatory neurodegenerative disease of the central nervous system that destroys myelin, oligodendrocytes and axons. MS is the most common neurological disease among young adults, typically appearing between the ages of 20 and 40. Over 400,000 Americans suffer from MS. The symptoms of MS vary, from the appearance of visual disturbance such as visual loss in one eye, double vision to muscle weakness fatigue, pain, numbness, stiffness and unsteadiness, loss of coordination and other symptoms such as tremors, dizziness, slurred speech, trouble swallowing, and emotional disturbances. As the disease progresses patients may lose their ambulation capabilities, may encounter cognitive decline, lose of self managing of everyday activities and may become severely disabled and dependent.

MS symptoms develop because immune system elements attack the brain's cells (neurons) and damage the protective myelin sheath of axons. The areas in which these attacks occur are called lesions that disrupt the transmission of messages through the brain.

Multiple sclerosis is classified into four types, characterized by disease progression: (1) Relapsing-remitting MS (RRMS), which is characterized by relapse (attacks of symptom flare-ups) followed by remission (periods of stabilization and possible recovery; while in some remissions there is full recovery, in other remissions there is partial or no recovery). Symptoms of RRMS may vary from mild to severe, and relapses may last for days or months. More than 80 percent of people who have MS begin with relapsing-remitting cycles; (2) Secondary-progressive MS (SPMS) develops in people who have relapsing-remitting MS. In SPMS, relapses may occur, but there is no remission (stabilization) for a meaningful period of time and the disability progressively worsens; (3) Primary-progressive MS (PPMS), which progresses slowly and steadily from its onset and accounts for less than 20 percent of MS cases. There are no periods of remission, and symptoms generally do not decrease in intensity; and (4) Progressive-relapsing MS (PRMS). In this type of MS, people experience both steadily worsening symptoms and attacks during periods of remission.

Currently, Multiple sclerosis has no cure. Treatment usually focuses on strategies to treat MS attacks, manage symptoms and reduce the progress of the disease. Among the known agents used for the treatment of MS are corticosteroids that are mainly used to reduce the inflammation that spikes during a relapse, beta interferons, which slow the progress of multiple sclerosis, reduce the number of attacks and lessen the severity of attacks, Glatiramer acetate (Copaxone), which reduces the number of MS attacks, Fingolimod (Gilenya), Natalizumab (Tysabri) and other agents known in the art. New emerging therapies that reduce the relapse rate and mildly affect disability progress include dimethyl fumarate (BG-12, tecfidera), teriflunomide (aubagio) and Alemtuzumab (Campath 1-H, Lemtrada).

Diagnosis of multiple sclerosis may be performed by any method known in the art and includes Lumbar puncture (spinal tap) for cerebrospinal fluid tests, including CSF oligoclonal banding, MRI scan of the brain and MRI scan of the spine and nerve function study (evoked potential test).

In some embodiments, the invention provides a pharmaceutical composition for the treatment of Multiple sclerosis comprising at least one antibody, or functional fragments thereof, directed against human Bone Morphogenic Protein (BMP) and a pharmaceutically acceptable carrier.

In further exemplary embodiments the invention provides a pharmaceutical composition for the treatment of Multiple sclerosis comprising at least one of the anti-human Bone Morphogenic Protein antibodies anti-human BMP-2, anti-human BMP-4, anti-human BMP-2/4, anti-human BMP-5 and anti-human BMP-7 antibodies or functional fragments thereof.

In other embodiments, the neurodegenerative disease according to the invention is Huntington's disease. The term "Huntington's disease" (HD) as herein defined refers to a neurodegenerative genetic disorder that affects muscle coordination and leads to cognitive decline and dementia. Huntington's disease is a fatal hereditary disorder, resulting from a mutation in the gene coding for a protein known as "huntingtin". While 30,000 people in the United States currently suffer from the disease, over 150,000 individuals are at risk of developing Huntington's.

No treatments can alter the course of Huntington's disease, and medications can only lessen some symptoms of movement disorders and psychiatric disorders associated with the disease. Known medications for the treatment of Huntington's disease include Tetrabenazine (Xenazine), haloperidol (Haldol) and clozapine (Clozaril), all of which have many side effects.

In some embodiments, the invention provides a pharmaceutical composition for the treatment of Huntington's disease comprising at least one antibody, or functional fragments thereof, directed against human Bone Morphogenic Protein (BMP) and a pharmaceutically acceptable carrier.

In further specific embodiments the neurodegenerative disease according to the invention is Alzheimer's disease. The term "Alzheimer's disease" (AD) as herein defined is an irreversible, progressive brain disease that slowly destroys memory and thinking skills, and eventually even the ability to carry out the simplest tasks. Alzheimer's disease (also known as Alzheimer disease) is the most common form of dementia, which is a serious loss of global cognitive ability in a previously unimpaired person, beyond what might be expected from normal ageing. Most often, AD is diagnosed in people over 65 years of age. As the disease advances, symptoms include confusion, irritability, aggression, trouble with language, and long-term memory loss.

Two types of drugs are currently used to treat cognitive symptoms associated with Alzheimer's disease: Cholinesterase inhibitors (e.g. donepezil (Aricept), galantamine (Razadyne) and rivastigmine (Exelon)), which suffer from side effects including diarrhea, nausea and sleep disturbances and Memantine (Namenda).

In some embodiments, the invention provides a pharmaceutical composition for the treatment of Alzheimer's disease comprising at least one antibody, or functional fragments thereof, directed against human Bone Morphogenic Protein (BMP) and a pharmaceutically acceptable carrier.

In still further specific embodiments the neurodegenerative disease according to the invention is Parkinson's disease. The term "Parkinson's disease" as herein defined refers to a progressive disorder of the nervous system that affects movement. It develops gradually, sometimes starting with a barely noticeable tremor in just one hand.

But while tremor may be the most well-known sign of Parkinson's disease, the disorder also commonly causes stiffness or slowing of movement. Over 1 million Americans suffer from Parkinson's disease (PD). More than 60,000 patients are newly diagnosed each year. Although PD typically strikes individuals at about 60 years of age, in some cases PD begins earlier in life.

Parkinson's disease cannot be cured, but medications aid in controlling its symptoms. Known medications for the treatment of Parkinson's disease include, but are not limited to Carbidopa-levodopa (Parcopa), Dopamine agonists (e.g. pramipexole (Mirapex) and ropinirole (Requip)), where known side effects of dopamine agonists and carbidopa-levodopa include hallucinations, swelling, sleepiness or compulsive behaviors. Other agents for the treatment of Parkinson's disease include monoamine oxidase B (MAO B) inhibitors (e.g. selegiline (Eldepryl, Zelapar) and rasagiline (Azilect)), Catechol O-methyltransferase (COMT) inhibitors (e.g. Entacapone (Comtan)), Anticholinergics (e.g. benztropine (Cogentin) and trihexyphenidyl), Amantadine and other agents known in the art.

In some embodiments, the invention provides a pharmaceutical composition for the treatment of Parkinson's disease comprising at least one antibody, or functional fragments thereof, directed against human Bone Morphogenic Protein (BMP) and a pharmaceutically acceptable carrier.

In some embodiments the neurodegenerative disease according to the invention is Amyotrophic Lateral Sclerosis (ALS, also known as Lou Gehrig's disease). ALS is a progressive, fatal disorder, usually appearing between the ages of 40 and 70, and affects more men than women. About 30,000 Americans currently suffer from ALS. Initial signs of ALS include twitching, cramping, weakness in the legs and arms, and difficulty speaking, chewing, or swallowing. As symptoms spread throughout the body, weight loss, fatigue, exaggerated reflexes, and decreased coordination become common. Ultimately, patients cannot walk, stand, eat, or breathe without assistance.

There is no cure for ALS and there is currently only one approved medicine (Riluzole) to treat the disease. While Riluzole may slow the disease for a few months, it has no lasting effect.

In some embodiments, the invention provides a pharmaceutical composition for the treatment of ALS comprising at least one antibody, or functional fragments thereof, directed against human Bone Morphogenic Protein (BMP) and a pharmaceutically acceptable carrier.

In other specific embodiments the neuroinflammatory disease according to the invention is neurosarcoidosis. Sarcoidosis is a disorder that affects many parts of the body, mostly the lungs. In a small number of patients, the disease involves some part of the nervous system and the disease is then called neurosarcoidosis. Therefore, the term "neurosarcoidosis" relates to a complication of sarcoidosis in which inflammation occurs in the brain, spinal cord, and other areas of the nervous system.

Neurosarcoidosis may affect any part of the nervous system. Sudden, facial weakness (facial palsy) is the most common neurological symptom and involves the facial muscles nerves. Any nerve in the skull can be affected, including those in the eye and those that control taste, smell, or hearing. The condition can also affect the parts of the brain involved in regulating many body functions such as temperature, sleep, and stress responses. Muscle weakness or sensory losses can occur with peripheral nerve involvement. Other areas of the brain, including the pituitary gland at the base of the brain, or the spinal cord may also be involved.

In some embodiments, the invention provides a pharmaceutical composition for the treatment of neurosarcoidosis comprising at least one antibody, or functional fragments thereof, directed against human Bone Morphogenic Protein (BMP) and a pharmaceutically acceptable carrier.

As indicated above, the present invention is also directed to pharmaceutical compositions and to a method of treatment of nervous system damage, in particular CNS damage. In the context of the present invention, the term Central nervous system (CNS) damage relates to conditions in the CNS which are associated with neuronal cell or tissue injury resulting from stroke, trauma to cerebral or spinal cord tissue, or lesions in neuronal tissue, for example CNS trauma, Anoxic brain damage and CNS vasculitis.

In still further embodiments the Central nervous system (CNS) damage according to the invention is a result of stroke or the neuronal cell or tissue injury arising thereafter. A "stroke" (also known as cerebrovascular accident, CVA), as herein defined is the rapid loss of brain function due to disturbance in the blood supply to the brain. This can be due to ischemia (lack of blood flow caused by blockage) or a hemorrhage (bleeding). As a result, the affected area of the brain cannot function, which might result in an inability to move one or more limbs on one side of the body, inability to understand or formulate speech, among other symptoms. A stroke is a medical emergency and can cause permanent neurological damage and death. An ischemic stroke is occasionally treated by thrombolysis and some hemorrhagic strokes may benefit from neurosurgery. Treatment to recover any lost function is termed stroke rehabilitation.

In some embodiments, the invention provides a pharmaceutical composition for the treatment of stroke comprising at least one antibody, or functional fragments thereof, directed against human Bone Morphogenic Protein (BMP) and a pharmaceutically acceptable carrier.

The Central nervous system (CNS) damage according to the invention may also be a result of trauma to cerebral or spinal cord tissue or of lesions in neuronal tissue, as indicated above, for example, CNS trauma, Anoxic brain damage and CNS vasculitis.

The term "CNS trauma" or injury to the central nervous system (CNS) includes injuries inflicted to the brain and spinal cord and are major health problems. More than 2 million people in the U.S. suffer traumatic brain injuries annually, well over 500,000 people per year suffer from stroke, and at least 10,000 people per year suffer spinal cord injuries. Most people suffering from CNS injuries must endure irreversible disabilities as a result of these insults.

The term "Anoxic brain damage" as herein defined occurs when the brain receives inadequate oxygen for several minutes or longer. Brain cells begin to die after approximately four minutes without oxygen. Anoxic brain damage may occur for example, when oxygenated blood cannot reach the brain (for example, when a clot prevents blood flow to the brain), when blood that reaches the brain does not carry enough oxygen (for example, when lung disease prevents oxygen from crossing from the lungs into the blood for transport), or in people exposed to poisons or other toxins that keep oxygen in the blood from being used by the cells in the brain (for example, carbon monoxide, which binds the oxygen carrying molecules in the blood and prevents transport of oxygen).

The term "CNS vasculitis" (CNSV) as herein defined refers to a rare disease which is characterized by an inflammation of the Central Nervous System, affecting the blood vessels in the brain and or spinal cord. Diagnosing CNSV is a clinical challenge because it is a syndrome, not a specific disease; and can be easily misdiagnosed as Lupus and/or Multiple Sclerosis, or any number of other diseases. Vasculitis can be classified as Primary when there is no other disease or condition present that may cause blood vessels to be damaged. Secondary vasculitis of the central nervous system is more common and can be one part of a variety of systemic illnesses such as Lupus. Secondary CNSV can also be caused by a reaction to drugs such as amphetamines or cocaine and even some over-the-counter cold remedies. Vasculitis can also occur in association with systemic connective tissue diseases, infection, malignancy and organ transplants.

In some embodiments, the invention provides a pharmaceutical composition for the treatment of CNS trauma, Anoxic brain damage or CNS vasculitis comprising at least one antibody, or functional fragments thereof, directed against human Bone Morphogenic Protein (BMP) and a pharmaceutically acceptable carrier.

In some embodiments the pharmaceutical composition according to the invention is for the treatment of glioma. The term "Glioma" as herein defined refers to a type of tumor that originates in the brain or spine, arising from glial cells. The main types of gliomas are Ependymomas, Astrocytomas, Oligodendrogliomas, Mixed gliomas, such as oligoastrocytomas, contain cells from different types of glia. In one embodiment, the term glioma encompasses tumors whose development is blocked by antagonists of BMP (e.g. by anti BMP antibodies), for example an astrocytoma.

In some specific embodiments the pharmaceutical composition according the invention is for the treatment of a "demyelinating disease". The term "demyelinating disease" as herein defined is any disease of the nervous system in which the myelin sheath of neurons is damaged or removed resulting in abrogated function of the neuronal cells.

In some embodiments the pharmaceutical composition according to the invention further comprises at least one additional therapeutic agent.

In further embodiments the pharmaceutical composition according to the invention is for use in combination with at least one additional therapeutic agent.

A person skilled in the art in the field of the invention (e.g. a physician) will know how to identify an "additional therapeutic agent" that will be suitable for the treatment of any of the neuroinflammatory disease, a neurodegenerative disease or CNS damage encompassed by the present disclosure, as the case may be.

For example, the additional therapeutic agent according to the invention may be, but is not limited to nerve growth factor (NGF), an apoptosis inhibitor, an EGFR inhibitor, a β-secretase inhibitor, a γ-secretase inhibitor, a cholinesterase inhibitor, and a NMDA receptor antagonist.

Further specific examples include but are not limited to corticosteroids, beta interferons, Glatiramer acetate (Copaxone), Fingolimod (Gilenya) and Natalizumab (Tysabri) for the treatment of Multiple sclerosis, Tetrabenazine (Xenazine), haloperidol (Haldol) and clozapine (Clozaril), for the treatment of Huntington's disease, Cholinesterase inhibitors (e.g. donepezil (Aricept), galantamine (Razadyne) and rivastigmine (Exelon)), and Memantine (Namenda) for the treatment of Alzheimer's disease, Carbidopa-levodopa (Parcopa), Dopamine agonists (e.g. pramipexole (Mirapex) and ropinirole (Requip)), monoamine oxidase B (MAO B) inhibitors (e.g. selegiline (Eldepryl, Zelapar) and rasagiline (Azilect)), Catechol O-methyltransferase (COMT) inhibitors (e.g. Entacapone (Comtan)), Anticholinergics (e.g. benztropine (Cogentin) and trihexyphenidyl) and Amantadine for the treatment of Parkinson's disease.

In some embodiments the additional therapeutic agent is an anti-inflammatory agent.

The invention encompasses the use of any anti inflammatory agent known in the art suitable for the treatment of neuroinflammatory or neurodegenerative diseases. Non-limiting examples of "anti-inflammatory agents" according to the invention include glatiramer acetate (Copaxone), interferon-beta, natalizumab, fingolimod, mitoxantrone, non-steroidal anti-inflammatory drugs (NSAIDs) and Cannabinoids (e.g. THC), Steroids, dimethyl fumarate (BG-12, tecfidera), teriflunomide (aubagio), Alemtuzumab (Campath 1-H, Lemtrada), Ocrelizumab, Rituximab, Ofatumumab, Liquinimod, Daclizumab, Azathioprine, Mycophenolate mofetil, Cyclophosphamide, Methotrexate, Intravenous immunoglobulins (IVIG), Plasma exchange and others.

As used herein, the term "pharmaceutical composition" refers to a preparation of at least one human Bone Morphogenic Protein (BMP) antagonist (or an agent capable of blocking BMP signaling) described herein (e.g. the anti-human Bone Morphogenic Protein (BMP) antibodies or the antagonist dorsomorphin) with other chemical components such as pharmaceutically acceptable carrier and excipients. The purpose of a pharmaceutical composition is to facilitate administration of a compound to a subject.

The term "pharmaceutically acceptable carrier" includes any and all solvents, dispersion media, coatings, antibacterial and antifungal agents and the like and refers to a carrier or a diluent that does not cause significant irritation to an organism and does not abrogate the biological activity and properties of the administered antagonist. An adjuvant is included under this term. Herein, the term "excipient" refers to an inert substance added to a pharmaceutical composition to further facilitate administration of an active ingredient.

Examples, without limitation, of excipients include calcium carbonate, calcium phosphate, various sugars and types of starch, cellulose derivatives, gelatin, vegetable oils, and polyethylene glycols.

Pharmaceutical compositions according to the invention may be manufactured by processes well known in the art, using one or more pharmaceutically acceptable carriers, e.g., by means of conventional mixing, dissolving, granulating, emulsifying, encapsulating, entrapping, or lyophilizing processes. Proper formulation is dependent upon the route of administration chosen.

For example, techniques for formulation and administration of active agents (e.g. the anti-human Bone Morphogenic Protein (BMP) antibodies and dorsomorphin) may be found in the latest edition of "Remington's Pharmaceutical Sciences," Mack Publishing Co., Easton, Pa., which is herein fully incorporated by reference.

Further provided is a method of treatment of a subject suffering from a neuroinflammatory disease, a neurodegenerative disease or CNS damage comprising administering to said subject a therapeutically effective amount of at least one blocking agent of Bone Morphogenic Protein (BMP) signaling and a pharmaceutically acceptable carrier.

As shown in the Examples below, treatment of mice induced with Experimental autoimmune encephalomyelitis (EAE), with anti-BMP-2/4, 5 and 7 antibodies or with dorsomorphin resulted in a significant alleviation of EAE symptoms. Similar effects were observed in two types of EAE mice, namely both in mice induced with the Relapsing and remitting form of the disease (RR-EAE) and in mice induced with the progressive (chronic) form thereof.

Remarkably, treatment with anti-BMP-2/4 antibodies as a single therapy was also effective in ameliorating the symptoms of RR-EAE. As shown in the Examples below, treatment according to the invention reduced the severity of symptoms in EAE mice and delayed the onset of relapses.

Interestingly, in addition to the observed clinical manifestations of the therapeutic effect of the agent capable of blocking Bone Morphogenic Protein (BMP) signaling according to the invention, the inventors have also shown that various brain sections of EAE mice treated with antibodies directed against BMPs 2, 4, 5 and 7 showed an increase in several markers that are indicative of neural differentiation (e.g. Example 5-7).

Thus the term "treatment" as herein defined refers to clinical intervention in an attempt to alter the natural course of disease in the subject being treated and can be performed either by prophylaxis or during the course of clinical pathology. Desirable effects of treatment include preventing occurrence or recurrence of disease, reduction, alleviation or elimination of symptoms, decreasing the rate of disease progression, amelioration or reduction of the disease severity or state, improved prognosis, delaying the onset of the symptoms of a disease, delaying relapses as well as inducing neurogenesis and myelination.

The therapeutic effect of a blocking agent of human Bone Morphogenic Protein (BMP) signaling according to the invention on a neuroinflammatory or a neurodegenerative disease may be analyzed by any method known to a skilled person in the art.

In specific embodiments the neuroinflammatory or neurodegenerative disease according to the invention is multiple sclerosis. Treatment of subjects suffering from multiple sclerosis may be monitored by any method known in the art e.g. the therapeutic effect of treatment according to the invention may be assessed by clinical rating scales that have been developed for multiple sclerosis patients. The most commonly used scales in MS are the "Disability Status Scale" (DSS), the "Expanded Disability Status Scale" (EDSS), the Scripps Neurological Rating Scale (SNRS), the Functional Independence Measure (FIM), the Ambulation Index (AI), the Cambridge Multiple Sclerosis Basic Score (CAMBS) [16] as well as the Paced Auditory Serial Addition Test (PASAT) and the Nine-Hole Peg Test.

In some embodiments the effect of the treatment according to the invention on subjects suffering from MS may be monitored by the "Disability Status Scale" (DSS), which is a combination of grades (0=normal to 5 or 6=maximal impairment) within 8 Functional Systems (FS). The DSS has steps from 0 (normal) to 10 (death due to MS). In other embodiments the effect of the treatment according to the invention on subjects suffering from MS may be monitored by the "Expanded Disability Status Scale" (EDSS, also termed the "Kurtzke scale") in which each of the former steps (1, 2, 3 . . . 9) is now divided into two (1.0, 1.5, 2.0 . . . 9.5). The lower portion is obligatorily defined by Functional System grades. The Functional Systems are Pyramidal, Cerebellar, Brain Stem, Sensory, Bowel & Bladder, Visual, Cerebral, and Other; the Sensory and Bowel & Bladder Systems have been revised [17].

In some embodiments the method of treatment according to the invention comprises administering a blocking agent of human Bone Morphogenic Protein (BMP) signaling that is an anti BMP antibody or functional fragments thereof.

It is noted that the blocking agent of human Bone Morphogenic Protein (BMP) signaling (e.g. an anti-BMP antibody, dorsomorphin and others), the neuroinflammatory disease, the neurodegenerative disease (e.g. multiple sclerosis) or the CNS damage encompassed in the method of treatment according to the invention are as defined above, including specific examples and embodiments thereof.

In addition, the method of treatment according to the invention comprises administering to a subject a therapeutically effective amount of at least one blocking agent of human Bone Morphogenic Protein (BMP) signaling per se or any pharmaceutical composition comprising said at least one blocking agent of human Bone Morphogenic Protein (BMP) signaling in accordance with the invention.

Administration to a subject suffering from a neuroinflammatory disease, a neurodegenerative disease or a CNS damage of a therapeutically effective amount of at least one blocking agent of Bone Morphogenic Protein (BMP) signaling may be performed by any route known in the art.

By way of example, routes of administration include, but are not limited to, oral, rectal, transmucosal, transnasal, intestinal, or parenteral delivery, including intramuscular, subcutaneous, and intramedullary injections, as well as intrathecal, direct intraventricular, intravenous, inrtaperitoneal, intranasal, or intraocular injections. Alternately, one may administer the pharmaceutical composition according to the invention in a local rather than systemic manner, for example, via injection of the pharmaceutical composition directly into a tissue region of a subject.

As known in the art, in MS as in the case of other diseases (e.g. neuroimmune diseases and cerebrovascular diseases), blood brain barrier (BBB) breach is associated with the CNS insult, therefore without wishing to be bound by theory, the administrated agent is introduced preferentially into the affected CNS areas. Thus, in some embodiments the route of administration is intravenous (i.v.).

In other embodiments, the BMP signaling blocking agent of the invention is administered in combination with an additional therapeutic agent, which mediates opening of the BBB, for example Manitol, which is intravenously injected. Use of such an additional agent may be required in neurodegenerative diseases such as Alzheimer, Parkinson's disease, ALS, and Huntington where there is no BBB breach.

As known in the art, the term the "blood-brain barrier (BBB)" relates to the structural separation of the central nervous system from circulating blood.

The term "therapeutically effective amount" (or amounts) of the at least one blocking agent of human Bone Morphogenic Protein (BMP) signaling according to the invention for purposes herein defined is determined by such considerations as are known in the art in order to cure, arrest or at least alleviate the medical condition. For any preparation used in the methods of the invention, the dosage or the therapeutically effective amount can be estimated initially from in vitro and cell culture assays.

For example, the dosage below was estimated based on a mouse model of multiple sclerosis. As shown in Example 2 below, treatment with 30 μg/mouse of each of the antibodies anti-BMP-2/4, 5 and 7 mAbs led to an improvement of 58.3% (relative to vehicle treatment) and of 56.08% (relative to IC treatment) on day 12 post EAE induction, an effect that was maintained throughout the first relapse. Remarkably, the symptoms in EAE mice treated as above were less severe than those in the controls, at each phase of the study. This effect was also manifested by the fact that in the anti-BMPs treated EAE mice group there were less mice exhibiting a severe form of the disease (i.e. mice exhibiting moderate and severe forms of the disease, with a clinical score of 2-5).

In addition, in EAE mice, which have been treated with anti-BMPs mAbs (at 30 μg/mouse), the second relapse was delayed. Therefore, it can be concluded that treatment using antibodies directed to BMPs according to the invention affect both the severity and the onset of the relapses of the disease in RR-EAE model. A similar ameliorating effect of treatment with the antibodies according to the invention (each at 15 µg/mouse) was demonstrated in mice exhibiting the progressive (chronic) form of EAE, as shown in Example 3 below.

Thus, in some embodiments the blocking agent of Bone Morphogenic Protein (BMP) signaling is an antibody and the therapeutically effective amount thereof ranges from 15 to 30 µg per mouse (see FIG. 3). This therapeutically effective amount in a mouse weighing 25 gr corresponds to about 0.6 to 1.2 mg/kg, the human equivalent dose (HED) of which being about 0.05 to 0.1 mg/kg. In some embodiments the antibody is provided at a range of 0.1 to 50 mg/kg. In yet other embodiments the therapeutically effective amount of the antibody is 100 mg/dose, 200 mg/dose, 300 mg/dose, 500 mg/dose, 1000 mg/dose or more.

In addition, as shown by Example 16 below, EAE-induced mice treated with dorsomorphin (at 10 mg/kg) exhibited a very mild form of the disease throughout the dorsomorphin treatment and the onset of the first relapse in dorsomorphin treated-mice was delayed.

Therefore in other embodiments the blocking agent of human Bone Morphogenic Protein (BMP) signaling is dorsomorphin and the therapeutically effective amount thereof is in the range of about 10 to 20 mg/kg in mouse, the human equivalent dose (HED) of which being about 0.8 to 16 mg/kg. In some embodiment the therapeutically effective dose is between about 16 mg/kg to 50 mg/kg or more.

It is to be noted that the amount of the BMP signaling blocking agent to be administered may vary by about 5-25%, in consideration of the molecular weight and other features of a specific agent. Thus the term "about" as herein defined refers to a fluctuation of 5-25% of the amount as herein defined.

The blocking agent of human Bone Morphogenic Protein (BMP) signaling according to the invention or any pharmaceutical composition comprising same may be administered to a subject according to the invention at a single or at multiple administrations. The blocking agent of human BMP signaling or the pharmaceutical composition comprising same may be administered to the subject continuously or for discrete periods of time, as determined by such considerations as known to a person skilled in the art in order to cure, arrest or at least alleviate the medical condition.

Toxicity and therapeutic efficacy of the antagonist described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of which follows.

The term "subject" as used herein means warm-blooded animals, such as for example rats, mice, dogs, cats, guinea pigs, primates and humans. Although the methods of the invention are particularly intended for the treatment of human subject suffering from a neuroinflammatory or a neurodegenerative disease, other mammalian subjects are included.

The present invention also discloses at least one blocking agent of Bone Morphogenic Protein (BMP) signaling and a pharmaceutically acceptable carrier for use in a method of treatment of a subject suffering from a neuroinflammatory disease, a neurodegenerative disease or nervous system, in particular CNS damage comprising administering said at least one blocking agent of Bone Morphogenic Protein (BMP) signaling and a pharmaceutically acceptable carrier to said subject.

Further disclosed is use of at least one blocking agent of Bone Morphogenic Protein (BMP) signaling and a pharmaceutically acceptable carrier in the preparation of a pharmaceutical composition for the treatment of a subject suffering from a neuroinflammatory disease, a neurodegenerative disease or nervous system, in particular CNS damage.

It is noted that the blocking agent of Bone Morphogenic Protein (BMP) signaling (e.g. an anti-BMP antibody, dorsomorphin and others), the neuroinflammatory disease, the neurodegenerative disease (e.g. multiple sclerosis) or the nervous system, in particular CNS damage encompassed in the use according to the invention are as defined above, including specific examples and embodiments thereof.

As indicated above, in addition to the observed clinical manifestations of the beneficial therapeutic effect of the blocking agent of Bone Morphogenic Protein (BMP) signaling according to the invention, the inventors have also shown that various brain sections of EAE mice treated with, for example, antibodies directed against BMPs 2, 4, 5 and 7 showed an increase in several markers that are indicative of neural differentiation (e.g. Example 5 and 6).

Namely, the anti BMP antibodies showed a remarkable effect on brain neurogenesis implying their use in promoting neurogenesis, nerve regeneration, remyelination and the like.

Thus the present invention also provides a method of inducing neurogenesis and/or myelination comprising administering to a subject in need thereof at least one blocking agent of Bone Morphogenic Protein (BMP) signaling and a pharmaceutically acceptable carrier.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Unless defined otherwise, all technical and scientific terms used herein have the same meaning as commonly understood by one of ordinary skill in the art to which this invention is related. The following terms are defined for purposes of the invention as described herein.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Abbreviations
Experimental autoimmune encephalomyelitis—EAE;
Relapsing and remitting—RR;
Multiple sclerosis—MS;

Relapsing and remitting experimental autoimmune encephalomyelitis—RR-EAE;
Proteolipid protein peptide—PLP;
Myelin-oligodendrocyte glycoprotein peptide—MOG;
Phosphate buffered saline—PBS;
Complete Freund's Adjuvant—CFA;
Pertussis toxin—PTX;
Bone Morphogenic Protein—BMP;
Blood brain barrier—BBB;
Central nervous system—CNS;
subgranular zone—SGZ;
subventricular zone—SVZ;
dentate gyrus—DG;
ventricular zone—VZ;
lateral ventricles—LV;
isotype controls—IC;
corpus collasum—cc;
Striatum—st;
Monoclonal antibody—mAbs;
CA3—cornu ammonis region 3;
Hour—hr, h;
Minute—min.
Experimental Procedures
Experimental Autoimmune Encephalomyelitis (EAE) Induction in Mice Two EAE mice models were used, as detailed herein below.

The SJL/EAE mice model was chosen based on its relapsing and remitting (RR) pattern, which resembles the pattern of RR-multiple sclerosis in humans. RR-EAE was induced in SJL female mice (8 weeks old, Harlan Laboratories, Ltd. Israel) by subcutaneous immunization (designated day 0) with proteolipid protein peptide (PLP$_{139-151}$, BioSight Ltd.) at a concentration of 100 μg/mouse.

A chronic (or progressive) form of EAE was induced in C57BL/6 female mice (6-8 weeks old, Harlan Laboratories, Ltd. Israel) by subcutaneous immunization (day 0) using myelin-oligodendrocyte glycoprotein peptide (MOG$_{35-55}$, Sigma-Aldrich), at a concentration of 300 μg/mouse in 0.1 ml PBS.

In both models the peptides used for EAE induction were emulsified in an equal volume of Complete Freund's Adjuvant (CFA, DIFCO), containing 500 μg *Mycobacterium tuberculosis* H37RA (MT, DIFCO). In addition, the mice received two consecutive intraperitoneal injections of 300 ng Pertussis toxin (PTX, Sigma-Aldrich) in 0.2 ml PBS. The first injection was given at day 0 and a second injection was given 48 h afterwards.

Antibody Administration to EAE Mice

Day 9 post induction of EAE was chosen for administration of anti-BMP neutralizing antibodies, in order to affect both the onset and the severity of EAE. Mice were intravenously injected with a single injection including 15 or 30 μg/mouse of the following antibodies, emulsified in 200 μl PBS: anti-human BMP-2/4 (an antibody which recognizes both BMP-2 and BMP-4), anti-human BMP-5, and anti-human BMP-7 mAbs (all anti-BMP neutralizing monoclonal antibodies were obtained from R&D systems). Commercial anti-human BMPs were used based on the high homology (>95%) between human and mouse BMPs. Anti-BMPs mAbs were injected intravenously. Since the blood brain barrier (BBB) is disrupted in the EAE mice by the presence of pertussis toxin, the injected antibodies are present systemically in the blood stream but are also transmitted to the CNS through the disrupted BBB.

Mice treated with corresponding isotype controls (IgG1 and IgG2β, termed herein "IC") (R&D systems) as well as mice treated with the vehicle PBS alone (termed herein "vehicle") were used as negative controls (n=12 in each group).

Mice were monitored for symptoms of RR-EAE and were scored as follows: "0" for no disease; "1", tail paralysis; "2", hind limb weakness; "3", hind limb paralysis; "4", hind limb and forelimb paralysis; "5", moribund.

All procedures involving mice were performed according to the guidelines of the Animal Ethical Committee of the Sourasky Medical Center.

Administration of BrdU 3 mice of each group were also daily intraperitoneal injected with 1 mg/mouse 5-Bromo-2'-deoxyuridine (BrdU, Sigma-Aldrich), a thymidine analog incorporating into the DNA of dividing cells, starting from treatment day (day 9), for the following 8 days, and were sacrificed on day 18 post immunization for immunohistochemistry analysis of brain sections.

Immunohistochemical Analysis for Detecting BMP-2, 4, 5 and 7, as Well as of the neural Markers, DCX, NeuN, O4 and GFAP Mice were sacrificed (transcardially punctured, and saline-perfused) and their brains were rapidly excised and frozen at −80° C. Coronal serial sections of 10 μm were collected in −20° C. and were kept frozen (−80° C.) until histological examination. Sections were fixed in 4% paraformaldehyde (PFA, Bar-Naor Ltd) for 15 min at room temperature (RT), preincubated in blocking solution which contained 0.2% Triton X-100 (Sigma-Aldrich), 1% bovine serum albumin (BSA, Sigma-Aldrich) and 3% horse serum (Gibco USA) for 1 h, and then incubated overnight at −4° C. with primary antibodies. To detect specific cell types, the following primary antibodies were used: rabbit anti-doublecortin (DCX, 4606, 1:400, cell signaling technology), mouse anti-neuronal-specific nuclear protein (NeuN, MAB377, 1:100, Millipore USA), mouse anti-oligodendrocyte marker O4 (MAB345, 1:100, Millipore) and rabbit anti-glial fibrillary acidic protein (GFAP, G9269-80, 1:100, Sigma-Aldrich). Detection of bone morphogenic proteins (BMPs) was performed by using rabbit anti-BMP-2 and rabbit anti-BMP-5 (1:200, Acris Antibodies USA), as well as mouse anti-BMP-4 and mouse anti-BMP-7 (1:200, Millipore). The second antibody step was performed by labeling with Alexa Fluor 488-conjugated IgG antibodies to mouse or rabbit for 1 h (1:200; Molecular Probes USA). Control slides were incubated with secondary antibody alone. In order to detect BrdU incorporated cells, after fixation step and prior to blocking step, sections were denatured in 2 N HCl in distilled water at 37° C. for 30 min. The primary antibody rat anti-BrdU (1:200, AbD Serotec USA) and the secondary antibody Alexa Fluor® 594 donkey anti-rat IgG (1:200, Molecular Probes) were used to detect BrdU$^+$ cells. Stained sections were examined and photographed by a fluorescence microscope. Digital images were collected and the percentage of positive cells were quantified using Image J software on 3 sections from each mouse (3 mice from each group, total N=9). Inflammatory infiltrates were detected by hematoxylin and eosin staining and were photographed by a light microscope.

The Tetrazolium Salt XTT Proliferation Assay

The test procedure includes cultivation of cells in a 96-well plate, adding the XTT reagent and incubating for 2-24 hours. During the incubation time (usually within 2-5 hours) an orange color is formed, the intensity of which can be measured with a spectrophotometer, in this instance, an ELISA reader. The intensity of the dye is proportional to the number of metabolically active cells, i.e. the greater the number of metabolically active cells in the well, the greater the activity of mitochondrial enzymes, and the higher the concentration of the dye formed.

Tetrazolium salt of XTT (2,3-Bis-(2-methoxy-4-nitro-5-sulfophenyl]-2H-tetrazolium-5-carboxyanilide salt) is cleaved to formazan by the succinate dehydrogenase system of the mitochondrial respiratory chain. Only living cells, possessing an intact mitochondrial membrane and also an intact cell membrane, do have active dehydrogenase.

Example 1

Levels of BMPs 2, 4, 5 and 7 in Neuroproliferative Areas

RR-EAE was induced in SJL female mice as described above. FIG. 1 demonstrates the variation in the average score of RR-EAE symptoms in mice, post RR-EAE induction. On day 18 post induction, the brains of 3 mice were removed and the levels of the bone morphogenic proteins (BMPs) 2, 4, 5 and 7 in the neuroproliferative areas, the subgranular zone (SGZ, in the hippocampus) and the subventricular zone (SVZ, in the lateral ventricle), were examined by immunofluorescent staining of the brain sections with the relevant anti BMP antibodies.

Figure 2H:
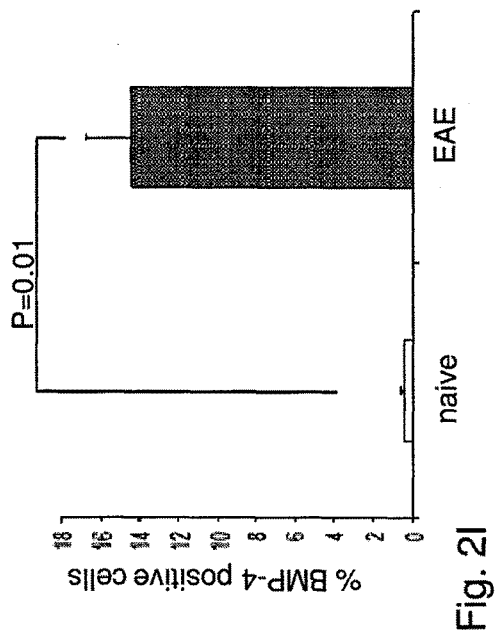
FIG. 2: Graphical representations of induction of BMP-2, 4, 5 and 7 in neuroproliferative areas of RR-EAE mice. Fluorescent micrographs of sections of hippocampus and lateral ventricle areas (respectively) of naïve mice stained with anti BMP-2 antibodies (FIG. 2A and FIG. 2D), anti BMP-4 antibodies (FIG. 2G and FIG. 2J), anti BMP-5 antibodies (FIG. 2M and FIG. 2P) and anti BMP-7 antibodies (FIG. 2S and FIG. 2V). Fluorescent micrographs of sections of hippocampus and lateral ventricle areas (respectively) of RR-EAE mice, obtained on day 18 post immunization, stained with anti BMP-2 antibodies (FIG. 2B and FIG. 2E), anti BMP-4 antibodies (FIG. 2H and FIG. 2K), anti BMP-5 antibodies (FIG. 2N and FIG. 2Q) and anti BMP-7 antibodies (FIG. 2T and FIG. 2W). Scale bar is 500 µm.
FIGS. 2C, 2F, 2I, 2L, 2O, 2R, 2U and 2X show quantification of the percentage of BMPs positive cells, performed on three sections obtained from three mice from each group, using ImageJ software. Abbreviations: CA1, cornu ammonis region 1; CA3, cornu ammonis region 3; VZ, ventricular zone; DG, dentate gyrus; SGZ, subgranular zone; LV, lateral ventricles; SVZ, subventricular zone; st, striatum; fi, fimbria.
Figure 2G:
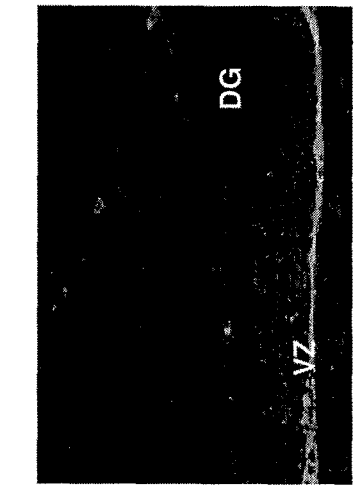
Figure 2J:
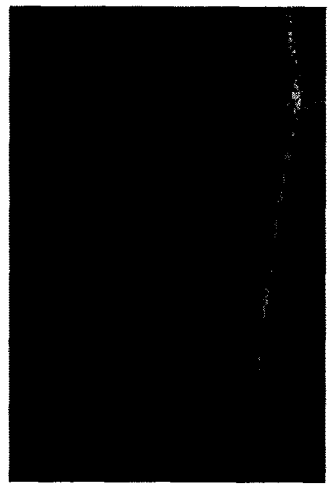
Figure 2I:
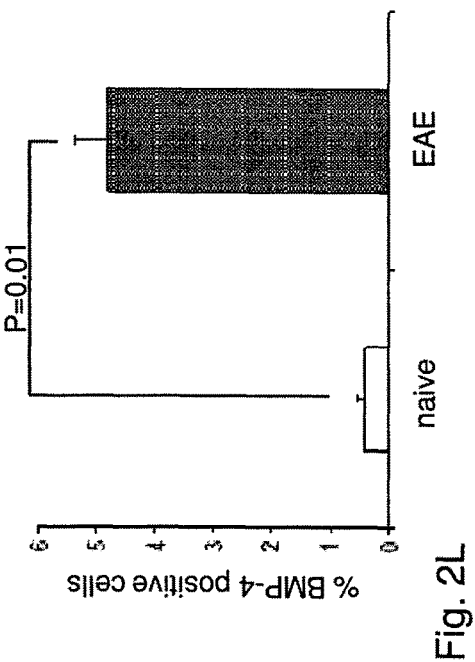

As demonstrated in FIG. 2C and FIG. 2F, in naïve mice, of all the BMPs examined, BMP-2 was found to be the most abundant in both SGZ of the dentate gyrus (DG) and the ventricular zone (VZ), adjacent to the DG, as well as in the SVZ of the lateral ventricles (LV). In contrast, the levels of BMP-4, 5 and 7 in both neuroproliferative zones of naïve mice were insignificant (FIG. 2).

In contrast, in the brains of RR-EAE-induced mice, a significant increase in the levels of all the BMPs tested was observed. Specifically, BMP-2 was up-regulated in both SGZ of the DG and in the VZ adjacent to the DG (FIG. 2B and FIG. 2C, 21.2±1.2% in EAE mice vs. 7.3±0.4% in naïve mice, p=0.009), as well as in the SVZ of the LV (FIG. 2E and FIG. 2F, 17.4±2.1% in EAE mice vs. 9.4±0.6% in naïve mice, p=0.03).

Figure 2K:
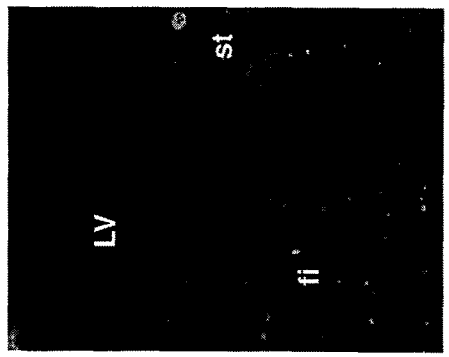
Figure 2L:
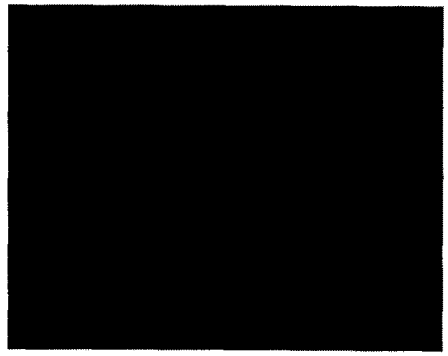
Figure 2M:
Figure 2N:
Figure 2O:
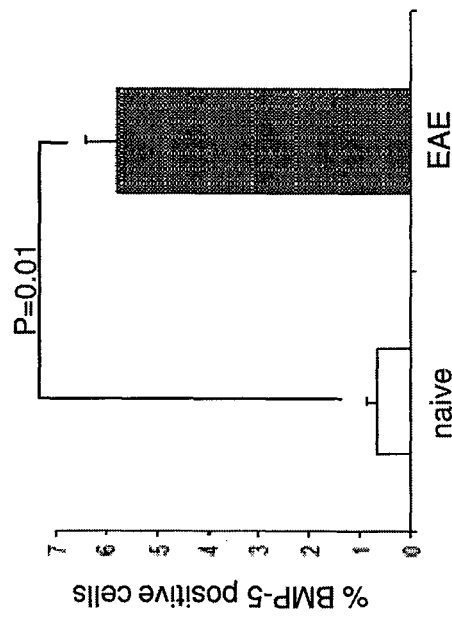
Figure 2P:
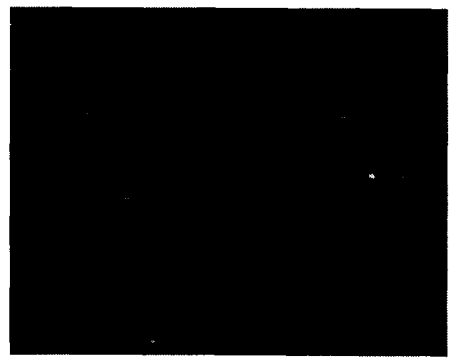
Figure 4:
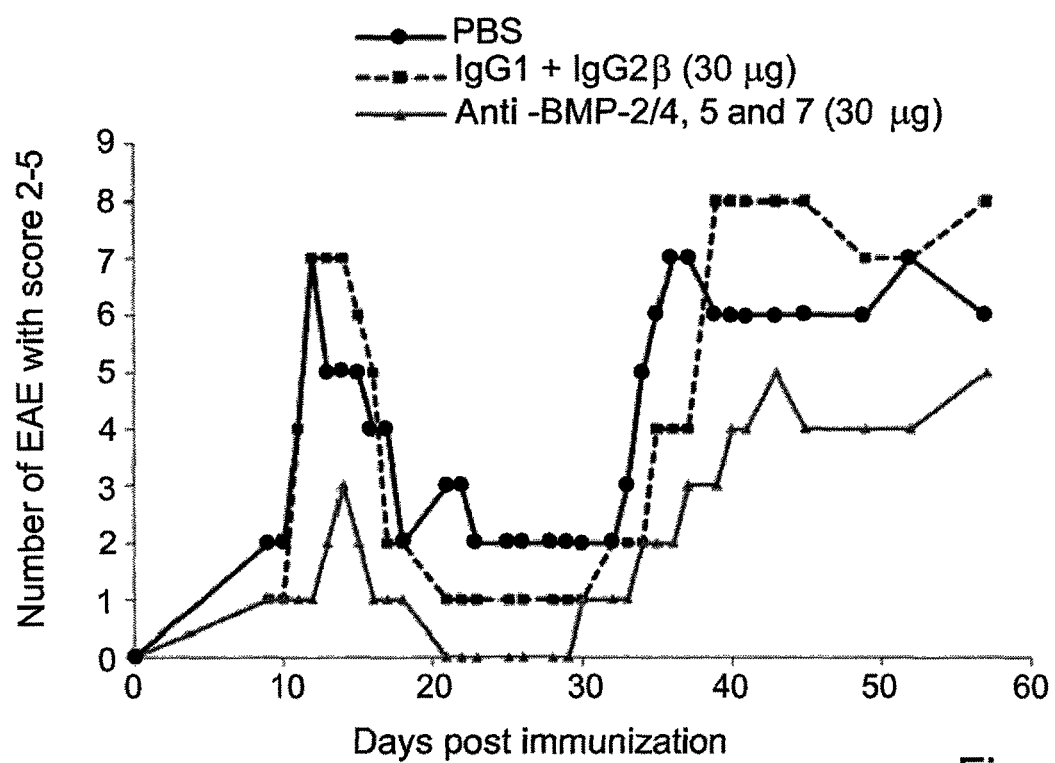
FIG. 4: A graphical representation of the clinical effect of 30 µg/mouse anti-BMPs neutralizing mAbs therapy in RR-EAE. The graph shows the number of mice which exhibit moderate and severe forms of the disease, with a clinical score of 2-5 (of subclass II). Abbreviations: EAE, Experimental autoimmune encephalomyelitis.

Although it was not induced in neuroproliferative zones per se, BMP-4 was induced in the VZ, adjacent to the DG (FIG. 2H and FIG. 2I, 14.3±2.4% in EAE mice vs. 0.5±0.1% in naïve mice, p=0.01) and in areas adjacent to the LV, the striatum and fimbria (FIG. 2K and FIG. 2L, 4.8±0.6% in EAE mice vs. 0.3±0.1% in naïve mice, p=0.01).

Figure 2Q:
Figure 2R:
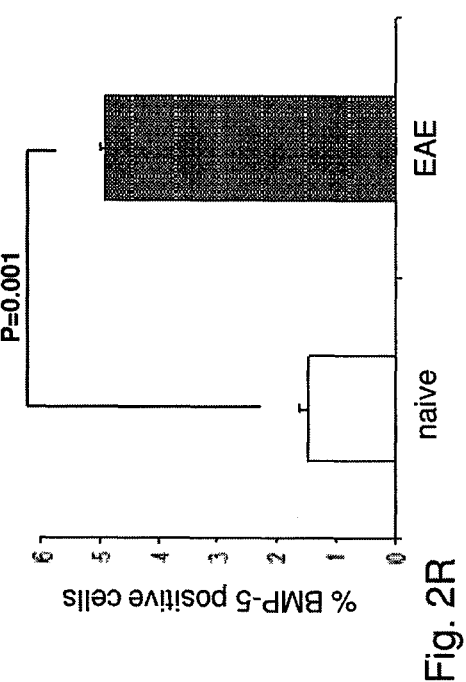
Figure 2S:
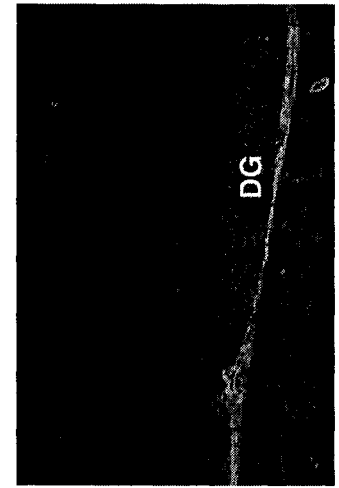
Figure 2T:
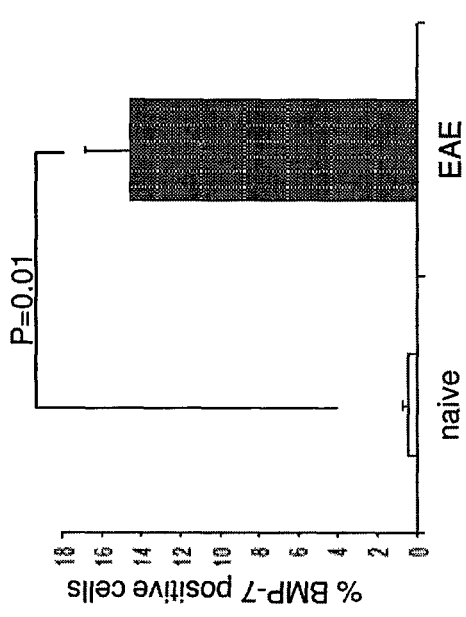
Figure 2U:
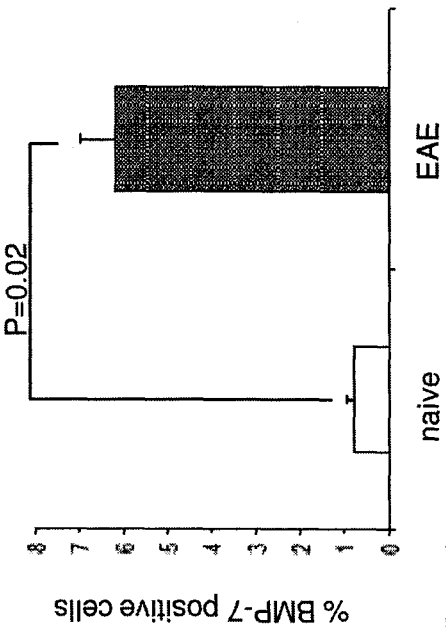
Figure 2V:

BMP-5 was induced in the VZ, adjacent to the DG (FIG. 2N and FIG. 2O, 5.8±0.6% in EAE mice vs. 0.6±0.2% in naïve mice, p=0.01), as well as in the SVZ, striatum and fimbria (FIG. 2Q and FIG. 2R, 4.9±0.1% in EAE mice vs. 1.4±0.1% in naïve mice, p=0.001).

Figure 2W:
Figure 2W:
Figure 2X:
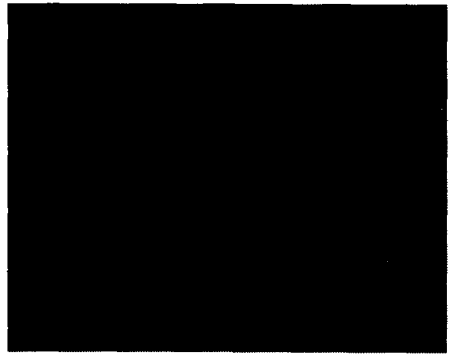

Similarly to BMP-4, BMP-7 was also induced only in areas adjacent to neuroproliferative zones: in the VZ adjacent to the DG (FIG. 2T and FIG. 2U, 14.6±2.3% in EAE mice vs. 0.5±0.2% in naïve mice, p=0.01), as well as in the striatum and fimbria (FIG. 2W and FIG. 2X, 6.1±0.8% in EAE mice vs. 0.8±0.1% in naïve mice, p=0.02).

Apparently, induction of RR-EAE leads to an increase in expression of BMPs in neuroproliferative brain areas.

Example 2

Systemic Administration of Antibodies Directed Against BMP 2, 4, 5 and 7 Ameliorates the Clinical Symptoms of RR-EAE As shown in Example 1, BMP-2, 4, 5 and 7 were found to be induced in neuroproliferative areas of RR-EAE mice. Example 2 demonstrates that blockage of BMP signaling by intravenous injection of anti-BMPs neutralizing mAbs ameliorates the symptoms of EAE. Without wishing to be bound by theory, the reduction in EAE symptoms may be the result of induction of both neurogenesis and oligodendrogenesis processes.

Accordingly, SJL female mice with induced RR-EAE were intravenously injected with a combination of 15 µg/mouse of each of the following mAbs: anti-human BMP-2/4, anti-human BMP-5 and anti-human BMP-7, on day 9 post induction of EAE, as detailed above. PBS-treated EAE mice (vehicle) and EAE mice treated with the corresponding isotype control antibodies (IC) served as negative controls. Animals were daily monitored for EAE symptoms and scored as described above. The monoclonal antibody Anti-BMP-2/4 recognizes an epitope that is present in both BMP-2 and BMP-4.

Figure 3A:
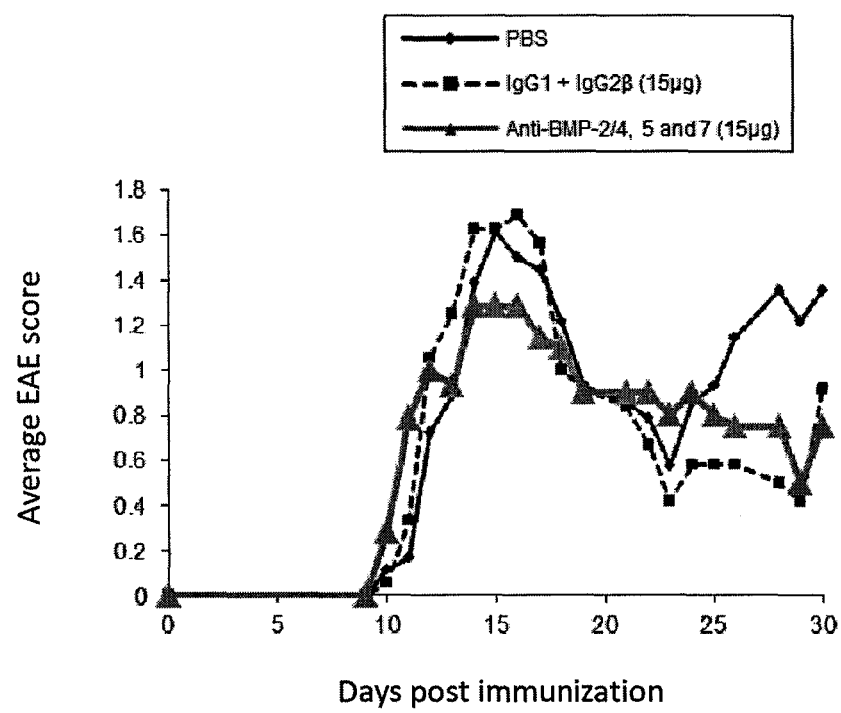
FIGS. 3A and 3B show the average clinical score of RR-EAE mice treated with 15 µg/mouse or 30 µg/mouse, respectively, of a combination of anti-human BMP-2/4, anti-human BMP-5 and anti-human BMP-7, on day 9 post immunization. PBS-treated EAE mice and isotype control (IC) namely, IgG1+IgG2β-treated EAE mice (15 µg/mouse or 30 µg/mouse, respectively) served as negative controls. The symbol * denotes p<0.05 as compared with IC and the symbol ** denotes p<0.05 as compared with vehicle (n=12 in each group). Abbreviations: EAE, Experimental autoimmune encephalomyelitis.

As shown in FIG. 3, clinical symptoms started to be displayed by all groups on day 10 post EAE induction. Although treatment of RR-EAE mice with anti-BMPs neutralizing antibodies at 15 µg/mouse slightly improved the average clinical score on day 15 post-EAE induction, this effect was found to be non significant (FIG. 3A, 1.28±0.18 in anti-BMPs mAb treated group as compared with 1.61±0.21 in untreated group, and 1.62±0.37 in IC treated group, p=NS, n=10 in each group). Thus, the concentration of each of the anti-BMPs mAbs that are administered to mice was increased to 30 µg/mouse.

Figure 3B:
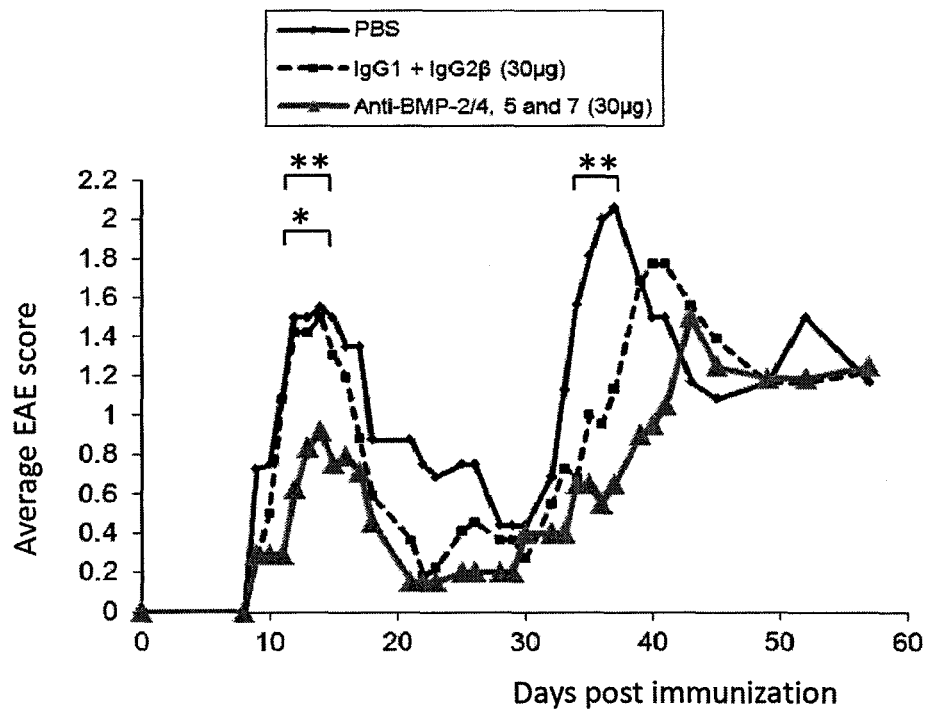

As demonstrated in FIG. 3B, treatment with 30 µg/mouse anti-BMP-2/4, 5 and 7 mAbs led to an improvement of 58.3% (vs. vehicle treatment) and 56.08% (relative to IC treatment) on day 12 post EAE induction (FIG. 3B, 0.62±0.18 in anti-BMPs treated mice vs. 1.5±0.33 in the vehicle-treated group and 1.42±0.19 in the IC-treated group, p=0.026 and p=0.007, respectively, n=12 in each group). This effect was maintained throughout the first relapse i.e. from day 12 until day 15 post EAE induction, in which anti-BMPs mAbs treated mice displayed a decline of 50% and 42.64% in average clinical score relative to vehicle-treated group and IC-treated group, respectively (0.75±0.2 in anti-BMPs treated mice vs. 1.5±0.21 in vehicle-treated group and 1.3±0.2 in IC-treated group, p=0.02 and p=0.05, respectively). Apparently, at each phase of the experiment the symptoms in the anti-BMPs treated mice were less severe than those in the controls.

In addition, in EAE mice, which have been treated with anti-BMPs mAbs (at 30 µg/mouse), the second relapse was delayed. The anti-BMPs mAbs-treated mice reached a maximal average score of 1.5±0.26 on day 43, whereas the vehicle-treated group reached a maximal average score of 2.06±0.43 on day 37 post immunization and the IC-treated group reached a maximal average score of 1.77±0.36 on day 40 (FIG. 3B).

The RR-EAE mice can be divided into two subclasses: subclass I, mice exhibiting a mild form of the disease, with a clinical score of 0-1.5; and subclass II, mice exhibiting moderate and severe forms of the disease, with a clinical score of 2-5.

FIG. 4 shows the number of mice in subclass II for each of the RR-EAE treated groups, namely, the anti-BMPs mAbs-treated mice, IC-treated and the PBS-treated RR-EAE mice (vehicle), evaluated daily for their clinical score. In the first relapse, the maximal number of RR-EAE mice in subclass II of the PBS-treated group was 7 (day 12). On day 12, there were also 7 mice in subclass II of the IC-treated group. Surprisingly, there was only one mouse in subclass II of the anti-BMPs treated group (n=13 in each group).

In addition, the first relapse observed for the anti-BMPs mAbs-treated mice was delayed to day 14, on which only 3 mice exhibited the moderate to severe form of the disease in the anti-BMPs group, compared to 5 and 7 mice in the PBS- and IC-treated groups, respectively. During the remission period, on days 21-29, none of the mice of the anti-BMPs group exhibited the moderate to severe form of the disease, i.e. there were no mice of the anti-BMPs group in subclass II.

Furthermore, FIG. 4 demonstrates that in the anti-BMPs mAbs-treated mice, the second relapse was delayed to day 43, on which there were 5 mice in subclass II, compared to days 36 and 39 in the PBS- and the IC-treated groups, in which subclass II contained 7 and 8 mice, respectively.

Therefore, it can be concluded that anti-BMPs neutralizing mAbs affect both the severity and the onset of the relapses of the disease in RR-EAE model.

Example 3

Administration of Anti-BMPs Neutralizing Antibodies to Chronic EAE Mice

Figure 5:
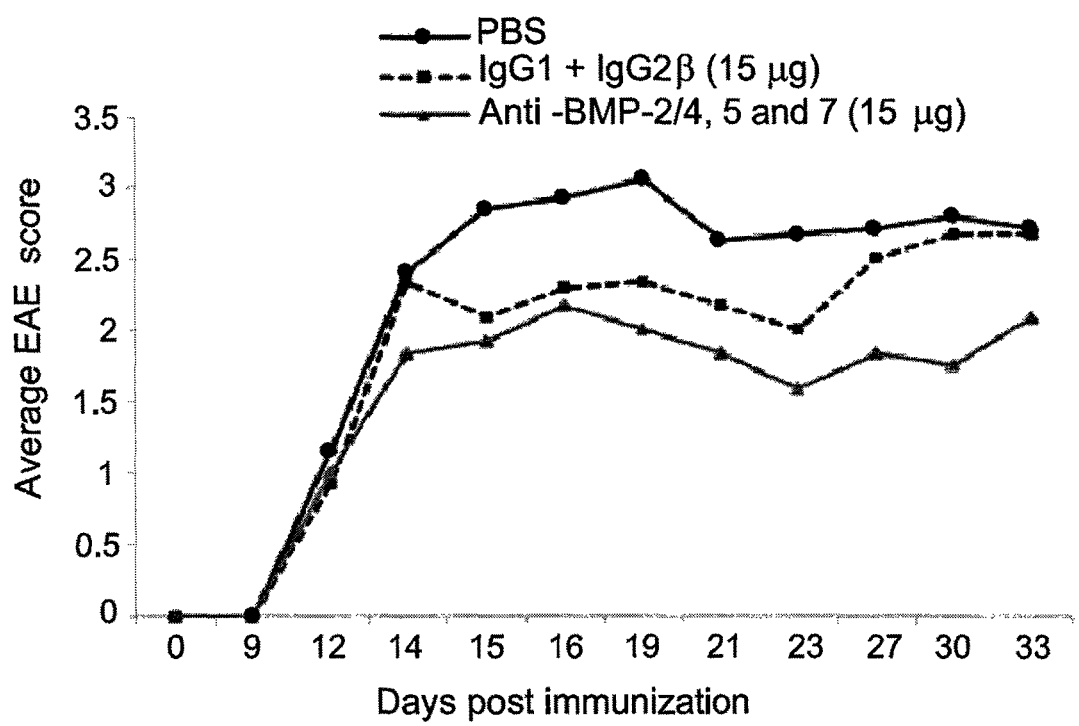
FIG. 5: A graphical representation of the clinical effect of 15 µg/mouse anti-BMPs neutralizing mAbs therapy in progressive EAE Vehicle (PBS)-treated RR-EAE mice and IC (IgG1+IgG2β)-treated EAE mice served as negative controls (n=10 in each group). Abbreviations: EAE, Experimental autoimmune encephalomyelitis.

The effect of anti-BMPs mAbs on chronic (progressive) EAE mice is demonstrated in FIG. 5. Chronic EAE was induced in C57BL/6 female mice by $MOG_{35-55}$ peptide immunization, as described above. As shown in FIG. 5, the onset of EAE clinical symptoms in C57BL/6 mice started on day 12 for all the groups presented.

Interestingly, treatment of C57BL/6 EAE mice with anti-BMPs mAbs (at 15 μg/mouse) resulted in a decline of 23.7% and of 21.4% in the average clinical score on day 14 vs vehicle-treated group and IC-treated group, respectively (1.83±0.46 in the anti-BMPs treated group vs 2.4±0.29 in vehicle-treated group and 2.3±0.24 in IC treated group). This effect was maintained until day 33 post induction, in which the anti-BMPs treated group displayed a decline of 23.2% and of 21.8% in the average clinical score relative to vehicle-treated group and IC-treated group, respectively.

Example 4

Levels of BMP-2, 4, 5 and 7 are Reduced in Neuroproliferative Areas in Response to Systemic Treatment with Anti-BMPs mAbs As shown in Example 2, the anti-BMPs mAbs treatment of RR-EAE mice resulted in a beneficial clinical effect. This Example shows that the levels of the BMPs 2, 4, 5 and 7 in neuroproliferative areas of the CNS of RR-EAE mice are reduced in response to the above treatment.

As indicated above, on day 9 post RR-EAE induction, RR-EAE mice were administered an intravenous injection of a combination of anti-BMP-2/4, 5 and 7 neutralizing mAbs (30 μg/mouse). As shown in FIG. 1, detection of BMPs 2, 4, 5 and 7 in EAE mice was performed on day 18 post immunization. Interestingly, on 18 days post RR-EAE induction, a significant decrease in the levels of all the examined BMPs was observed in anti-BMPs mAbs treated EAE mice, compared to IC-treated EAE mice. In addition, the resulting BMPs levels were similar to those observed in naïve mice.

Figure 6A:
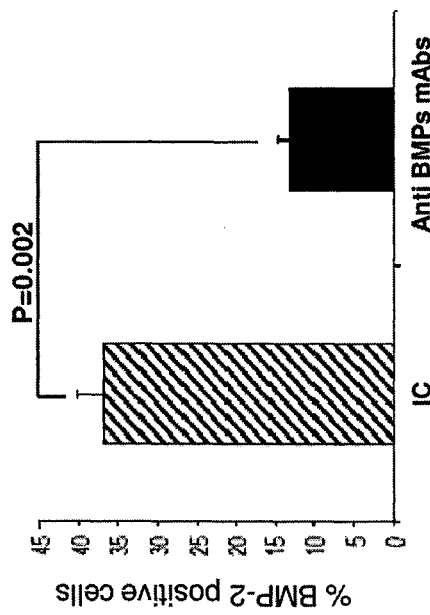
FIGS. 6A and 6D show the corresponding IC-treated EAE group. Fluorescent micrographs of sections of hippocampus and lateral ventricle areas (respectively) of EAE mice treated with the above combination of antibodies, stained with anti-BMP-4 antibodies are shown in FIGS. 6H and 6K, respectively (IC, FIG. 6G and FIG. 6J), with anti BMP-5 antibodies are shown in FIG. 6N and FIG. 6Q, respectively (IC, FIG. 6M and FIG. 6P) and with anti BMP-7 antibodies are shown in FIG. 6T and FIG. 6W, respectively (IC, FIG. 6S and FIG. 6V). Scale bar is 500 μm.
Figure 6B:
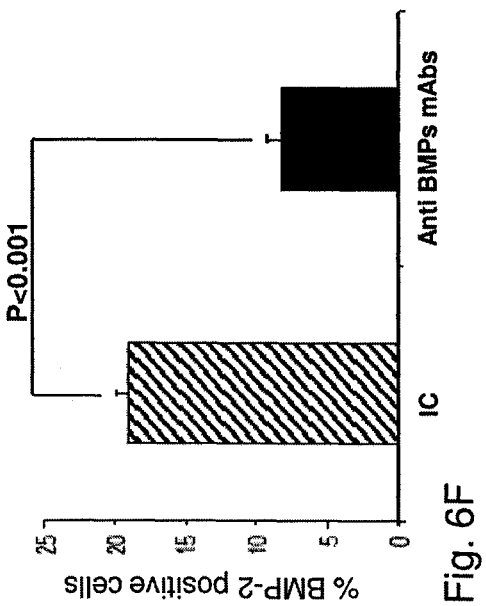
FIG. 6B and FIG. 6E show fluorescent micrographs of sections of hippocampus and lateral ventricle areas (respectively), stained with anti BMP-2 antibodies, of EAE mice systemically treated with 30 µg/mouse anti-BMP-2, 4, 5 and 7 neutralizing mAbs on day 9 post RR-EAE induction.
Figure 6D:
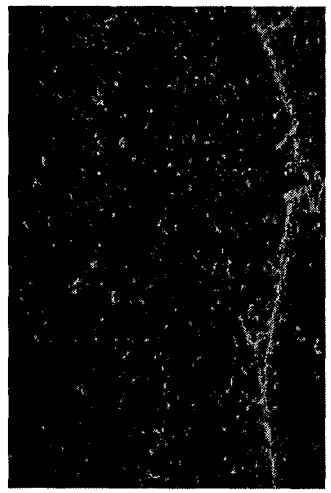
Figure 6C:
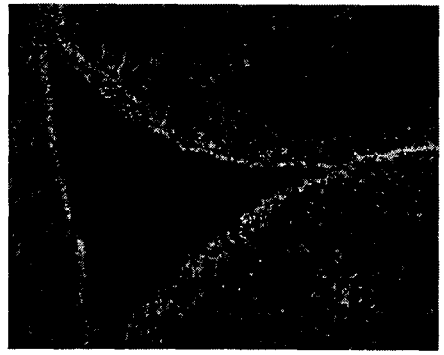
FIGS. 6C, 6F, 6I, 6L, 6O, 6R, 6U and 6X show quantification of the percentage of BMPs positive cells, performed on three sections obtained from three mice of each group, using ImageJ software.
Figure 6E:
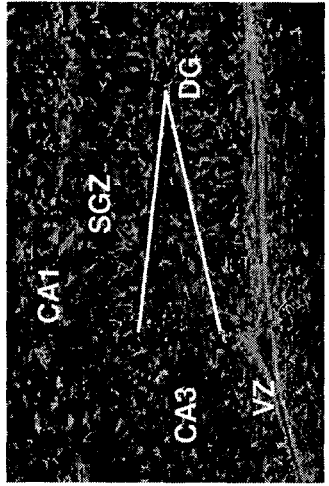
Figure 6F:
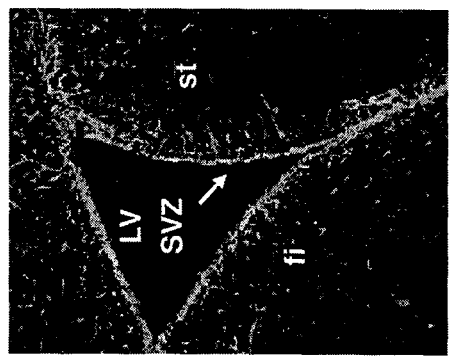
Figure 6I:
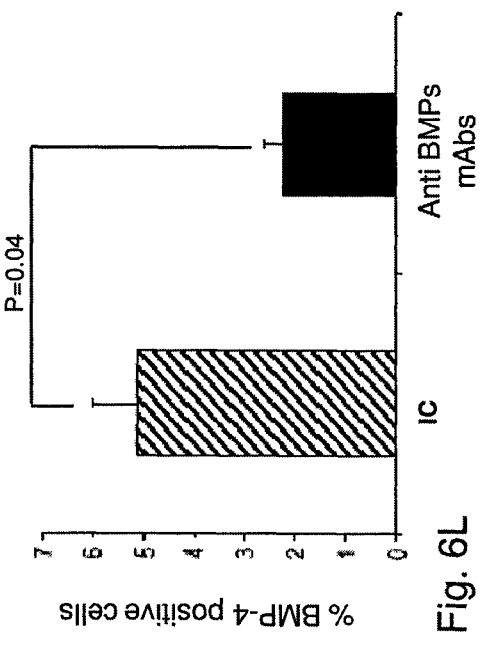
Figure 6L:
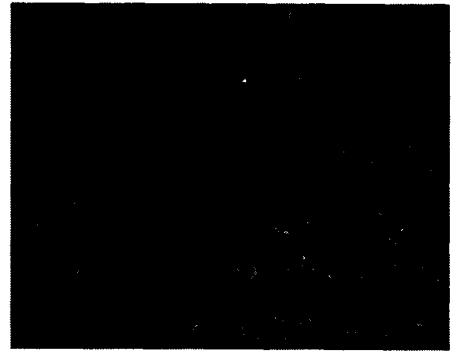
Figure 6H:
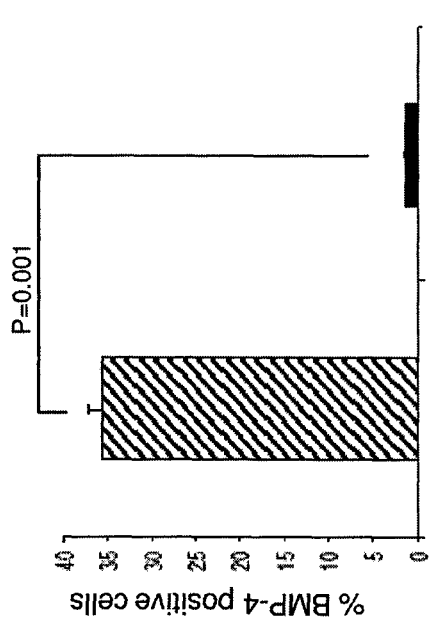
FIG. 6: Graphical representations of reduction in the levels of BMP-2, 4, 5 and 7 in neuroproliferative areas.
Figure 6K:
Figure 6G:
Figure 6J:
Figure 6S:
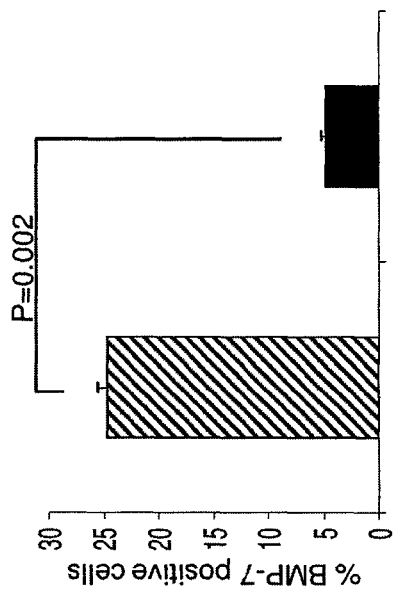
Figure 6T:
Figure 6U:
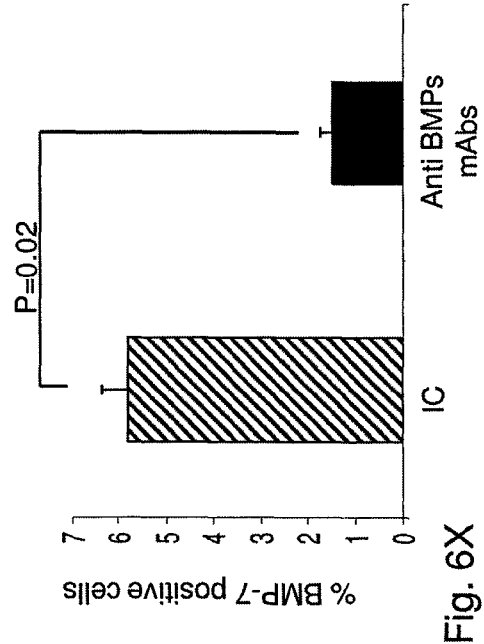
Figure 6V:
Figure 6W:
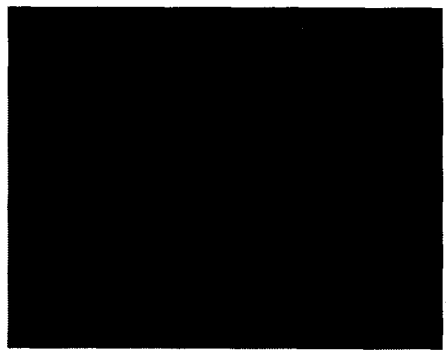
Figure 6X:

As shown in FIG. 6C and FIG. 6F, the levels of BMP-2 were reduced both in the SGZ of the DG and in the VZ adjacent to the DG (FIG. 6C, 13.1±1.6% in anti-BMPs treated mice vs. 36.9±3.1% in IC treated mice, p=0.002), as well as in the SVZ of the LV (FIG. 6F, 8.1±1.1% in anti-BMPs treated mice vs. 18.9±0.8% in IC treated mice, p<0.001).

Consistent with the fact that the most substantial increase in BMP-4, 5 and 7 was observed in the VZ adjacent to the DG (of the hippocampus), in EAE mice compared to naïve mice (as shown in FIG. 2), the most substantial decrease in these BMPs was observed in the VZ of anti-BMPs treated mice as compared to the IC treated mice. As demonstrated in FIG. 6I, the level of BMP-4 was substantially reduced in the VZ adjacent to the DG (FIG. 6I, 1.5±0.03% in anti-BMPs treated mice vs. 35.6±1.4% in IC treated mice, p=0.001) and slightly reduced in areas adjacent to the LV, striatum and fimbria (FIG. 6L, 2.2±0.3% in anti-BMPs treated mice vs. 5.1±0.8% in naïve mice, p=0.04).

Similarly, the levels of BMP-5 and BMP-7 were reduced in the VZ, adjacent to the DG (BMP-5. FIG. 6O, 2.1±0.2% in anti-BMPs treated mice vs. 8.1±0.2% in IC treated mice, p=0.003; BMP-7, FIG. 6U, 4.7±0.4% in anti-BMPs treated mice vs. 24.6±0.8% in IC treated mice, p=0.002), as well as in the striatum and fimbria (BMP-5, FIG. 6R, 1.6±0.5% in anti-BMPs treated mice vs. 7.7±1.1% in IC treated mice, p=0.03; BMP-7, FIG. 6X, 1.4±0.2% in anti-BMPs treated mice vs. 5.8±0.5% in IC treated mice, p=0.02).

Example 5

NeuN Induction in Response to Treatment with Anti-BMPs mAbs

A neuronal nuclear (NeuN) marker was used for detecting mature neurons in neuroproliferative zones as well as in areas, which are known to degenerate during RR-EAE.

Interestingly, a significant decrease in NeuN positive cells was observed in the granule cell layer (GCL) of vehicle-treated EAE mice, compared to naïve mice, on 18 days post immunization (FIG. 7A, FIG. 7B and FIG. 7E, 31.6±0.9% in vehicle treated-EAE mice vs. 48.1±0.2% in naïve, p=0.003).

Figure 7A:
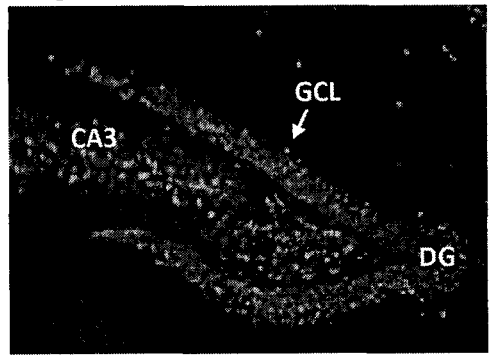
Figure 7B:
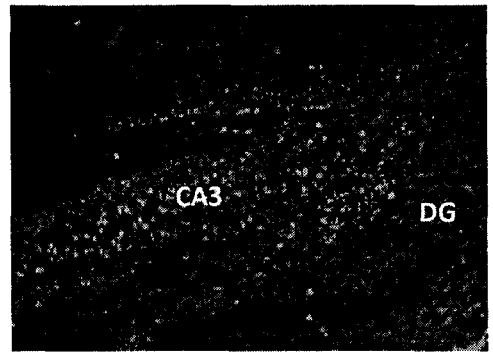
Figure 7C:
Figure 7D:
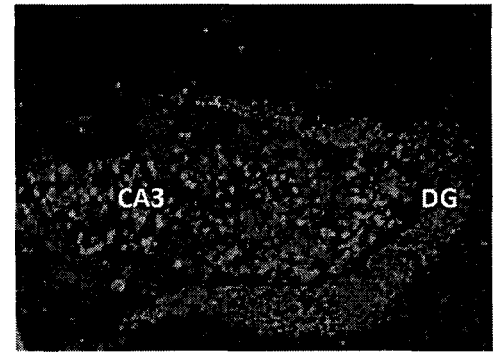
Figure 7E:
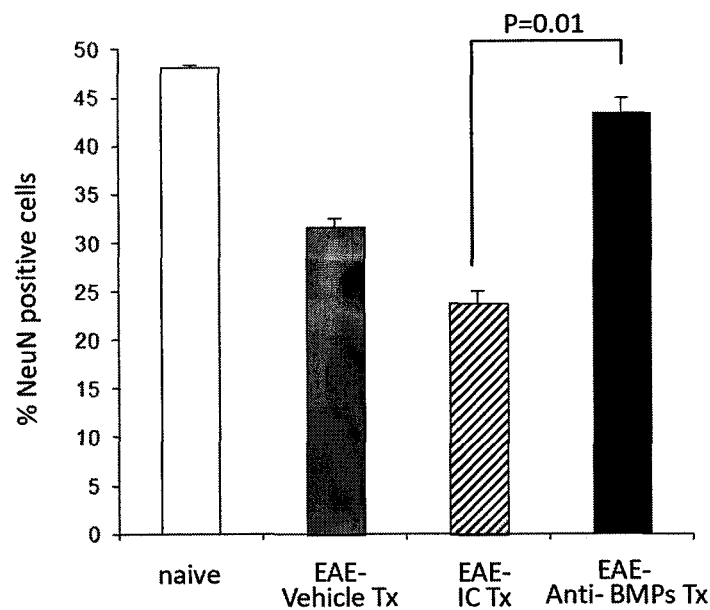

A similar decrease in the levels of NeuN in GCL was observed in IC treated EAE mice (FIG. 7E). Surprisingly, a significant increase in the levels of NeuN positive cells was observed in anti-BMPs mAbs-treated mice (30 μg/mouse), yielding NeuN levels in GCL that were similar to those observed in naïve mice (FIG. 7C, FIG. 7D and FIG. 7E, 43.3±1.6% in anti-BMPs treated EAE mice vs. 23.8±1.2% in IC treated EAE mice, p=0.01). Similar effects were also observed in the striatum and in the cortical layers. No NeuN was detected in the SVZ of LV in all the groups tested (FIGS. 7A1-D1).

Decreased levels of NeuN were observed in the striatum of vehicle-treated EAE-induced mice, compared to naïve mice (FIG. 7A1, FIG. 7B1 and FIG. 7E1, 8.7±0.5% in vehicle treated EAE mice vs. 19.5±0.9% in IC treated EAE mice, p=0.01). In contrast. NeuN levels were induced in anti-BMPs mAbs-treated mice, compared to IC-treated mice (FIG. 7C1, FIG. 7D1 and FIG. 7E1, 16.2±1.1% in anti-BMPs treated EAE mice vs. 9.9±0.3% in IC treated EAE mice, p=0.03). A significant reduction in NeuN positive cells was also observed in cortical layers of vehicle-treated EAE-induced mice, compared to naïve mice, primarily in cortical layer VII, adjacent to the corpus callosum (FIG. 7A2, FIG. 7B2 and FIG. 7E2, 11.7±0.1% in vehicle treated EAE mice vs. 16.9±0.2% in IC treated EAE mice, p=0.002).

Interestingly, NeuN was also induced in cortical layers of anti-BMPs mAbs treated mice, compared to IC treated mice, and primarily in cortical layer VII (FIG. 7C2, FIG. 7D2 and FIG. 7E2, 20.1±0.6% in anti-BMPs treated EAE mice vs. 9.9*0.1% in IC treated EAE mice, p=0.003).

Example 6

O4 Induction in Response to Treatment with Anti-BMPs mAbs

The oligodendrocyte marker O4 was used for detecting oligodendrocytes in neuroproliferative zones.

An increase in the number of O4 positive cells was observed in both the SGZ and the hilus of the DG, in vehicle-treated EAE mice compared to naïve mice (FIG. 8A, FIG. 8B and FIG. 8E, 14.8±0.9% in vehicle-treated EAE mice vs. 4.3±0.4% in naïve mice, p=0.01). Interestingly, an additional increase in the number of O4 positive cells was observed in anti-BMPs mAbs treated EAE mice, compared to the IC-treated EAE group, primarily in the hilus, suggesting that the treatment enhanced differentiation of SGZ progenitors to oligodendrocytes in the hilus (FIG. 8C, FIG. 8D and FIG. 8E, 26.5±1.3% in anti-BMPs treated EAE mice vs. 13.4±1.4% in IC treated EAE mice, p=0.02).

It has been reported that some type B cells in the SVZ and a small subpopulation of actively dividing type C (transit-amplifying) cells were found to express oligodendrocyte lineage transcription factor 2 (Olig2), indicating that oligodendrocytes differentiation may also begin in the SVZ [10]. As demonstrated in FIG. 8, while similar levels of O4 were observed in the SVZ of naïve, vehicle- and IC-treated EAE mice, a significant induction of O4 levels was observed in the SVZ of anti-BMPs mAbs-treated EAE mice, as compared to IC-treated EAE mice (FIG. 8A1-FIG. 8E1. 31.1±1.2% in anti-BMPs treated EAE mice vs. 8.5±1.1% in IC treated EAE mice, p=0.004).

Figure 8A:
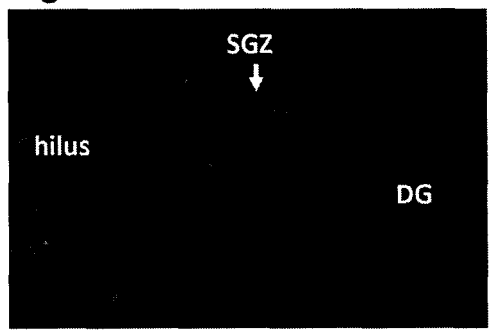
Figure 8B:
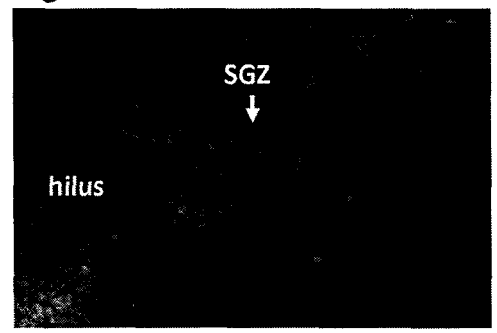
Figure 8C:
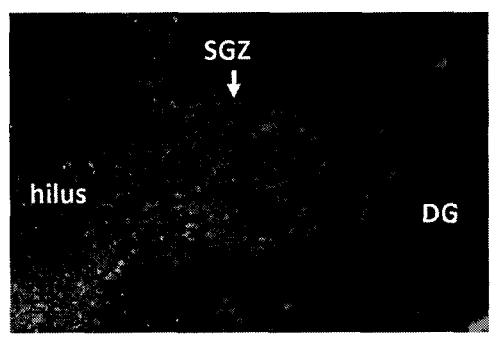
Figure 8D:
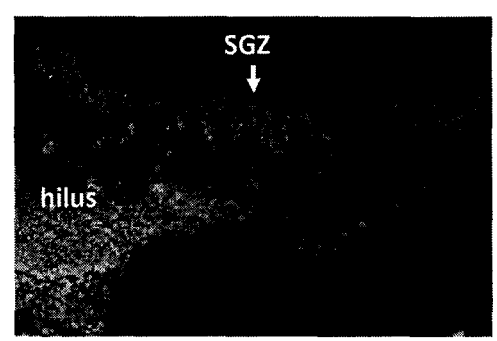
Figure 8E:
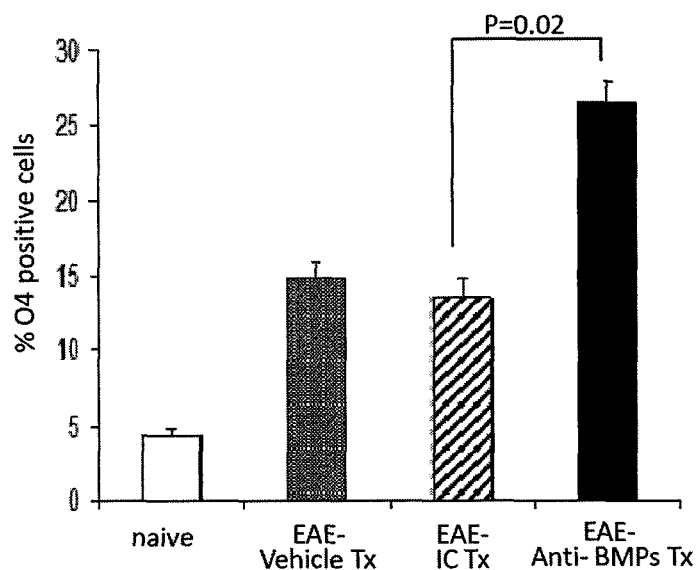

It is known that O4 may also be detected in the anterior commissure and the corpus callosum. Demyelination has been previously reported in the anterior commissure of $MOG_{35-55}$ induced EAE as well as in the corpus callosum of $PLP_{139-151}$ induced EAE. It is also known that Oligodendrocytes account for 86% of all neuroglial cell profiles in the anterior commissure. Interestingly, similar levels were observed for O4 in the anterior commissure of naïve mice (FIG. 8A1, 89.7±7.5%). A non significant trend for down-regulation of O4 in vehicle-treated EAE mice as compared to naïve nice was observed (FIG. 8B1. FIG. 8F1, 67.2±0.8% in vehicle treated EAE mice, p=NS). However, there was a significant induction in the levels of O4 in the anterior commissure of anti-BMPs mAbs treated EAE mice, compared to the IC treated mice (FIG. 8C1, FIG. 8D1 and FIG. 8F1, 90.1±4.3% in anti-BMPs treated EAE mice vs. 64.7±0.7% in IC treated EAE mice, p=0.03).

Similarly, a reduced level of O4 was observed in the corpus callosum of vehicle-treated EAE mice, compared to naïve mice (FIG. 8A2, FIG. 8B2 and FIG. 8E2, 71.5±2.3% in corpus callosum of vehicle treated EAE mice vs. 91.1±1.5%, p=0.02), and a significant induction in the level of O4 in the corpus callosum of anti-BMPs-treated EAE mice (compared to IC-treated EAE mice) was observed (FIG. 8C2, FIG. 8D2 and FIG. 8E2, 87.9±1.8% in anti-BMPs treated EAE mice vs. 73.8±1.8% in IC treated EAE, p=0.02).

Example 7

GFAP Levels are Reduced in Neuroproliferative Zones in Response to Anti-BMPs mAbs Treatment The glial fibrillary acidic protein (GFAP) marker was used for detecting neural stem cells (NSCs). In order to distinguish between GFAP$^+$ mature astrocytes and GFAP$^+$ neural stem cells (NSCs), three mice of each group were also daily intraperitoneally injected with bromo-2'-deoxyuridine (BrdU), a thymidine analog, which is incorporated into the DNA of dividing cells, starting from day 9 post immunization. BrdU$^+$ cells in the neurproliferative niches represent proliferating NSCs, in contrast to GFAP$^+$BrdU$^-$, which represent more mature astrocytes.

As demonstrated in FIG. 9, a higher number of total GFAP positive cells was observed in the DG of vehicle-treated EAE mice, compared to naïve mice (FIG. 9A, FIG. 9B and FIG. 9E, 15.1±0.3% in vehicle treated EAE mice vs. 6.1±0.7% in naïve mice, p=0.007), concomitant with an increased level of BrdU cells in the SGZ (FIG. 9A, FIG. 9B and FIG. 9F, 1.6±0.1% in vehicle treated EAE mice vs. 0.6±0.02% in naïve mice, p=0.02), consistent with previous reports regarding the induction of neural stem cells (NSCs) proliferation in neuroproliferative niches of EAE induced mice [10].

However, no significant differences were found in the levels of BrdU positive cells in anti-BMPs treated EAE mice, compared to IC treated mice. Without wishing to be bound by theory, these results indicate that BMP inhibition probably does not significantly affect NSCs proliferation (FIG. 9C, FIG. 9D and FIG. 9F, 1.5±0.1% in anti-BMPs treated EAE mice vs. 1.6±0.3% in IC treated EAE mice, p=NS). Nonetheless, there was a significant reduction in GFAP positive cells in response to anti-BMPs mAbs treatment (FIG. 9C, FIG. 9D and FIG. 9E, 8.1±1.1% in anti-BMPs treated EAE mice vs. 19.8±1.1% in IC treated EAE mice, p=0.02).

A similar effect, and even more pronounced, was observed in SVZ. There was a significant increase in both BrdU positive cells and GFAP positive cells in the SVZ of vehicle-treated EAE mice, compared to naïve mice (FIG. 9A1, FIG. 9B1, FIG. 9H1 and FIG. 9I1, BrdU, 8.2±0.9% in vehicle treated EAE mice vs. 1.1±0.7% in naïve mice, p=0.02, and GFAP, 18.8±1.1% in vehicle treated EAE mice vs. 11.9±0.5% in naïve mice, p=0.03).

Most of the BrdU positive cells in the SVZ of vehicle-treated EAE mice were also positive to GFAP, i.e. exhibiting a classic stem cell phenotype, as demonstrated in FIG. 9E1. Although anti-BMPs mAbs treatment did not affect stem cells proliferation in the niche as measured by BrdU levels (FIG. 9C1, FIG. 9D1 and FIG. 9I1, 7.3±0.2% in anti-BMPs treated EAE mice vs. 7.2±1.1% in IC treated EAE mice, p=NS), anti-BMPs mAbs treatment significantly reduced the number of total GFAP positive cells in the SVZ (FIG. 9C1, FIG. 9D1 and FIG. 9H1, 13.3±0.8% in anti-BMPs treated EAE mice vs. 22.7±0.9% in IC treated EAE mice, p=0.02). As demonstrated in FIG. 9F1 and FIG. 9G1, while most of the BrdU positive cells of IC treated mice were also positive to GFAP, similarly to vehicle-treated mice, most of the BrdU positive cells in anti-BMPs mAbs treated mice were negative for GFAP expression. This finding suggests that proliferating precursors cells in the SVZ of anti-BMPs mAbs treated mice are probably more differentiated to exhibit neuronal or oligodendroglial phenotype.

Example 8

Anti-BMP-2/4 mAb is Effective in Ameliorating the Clinical Symptoms of RR-EAE

Next, the effect of each of the antibodies as a monotherapy was examined. Accordingly, each of the mAbs (anti-BMP-2/4 mAb, anti-BMP-5 mAb or anti-BMP-7 mAb) was administered as a single agent (i.v.) to RR-EAE mice groups, at 30 µg/mouse. IgG1-treated mice were used as controls for anti-BMP-2/4 mAb therapy, whereas IgG2β-treated mice served as controls for both the anti-BMP-5 and for the anti-BMP-7 mAbs.

Figure 10A:
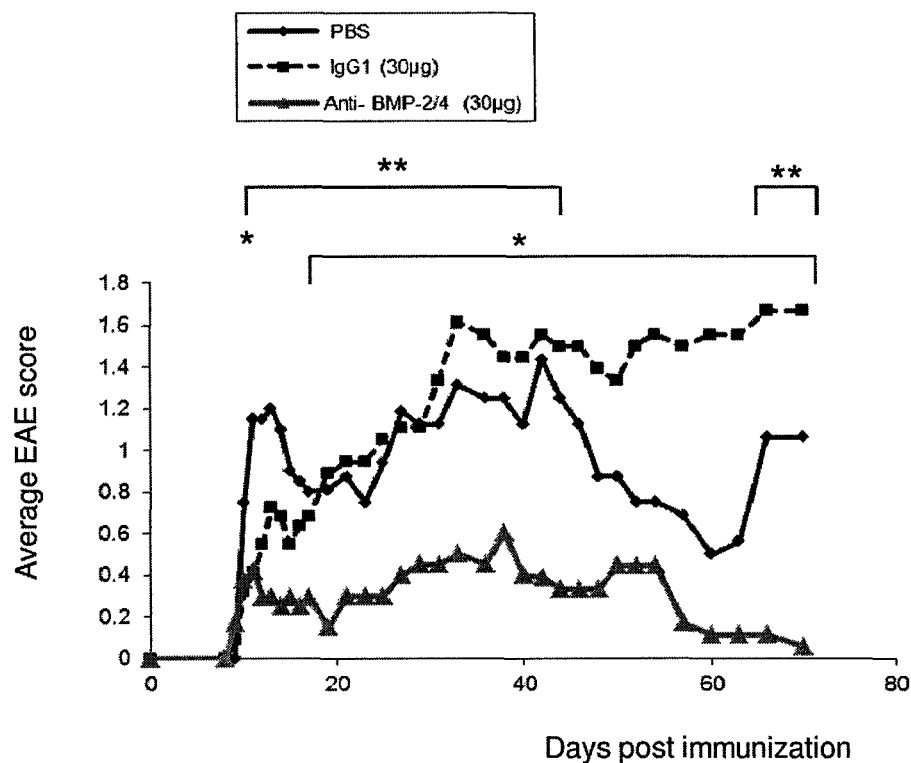
FIG. 10A shows the average clinical score of RR-EAE induced mice treated with 30 μg/mouse of anti-BMP-2/4 antibody or the corresponding IC (IgG1, 30 μg/mouse).

Unexpectedly, treatment with 30 µg/mouse of anti-BMP-2/4 mAb as a single therapy was more effective in ameliorating the symptoms of RR-EAE than the combined treatment of anti-BMP-2/4, 5 and 7 mAbs altogether (FIG. 10A). As demonstrated in FIG. 10A, treatment with anti-BMP-2/4 mAb as a single agent led to an improvement of 77.27% with respect to the vehicle treatment and 63.33% relative to IgG1 treatment on day 14 post RR-EAE induction (FIG. 10A, 0.25±0.09 in anti-BMP-2/4 treated EAE mice vs 1.1±0.26 in the vehicle-treated group and 0.68±0.16 in the IgG1-treated group, p=0.004 and p=0.03, respectively, n=12 in each group). This effect was maintained throughout the experiment period, until an improvement of 89.54% vs vehicle treatment and 93.33% relative to IgG1 treatment was observed on day 66 post immunization. (0.11±0.09 in anti-BMP-2/4 treated EAE mice vs. 1.06±0.31 in the PBS-treated group (vehicle) and 1.66±0.27 in the IgG1-treated group, p=0.01 and p=0.0001, respectively). As demonstrated in FIG. 10B, neither the treatment with anti-BMP-5 mAb, nor with the anti-BMP-7 mAb, had a significant effect on EAE symptoms, compared to the control groups.

Figure 10B:
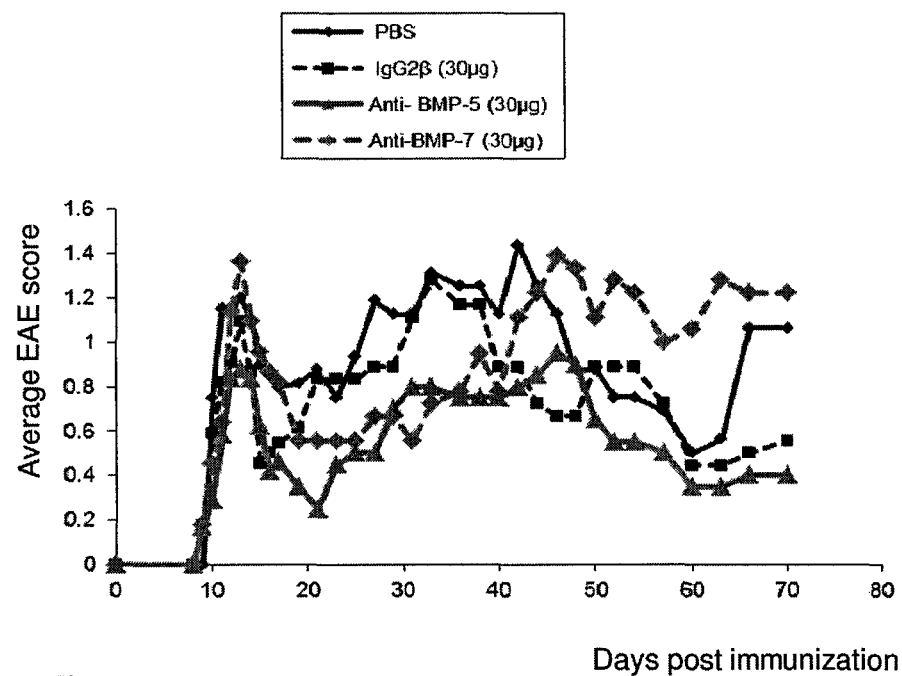
FIG. 10B shows the average clinical score of RR-EAE induced mice treated with anti-BMP-5 or anti-BMP-7 and their corresponding IC (IgG2β, 30 μg/mouse). The symbol * denotes p<0.05 as compared with IC and the symbol ** denotes p<0.05 as compared with vehicle (n=12 in each group). Abbreviations: EAE, Experimental autoimmune encephalomyelitis.

As demonstrated in FIG. 10B, it should be noted that a slight, but not statistically significant, trend for an aggravation in RR-EAE symptoms in mice treated with anti-BMP-7 alone has been observed, in the first relapse on day 13, and from day 46 to day 66, compared to vehicle-treated and IgG23-treated mice (FIG. 10B).

Example 9

An Increased Number of Neuroblasts is Found in the Neuroproliferative Niches of Relapsing-Remitting EAE (RR-EAE), in Response to Blockage of BMP-2/4 Signaling As indicated in Example 7 above, stem cells in the neuroproliferative zones are known to express the glial fibrillary acidic protein (GFAP) marker, similar to mature astrocytes. Upon initial differentiation towards neuroblasts these cells acquire the microtubule-associated protein doublecortin (DCX). Further to studying the effect of treatment with anti-BMPs 2, 4, 5 and 7 antibodies on neural stem cells differentiation and proliferation in various brain sections of RR-EAE mice, the effect of treatment with anti-BMP-2/4 mAb antibodies, as a monotherapy, was also examined as detailed below.

RR-EAE was induced in SJL female mice as detailed above. Mice were intravenously injected with 30 µg/mouse of either mouse anti-human BMP-2/4, or the corresponding isotype control, IgG1, on day 9 post immunization. For immunohistochemical analysis, 3 mice of each group were daily intraperitoneally injected with bromo-2'-deoxyuridine (BrdU) starting from day 9 post immunization for 8 following days.

Figure 11I:
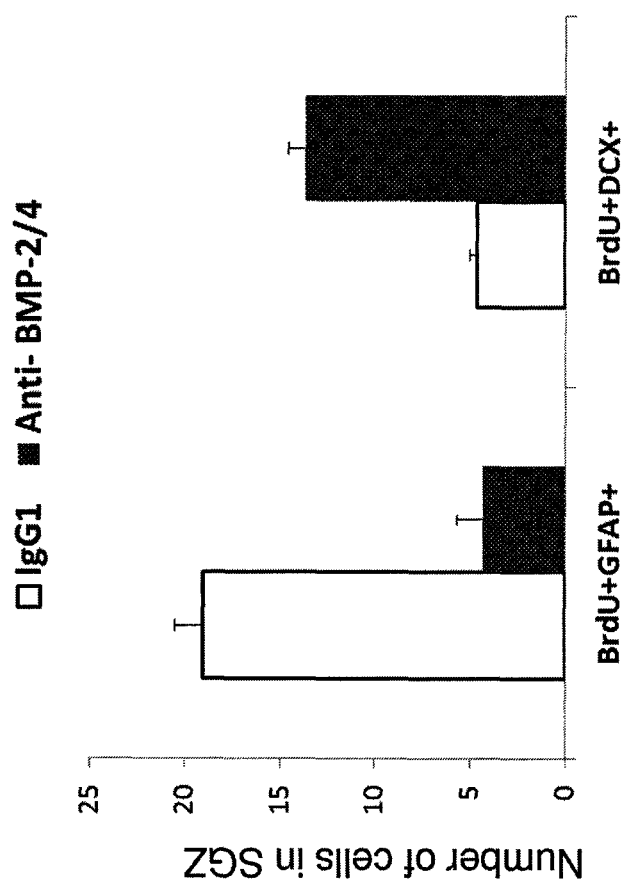
FIG. 11I is a graphical representation of quantification of the results presented in FIGS. 11A, 11C, 11E and 11G (scale bar=100 μm). Quantification was performed by analyzing 3 sections from each mouse, 3 mice from each group, total N=9 (FIG. 11I). Coronal sections, images were obtained by a confocal microscopy. Abbreviations: SGZ, subgranular zone.

As demonstrated in FIG. 11A-D and in FIG. 11I, reduced numbers of BrdU$^+$GFAP$^+$ stem cells were detected, but not reduced numbers of BrdU*GFAP cells, in the subgranular zone (SGZ) of the dentate gyrus in RR-EAE induced mice, treated with anti-BMP-2/4 mAb, compared to IgG1-(the corresponding isotype control) treated RR-EAE mice (4.3±1.3 in anti-BMP-2/4 mAb group vs. 19.0±1.5 in IgG1 group, p=0.0007). This finding suggests that BMP-2/4 blockage enhanced stem cells differentiation, and had no effect on stem cells proliferation, consistent with the results presented above.

Analyzing the DCX marker in the SGZ revealed that most of the BrdU$^+$GFAP$^-$ cells in the SGZ of anti-BMP-2/4 mAb treated mice were positive to DCX. Indeed, enhanced numbers of BrdU$^+$DCX$^+$ cells were observed in the SGZ of anti-BMP-2/4 group, compared to IgG1 group, suggesting that blockage of BMP-2/4 signaling significantly amplified stem cells acquisition of neuronal phenotype in the SGZ (13.6±0.8 in anti-BMP-2/4 mAb group vs. 4.6±0.3 in IgG1 group, p=0.004, FIG. 11E-FIG. 11I).

Further to the results presented above for the subgranular zone (SGZ) of the dentate gyrus in RR-EAE induced mice, similar findings were observed in subventricular zone (SVZ) of the lateral ventricle. As demonstrated in FIG. 12A, FIG. 12B and FIG. 12E, reduced numbers of BrdU$^+$GFAP$^+$ stem cells, but not reduced numbers of BrdU$^+$GFAP$^+$ cells, were detected in the SVZ of RR-EAE induced mice, treated with anti-BMP-2/4 mAb, compared to IgG1-treated RR-EAE mice (4.0±0.5 in anti-BMP-2/4 mAb group vs. 29.7±4.9 in IgG1 group, p=–0.03). In addition, elevated numbers of BrdU$^+$DCX$^+$ cells were observed in the SVZ of anti-BMP-2/4 group, compared to IgG1 group, supporting that blockage of BMP-2/4 signaling enhanced neurogenesis rate also in the SVZ (34.0±2.1 in anti-BMP-2/4 mAb group vs. 9.6±0.8 in IgG1 group, p=0.002, FIG. 12C, FIG. 12D and FIG. 12E).

Example 10

Elevated Numbers of BrdU$^+$NeuN$^+$ Cells in Striatum and Cortical Layers of Anti-BMP-2/4 mAb Treated Mice It has been previously reported that projecting neurons in cortical layers II/III, V and VII are highly sensitive to the neurodegenerative processes associated with MS and EAE. Further to the results presented in Example 5 above, demonstrating NeuN induction in response to treatment with anti-BMPs mAbs, the effect of anti-BMP-2/4 mAb as a monotherapy on neural stem cells differentiation using the NeuN marker was also examined.

Immunohistochemical labeling of BrdU and NeuN was performed as described above in striatum and in cortical layers of IgG1- and anti-BMP-2/4 mAb treated EAE mice, on day 18 post immunization.

Figure 13B:
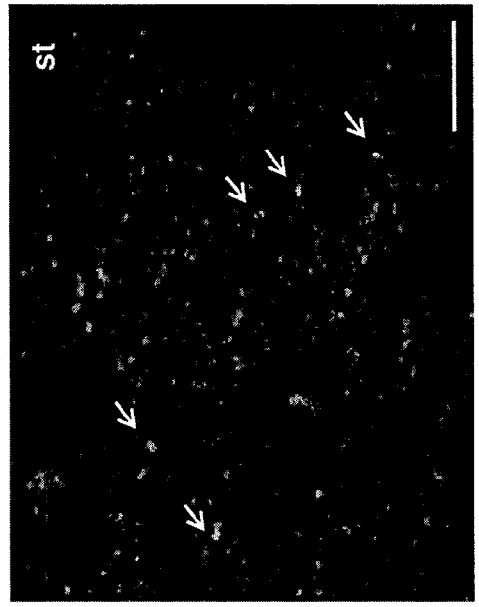
FIG. 13: Graphical representations of elevation in the numbers of $BrdU^+NeuN^+$ cells in striatum and cortical layers of anti-BMP-2/4 mAb treated mice. Immunohistochemical labeling of BrdU and NeuN is shown in striatum (FIG. 13A) and in cortical layers (FIG. 13C) of IgG1-treated EAE mice on day 18 post immunization. De novo $BrdU^+NeuN^+$ cells were detected upon Immunohistochemical labeling as indicated above in striatum (FIG. 13B) and in cortical layers (FIG. 13D) of anti-BMP-2/4 mAb treated EAE mice (FIG. 13B, scale bar=100 μm). Arrows indicate only double positive cells.
FIG. 13E is a graphical representation of the quantification of the results presented in FIGS. 13A-D, performed by analyzing 3 sections from each mouse, 3 mice from each group, total N=9. Coronal sections images were obtained by a confocal microscopy. Abbreviations: st, striatum; cl, cortical layers; cc, corpus callosum.
Figure 13D:
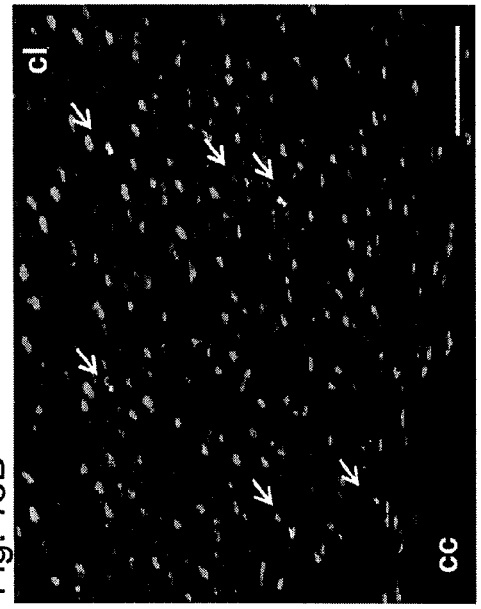
Figure 13A:
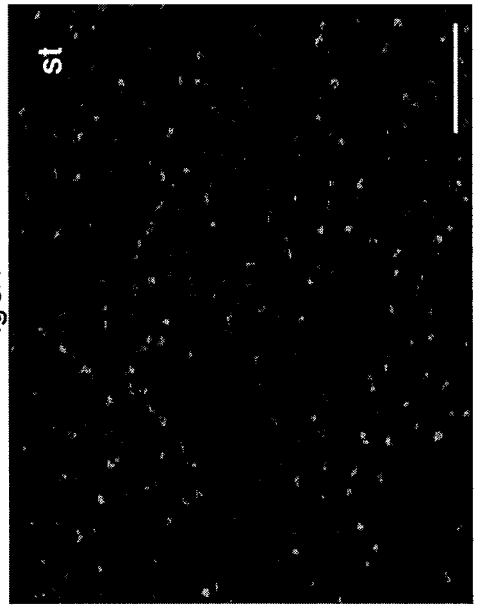
Figure 13C:
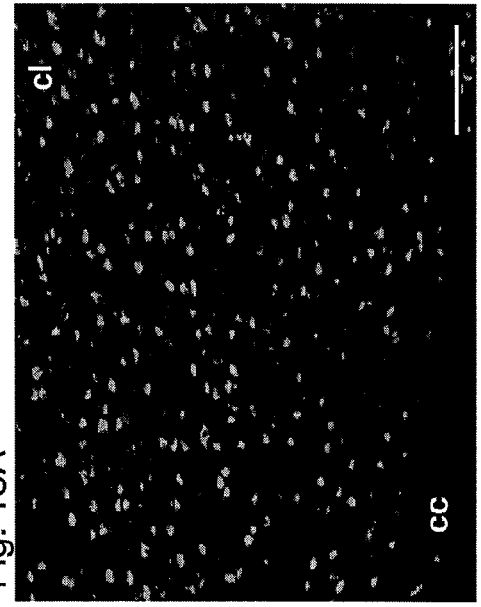
Figure 13E:
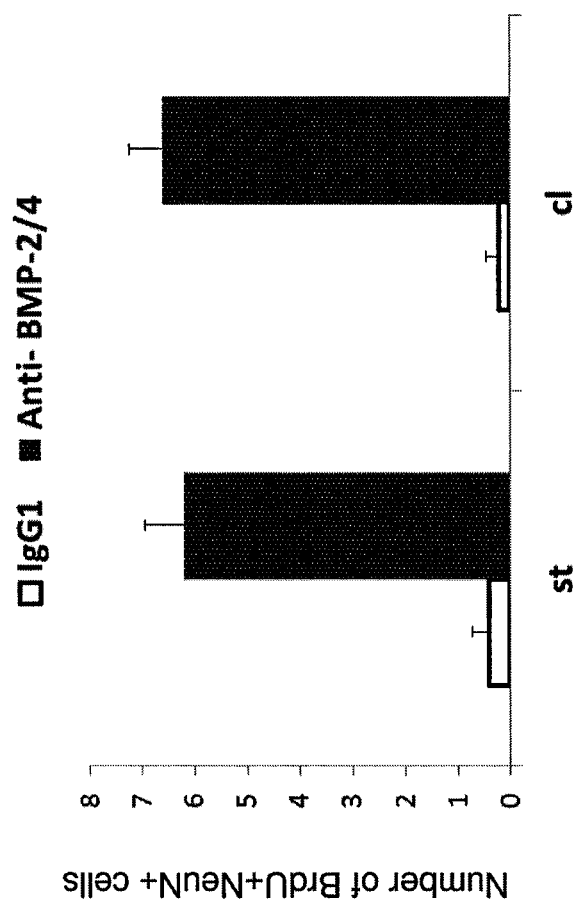

As shown in FIG. 13, de novo mature neurons expressing both BrdU and NeuN could hardly be detected in striatum and conical layers of IgG1-treated EAE mice on day 18 post immunization (FIG. 13A and FIG. 13C). However, substantial numbers of BrdU$^+$NeuN$^+$ cells could be detected in both striatum and conical layers of anti-BMP-2/4 mAb treated EAE mice, indicating that BMP-2/4 blockage enhanced neural stem cells differentiation into mature neurons with a capacity to migrate into neurodegenerative areas in EAE (FIG. 13B and FIG. 13D). A quantification of these results, showing the number of BrdU$^+$NeuN$^+$ cells in the in striatum and cortical layers of IgG- and anti-BMP-2/4 treated EAE is presented in FIG. 13E.

Example 11

Enhanced Numbers of De Novo Oligodendrocytes in Corpus Callosum and in Hippocampal Lesion in Response to BMP-2/4 Blockage As shown in Example 6 above, an induction in the O4 marker was observed in response to treatment with anti- BMPs mAbs. The results provided below demonstrate the effect of treatment with anti-BMP-2/4 mAb as a monotherapy on oligodendrocyte differentiation. The O4 marker was used in order to detect oligodendrocytes late progenitors in the corpus callosum, which is known to be highly sensitive to demyelination and oligodendrocytes loss in EAE.

Figure 14E:
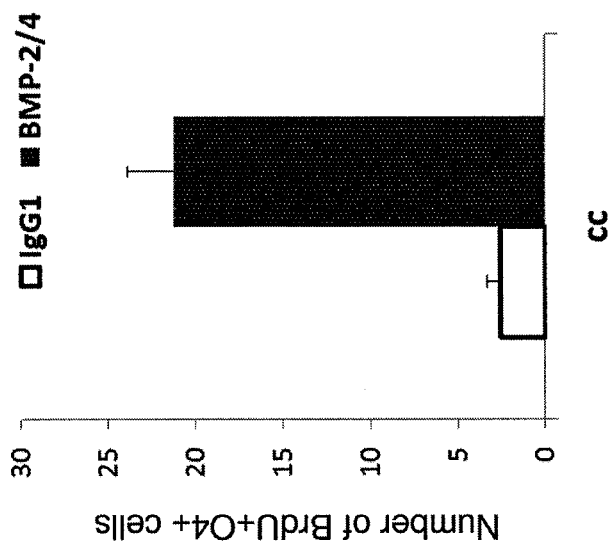
FIG. 14E is a graphical representation of the quantification of BrdU$^+$O4$^+$ cells in cc, performed by analyzing 3 sections from each mouse, 3 mice from each group, total N=9. Coronal sections, images were obtained by a confocal microscopy. Abbreviations: cc, corpus callosum.

As demonstrated in FIG. 14A and FIG. 14B, substantial elevation in the numbers of BrdU$^+$O4$^+$ cells were detected in the corpus callosum of anti-BMP-2/4 treated EAE mice, compared to IgG1 treated mice, suggesting that blockage of BMP-2/4 signaling also enhanced stem cells differentiation towards oligodendrocytes in areas which are known to demyelinate during EAE. Moreover, analysis of a hippocampal lesion in both anti-BMP-2/4 mAb- and IgG1-treated groups revealed that while most of the BrdU$^+$ cells in the lesion of IgG1 treated EAE mice were negative for O4, most of the BrdU$^+$ cells in the lesion of anti-BMP-2/4 mAb treated mice were positive to O4, suggesting that BMP-2/4 blockage possesses the potential to enhance remyelination in EAE (FIG. 14C and FIG. 14D). A quantification of the results presented in FIGS. 14A and 14B, showing the number of BrdU$^+$O4$^+$ cells in the corpus callosum of IgG1- and anti-BMP-2/4 treated EAE is presented in FIG. 14E.

These findings clearly correlate with the ameliorating effect of anti-BMP-2/4 mAb therapy on the EAE clinical symptoms.

Example 12

Clinical Effect of Anti-BMPs mAbs Treatment is not Mediated Via Immunosuppression of T Cells The mechanism underlying the beneficial clinical effect of the treatment with the anti-BMP-2/4, BMP-5 and BMP-7 neutralizing mAbs collectively, or with each of the anti-BMPs as a single agent (namely with anti-BMP-2/4, BMP-5 or BMP-7 mAbs) was examined. In order to examine whether this effect is mediated via the suppression of T cell responses, the proliferation of splenocytes was measured in all RR-EAE mice groups in response to a stimulation via CD3 (10 μg/ml of plate-bound anti-CD3ε) or via PLP (10 μg/ml), at the end of the experiment (day 66), using the tetrazolium salt XTT proliferation assay (n=4 in each group), as follows.

Cells were cultured in 96-plate wells (100,000 cells per well) and were either un-stimulated or stimulated with plate-bound anti-mouse CD3ε (10 μg/ml, or the corresponding IC), or with suspended PLP (10 μg/ml), for 72 hours. The results are presented as the ratios of CD3 stimulation/IC stimulation and PLP stimulation/no stimulation for each mouse.

Figure 15A:
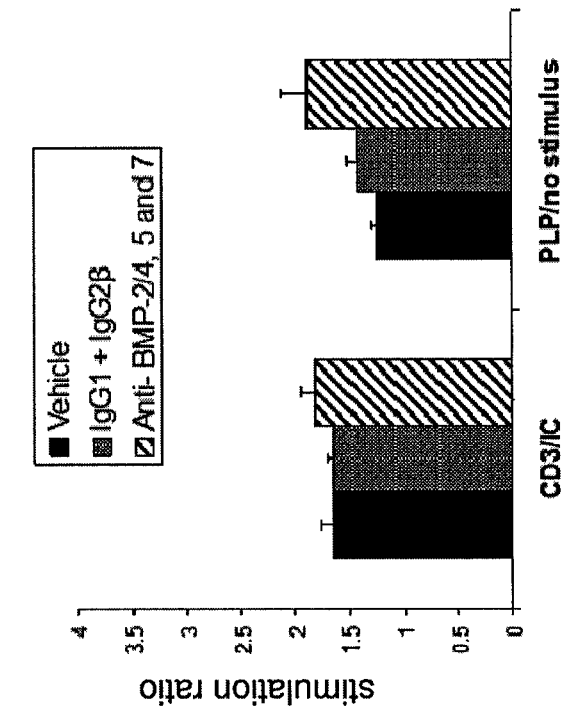
FIG. 15A shows the stimulation ratio of CD3 stimulation/IC stimulation and PLP stimulation/no stimulation in splenocytes obtained from RR-EAE mice treated with a combination of anti-BMP-2/4, 5 and 7 antibodies, a monotherapy of anti-BMP-2/4 antibody is shown in FIG. 15B and a monotherapy of anti-BMP-5 antibody or anti-BMP-7 antibody is shown in FIG. 15C. Abbreviations: IC, isotype control; PLP, Proteolipid protein peptide.

No significant differences in CD3 stimulation/IC stimulation ratio and PLP stimulation/no stimulation ratio were observed for anti-BMP-2/4, 5 and 7 treated EAE mice vs. IgG1+IgG2β treated EAE mice (FIG. 15A), for anti-BMP-2/4 treated EAE mice vs. IgG1 treated EAE mice (FIG. 15B) or for anti-BMP-5 treated EAE mice vs. IgG2γ treated EAE mice (FIG. 15C). However, a significant induction in both CD3 stimulation/IC stimulation ratio and PLP stimulation/no stimulation ratio were observed for anti-BMP-7 treated EAE mice compared to IgG2β treated EAE mice (FIG. 15C).

This finding raises the possibility that anti-BMP-7 mAb may induce T cell responses, thus provide a possible explanation for the observed improved clinical effect of anti-BMP-2/4 mAb alone, compared to treatment with anti-BMP-2/4, 5 and 7 mAbs, collectively.

Notably, no overt side effects of the therapy with the anti-BMPs antibodies were observed in the EAE-treated mice. Namely, except for the weakness/paralysis symptoms there were no overt symptoms: e.g. sudden death, vomiting, seizures, or hair loss.

Example 13

Systemic Administration of Dorsomorphin Ameliorates the Clinical Symptoms of RR-EAE Dorsomorphin, a potent inhibitor of AMP-activated protein kinase (AMPK) and bone morphogenic protein (BMP) signaling (10 mg/kg, Enzo Life Sciences) or vehicle alone (2% wt/volume 2-hydroxypropyl-b-cyclodextrin in PBS (Sigma)), were administered to mice with induced EAE (n=12 in each group) i.p. every 12 hr for 5 days, starting from day 9 post immunization (i.e. post EAE induction), generally following the disclosure by Yu, P. B. et al. [11].

Figure 16:
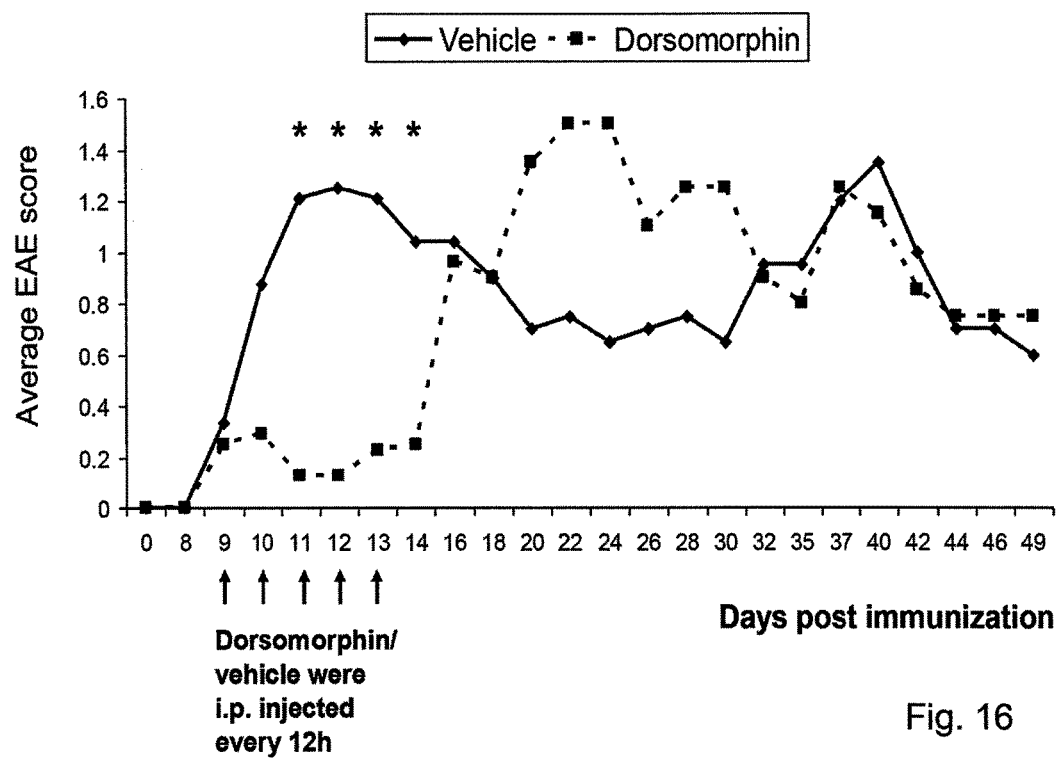
FIG. 16: A graphical representation of the change in the average EAE score of RR-EAE mice treated with dorsomorphin from day 9 to day 13 post EAE induction compared to the change in the average EAE score of RR-EAE mice treated with vehicle alone. The asterisk symbol indicates a significant difference between the groups in the EAE clinical scores between the groups. Abbreviations: EAE, Experimental autoimmune encephalomyelitis; i.p., intraperitoneal.

As demonstrated in FIG. 16, as long as EAE-induced mice were treated with dorsomorphin, they exhibited a very mild form of the disease. Only after dorsomorphin treatment cessation the disease became active, i.e. the onset of the first relapse in dorsomorphin treated-mice was delayed to day 16, compared to day 10 in the vehicle-treated EAE mice.

Figure 17:
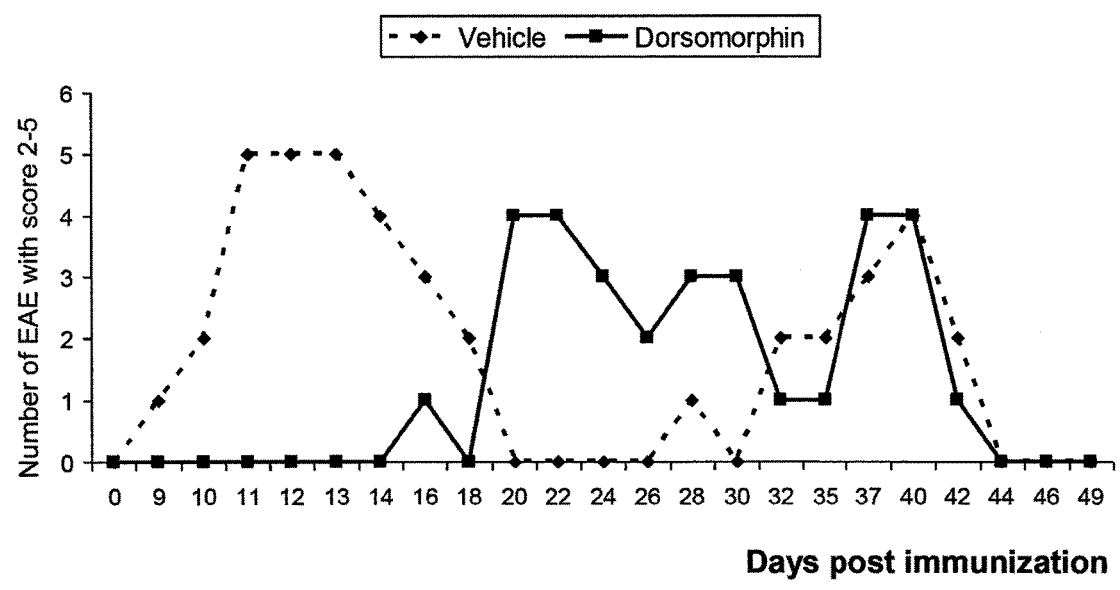
FIG. 17: A graphical representation of the number of RR-EAE mice having an EAE clinical score of 2-5 in the dorsomorphin-treated group (dorsomorphin was administered from day 9 to day 13 post EAE induction), compared to the non-treated group (vehicle alone). Abbreviations: EAE, Experimental autoimmune encephalomyelitis.

As demonstrated in FIG. 17, until day 16 post immunization, there were no mice exhibiting the severe forms of the disease (score 2-5) in the dorsomorphin-treated group, as compared to the vehicle-treated group, in which five mice exhibited a score of >2, on days 11-13 of the experiment.

The invention claimed is:

1. A method for treatment of a subject suffering from multiple sclerosis, comprising administering to said subject a therapeutically effective amount of an anti-Bone Morphogenic Protein (BMP) antibody or a functional fragment thereof and a pharmaceutically acceptable carrier, wherein said antibody is an antibody directed against BMP-2 and BMP-4.

2. A method according to claim 1, wherein said anti-BMP antibody is a monoclonal antibody.

3. A method according to claim 2, wherein said monoclonal antibody is a chimeric, humanized, or human antibody.

4. A method according to claim 1, further comprising administering to said subject at least one additional therapeutic agent.

* * * * *